(12) United States Patent
Trzecieski

(10) Patent No.: US 11,596,174 B2
(45) Date of Patent: Mar. 7, 2023

(54) PHYTO MATERIAL TABLET, METHOD AND APPARATUS

(71) Applicant: GSEH Holistic, Inc., Vancouver (CA)

(72) Inventor: Michael Alexander Trzecieski, Toronto (CA)

(73) Assignee: GSEH Holistic, Inc., Vancouver (CA)

( * ) Notice: Subject to any disclaimer, the term of this patent is extended or adjusted under 35 U.S.C. 154(b) by 950 days.

(21) Appl. No.: 16/220,110

(22) Filed: Dec. 14, 2018

(65) Prior Publication Data

US 2019/0192810 A1 Jun. 27, 2019

Related U.S. Application Data

(63) Continuation-in-part of application No. 15/878,804, filed on Jan. 24, 2018, now abandoned, which is a
(Continued)

(51) Int. Cl.
*A24F 40/46* (2020.01)
*A61M 11/04* (2006.01)
(Continued)

(52) U.S. Cl.
CPC ............ *A24F 40/46* (2020.01); *A24F 40/485* (2020.01); *A61J 3/00* (2013.01); *A61K 9/007* (2013.01);
(Continued)

(58) Field of Classification Search
CPC ........ A24F 40/20; A24F 40/46; A24F 47/008; A61M 11/042; A61M 2202/06; A61L 9/03
See application file for complete search history.

(56) References Cited

U.S. PATENT DOCUMENTS

| | | | | |
|---|---|---|---|---|
| 1,890,920 A | * | 12/1932 | Strawn | A24F 1/16 131/213 |
| 2,255,144 A | * | 9/1941 | Backus | A24F 1/16 131/226 |

(Continued)

FOREIGN PATENT DOCUMENTS

| | | |
|---|---|---|
| EP | 2599514 A1 | 6/2013 |
| WO | 9801175 A1 | 1/1998 |

(Continued)

OTHER PUBLICATIONS

Definition of "tablet" from Random House Kememan Webster's College Dictionary copyrighted 2010 (Year: 2010).*
(Continued)

*Primary Examiner* — Kathryn E Ditmer
(74) *Attorney, Agent, or Firm* — Bereskin & Parr LLP/S.E.N.C.R.L., s.r.l.

(57) ABSTRACT

Phyto material tablets, tablet vaporizers, methods and apparatus for forming phyto material tablets. The tablets are formed to increase vaporization efficiency. Tablets can include break regions to facilitate fracturing into multiple pieces for vaporization. The tablets can also include multiple layers of different phyto material mixtures. Compression molds are used to shape the tablets. The compression molds can be provided on a rotational assembly to facilitate rapid manufacturing of multiple tablets. The vaporizers include heating chambers that are configured to increase the surface area of the tablets exposed for vaporization. The heating chambers include compression or fracture members that compress and/or encourage fracturing of the tablets to assist vaporization.

14 Claims, 46 Drawing Sheets

Related U.S. Application Data continuation of application No. 15/287,038, filed on Oct. 6, 2016, now Pat. No. 9,907,930.

(60) Provisional application No. 62/237,601, filed on Oct. 6, 2015, provisional application No. 62/598,490, filed on Dec. 14, 2017, provisional application No. 62/651,922, filed on Apr. 3, 2018.

(51) Int. Cl.
| | |
|---|---|
| *A61M 15/00* | (2006.01) |
| *A61J 3/00* | (2006.01) |
| *A61M 15/06* | (2006.01) |
| *A24F 40/485* | (2020.01) |
| *A24F 40/20* | (2020.01) |
| *A61M 21/02* | (2006.01) |
| *A61M 15/08* | (2006.01) |
| *A61M 11/00* | (2006.01) |
| *A61K 9/00* | (2006.01) |
| *B33Y 80/00* | (2015.01) |
| *A61M 21/00* | (2006.01) |
| *A61M 16/00* | (2006.01) |

(52) U.S. Cl.
CPC ......... *A61M 11/003* (2014.02); *A61M 11/042* (2014.02); *A61M 15/0023* (2014.02); *A61M 15/0028* (2013.01); *A61M 15/0063* (2014.02); *A61M 15/06* (2013.01); *A61M 15/08* (2013.01); *A61M 21/02* (2013.01); *B33Y 80/00* (2014.12); *A24F 40/20* (2020.01); *A61M 15/0003* (2014.02); *A61M 15/005* (2014.02); *A61M 15/006* (2014.02); *A61M 15/0048* (2014.02); *A61M 2016/0021* (2013.01); *A61M 2016/0033* (2013.01); *A61M 2021/0016* (2013.01); *A61M 2021/0066* (2013.01); *A61M 2202/06* (2013.01); *A61M 2205/3368* (2013.01); *A61M 2205/3606* (2013.01); *A61M 2205/3653* (2013.01); *A61M 2205/583* (2013.01); *A61M 2205/584* (2013.01); *A61M 2205/6045* (2013.01); *A61M 2205/8206* (2013.01); *A61M 2206/20* (2013.01); *A61M 2207/00* (2013.01); *A61M 2207/10* (2013.01); *A61M 2209/06* (2013.01)

(56) References Cited

U.S. PATENT DOCUMENTS

| | | | |
|---|---|---|---|
| 2,443,417 A | 6/1948 | Duncan | |
| 2,449,853 A | 9/1948 | Karp | |
| 2,599,485 A | 6/1952 | Robinson | |
| 4,214,146 A * | 7/1980 | Schimanski | A61L 9/03 128/203.27 |
| 4,588,874 A * | 5/1986 | Napierski | A01M 1/2077 239/136 |
| 5,564,442 A | 10/1996 | MacDonald et al. | |
| 5,692,492 A | 12/1997 | Bruna et al. | |
| 5,819,756 A * | 10/1998 | Mielordt | A61M 15/06 131/330 |
| 7,186,958 B1 | 3/2007 | Nelson | |
| 7,350,720 B2 | 4/2008 | Jaworski et al. | |
| 8,488,952 B2 | 7/2013 | Landry | |
| 8,739,786 B2 | 6/2014 | Postma | |
| 9,907,930 B2 | 3/2018 | Trzecieski | |
| 2006/0102175 A1 | 5/2006 | Nelson | |
| 2007/0257016 A1 | 11/2007 | Jin et al. | |
| 2008/0092880 A1 | 4/2008 | Ooida et al. | |
| 2008/0110454 A1 * | 5/2008 | White | A61M 11/001 128/200.23 |
| 2008/0121244 A1 | 5/2008 | Bryman et al. | |
| 2008/0216824 A1 | 9/2008 | Ooida | |
| 2009/0136390 A1 * | 5/2009 | Yang | A61L 9/03 422/125 |
| 2009/0293892 A1 | 12/2009 | Williams et al. | |
| 2010/0000527 A1 | 1/2010 | Inoue et al. | |
| 2011/0030706 A1 | 2/2011 | Gibson et al. | |
| 2011/0120482 A1 | 5/2011 | Brenneise | |
| 2012/0255546 A1 * | 10/2012 | Goetz | A61M 15/0038 128/202.21 |
| 2012/0325227 A1 | 12/2012 | Robinson et al. | |
| 2013/0174842 A1 | 7/2013 | Young et al. | |
| 2013/0298905 A1 * | 11/2013 | Levin | A24F 40/00 128/202.21 |
| 2014/0041655 A1 | 2/2014 | Barron et al. | |
| 2014/0133841 A1 | 5/2014 | Hsiao | |
| 2014/0217085 A1 | 8/2014 | Alima | |
| 2014/0243635 A1 | 8/2014 | Arefieg | |
| 2014/0338680 A1 | 11/2014 | Abramov et al. | |
| 2014/0348495 A1 | 11/2014 | Greim | |
| 2014/0373857 A1 | 12/2014 | Steinberg | |
| 2015/0223292 A1 | 8/2015 | Duffield et al. | |
| 2015/0223523 A1 | 8/2015 | Mccullough | |
| 2016/0015847 A1 | 1/2016 | Irvin et al. | |
| 2016/0106153 A1 | 4/2016 | Zhu | |
| 2016/0120218 A1 | 5/2016 | Schennum et al. | |
| 2016/0166786 A1 * | 6/2016 | Kinzer | A61K 31/015 128/200.14 |
| 2016/0287816 A1 | 10/2016 | Eksouzian | |
| 2016/0346490 A1 | 12/2016 | Beller | |
| 2017/0027223 A1 | 2/2017 | Eksouzian | |
| 2017/0086506 A1 * | 3/2017 | Rado | A61M 15/06 |
| 2017/0095639 A1 | 4/2017 | Trzecieski | |
| 2017/0304563 A1 * | 10/2017 | Adelson | A61M 11/041 |
| 2017/0340843 A1 * | 11/2017 | Harris | A61M 15/0043 |
| 2018/0043115 A1 * | 2/2018 | Gould | A24F 40/42 |
| 2018/0084823 A1 * | 3/2018 | Fuisz | A24B 15/167 |
| 2018/0207394 A1 | 7/2018 | Trzecieski | |
| 2018/0280459 A1 | 10/2018 | Eyal | |
| 2019/0125988 A1 | 5/2019 | Trzecieski | |
| 2020/0046023 A1 * | 2/2020 | Reevell | A24D 1/20 |
| 2020/0221767 A1 * | 7/2020 | Emmett | A24F 40/40 |

FOREIGN PATENT DOCUMENTS

| | | |
|---|---|---|
| WO | 2005120614 A1 | 12/2005 |
| WO | 2012085919 A2 | 6/2012 |
| WO | 2012114322 A1 | 8/2012 |
| WO | 2016187695 A1 | 12/2016 |
| WO | 2016187696 A1 | 12/2016 |
| WO | 2017158539 A1 | 9/2017 |
| WO | WO-2017202953 A1 * | 11/2017 ............... A24D 1/20 |
| WO | WO-2017202965 A1 * | 11/2017 ............ A61M 15/06 |

OTHER PUBLICATIONS

Document relating to previously co-pending, now abandoned, U.S. Appl. No. 15/878,804—Office Action dated Apr. 24, 2020, 41 pages.

* cited by examiner

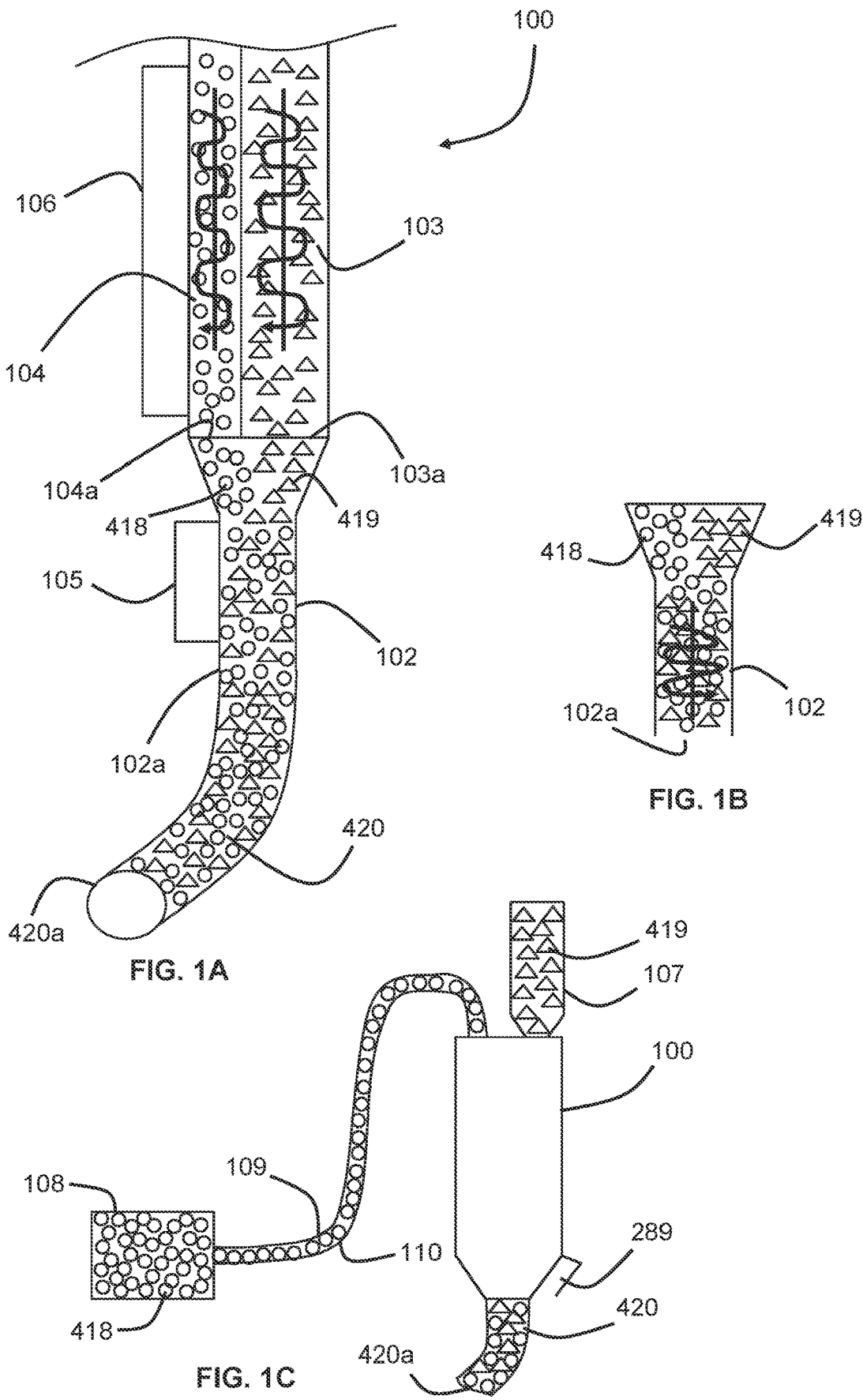

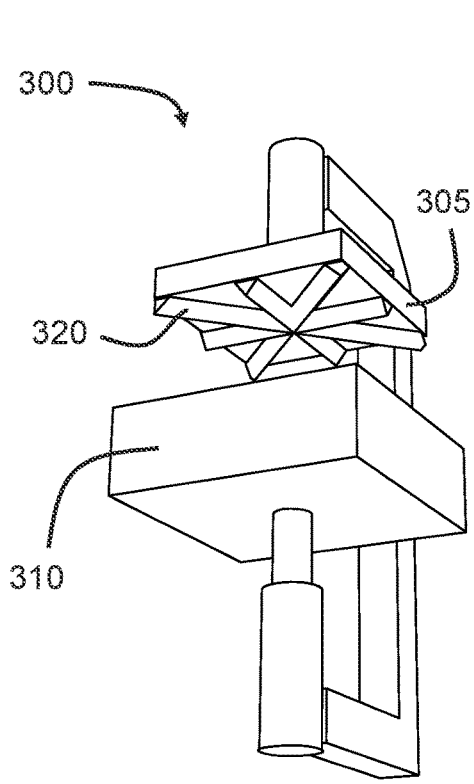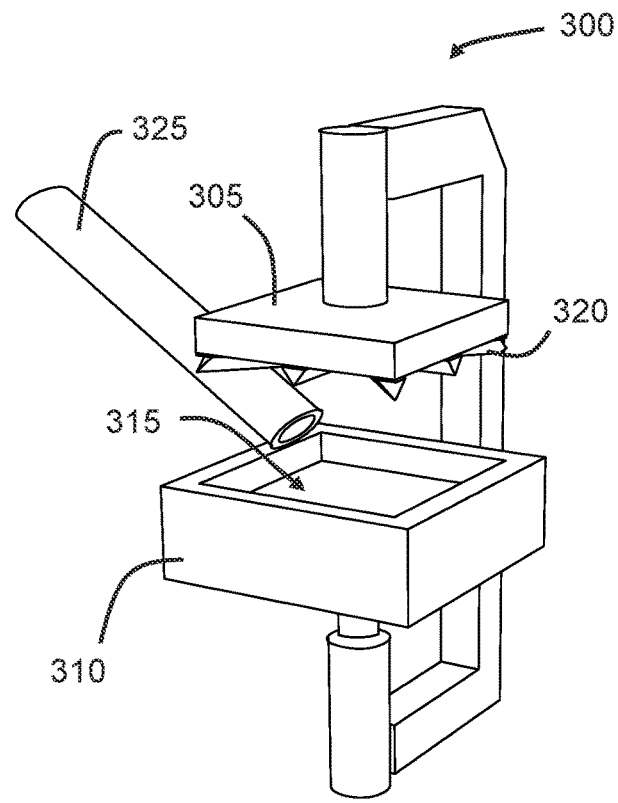
FIG. 3A FIG. 3B
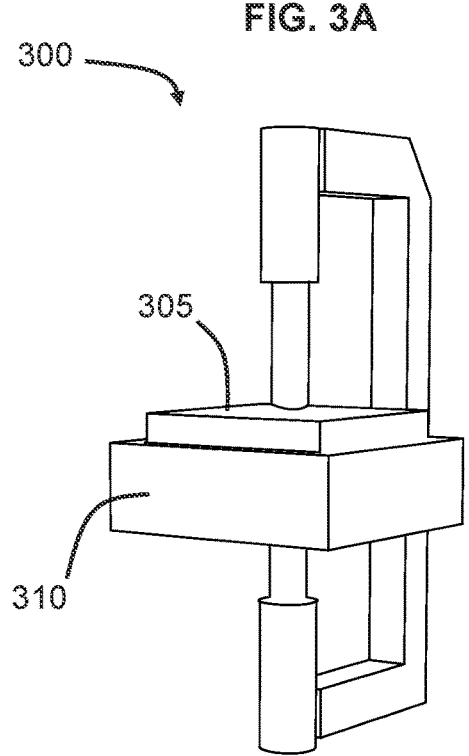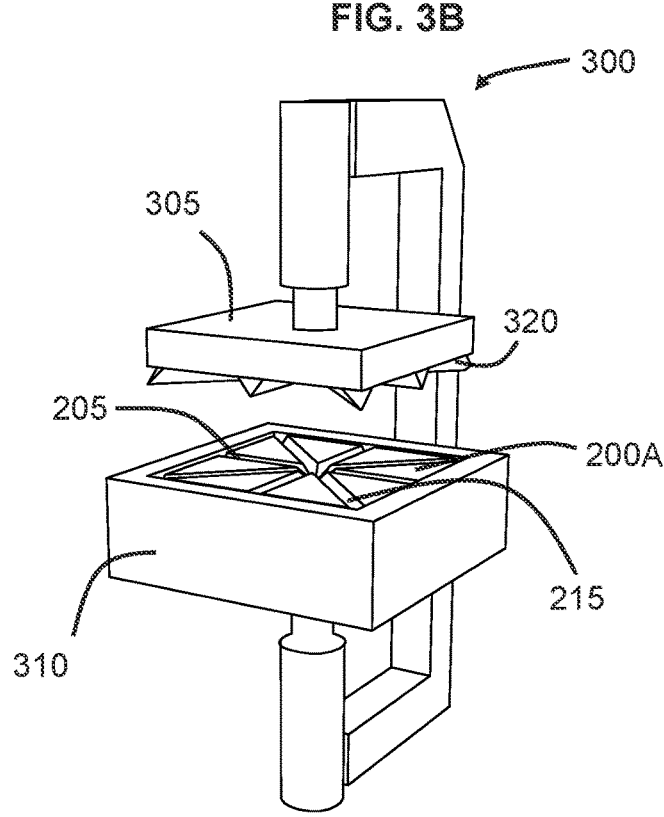
FIG. 3C FIG. 3D

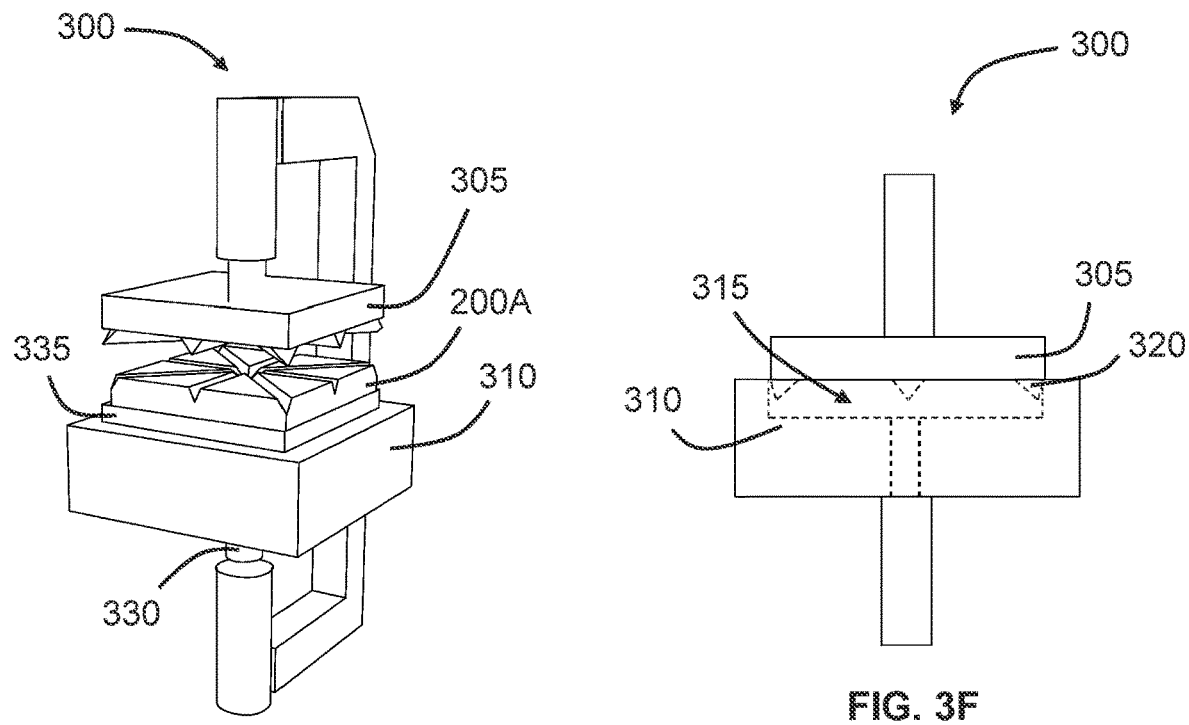
FIG. 3E
FIG. 3F
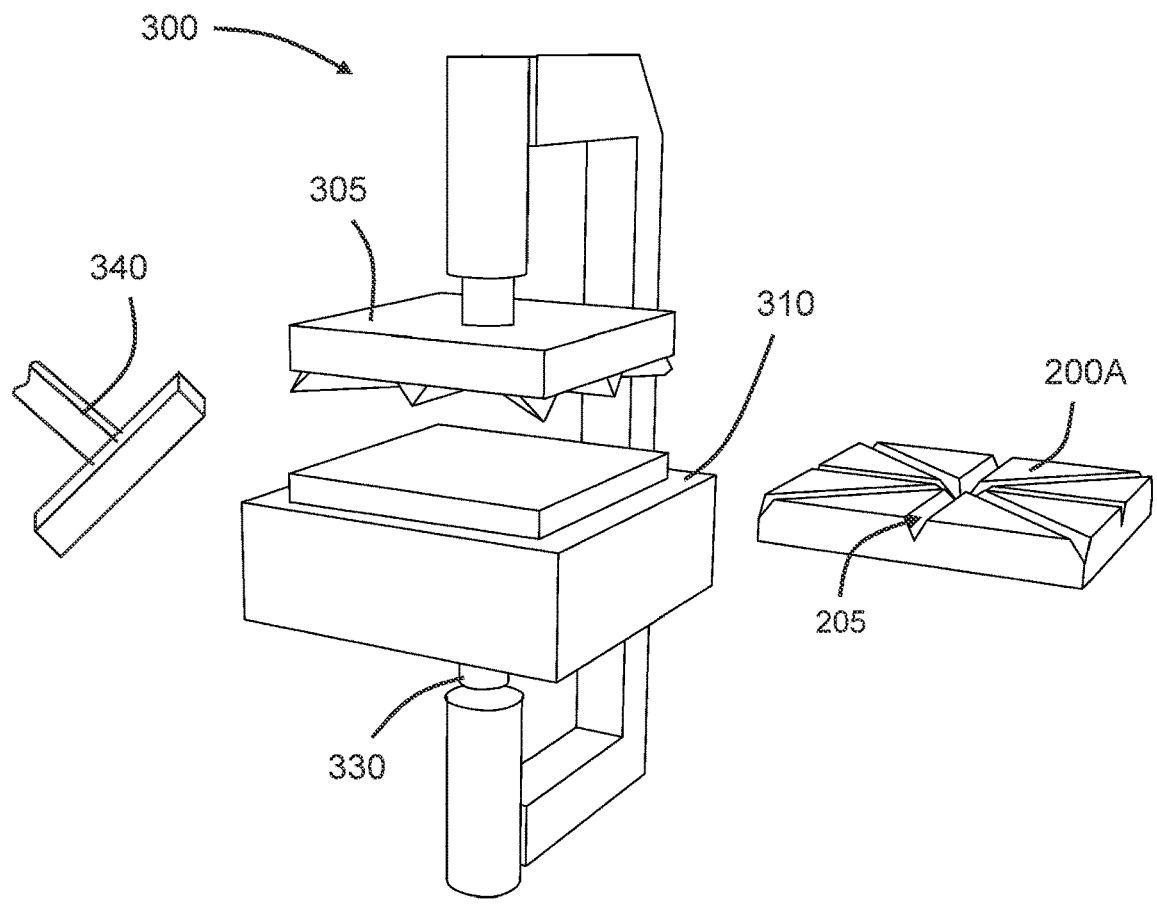
FIG. 3G

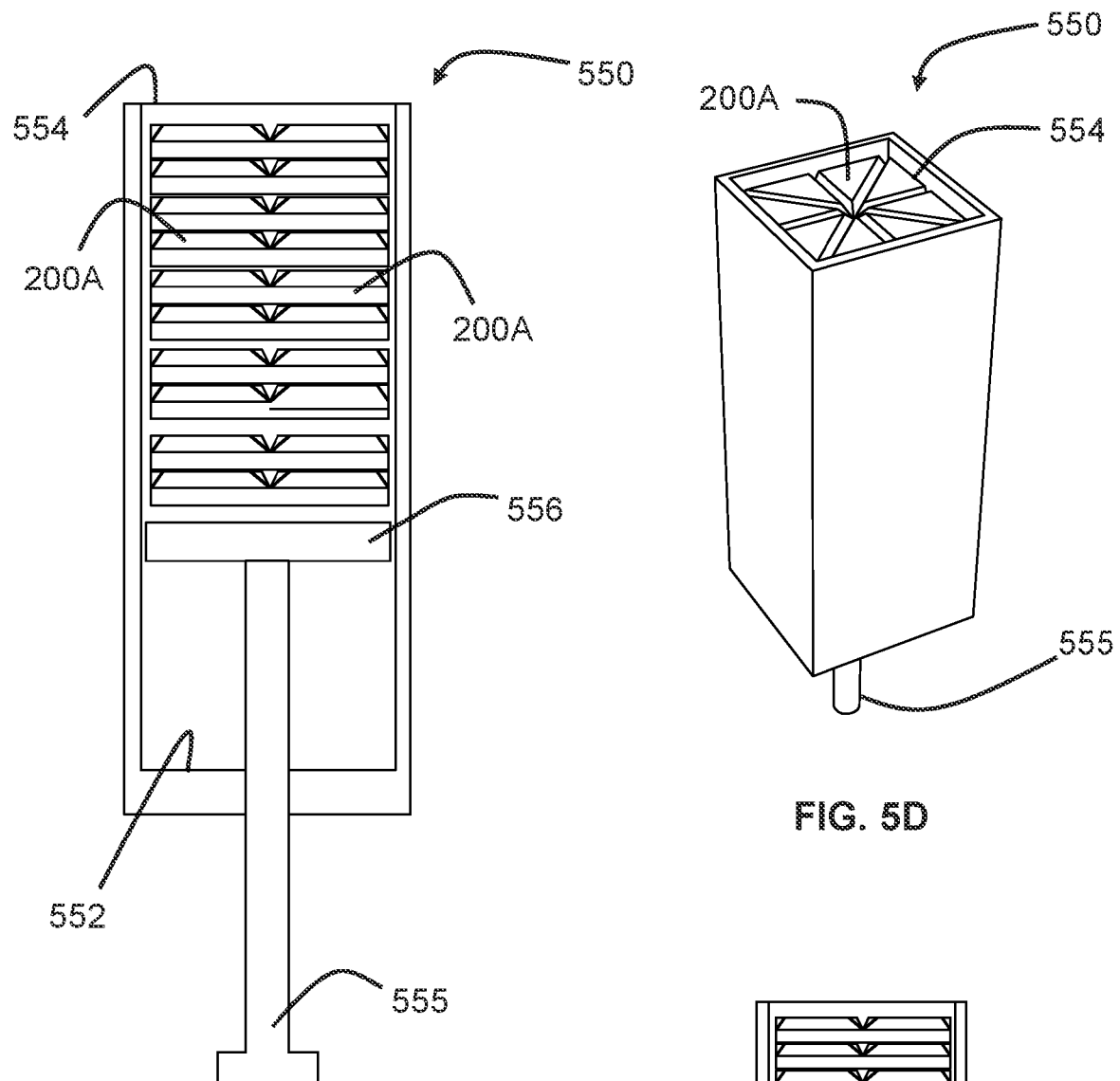
FIG. 5C
FIG. 5D
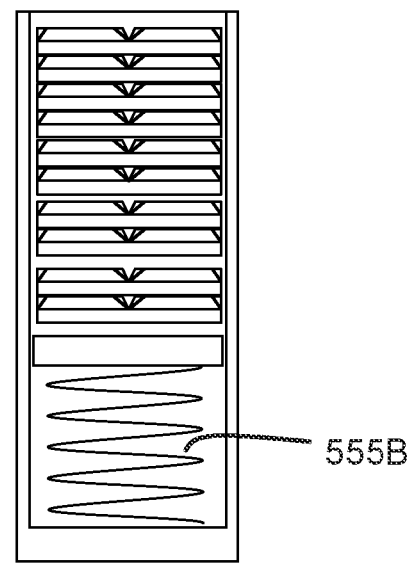
FIG. 5E

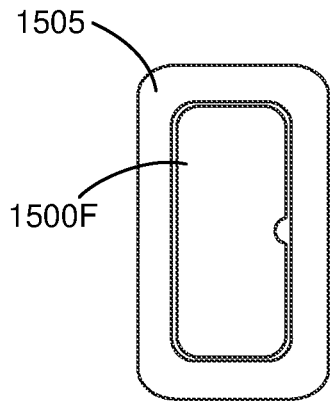
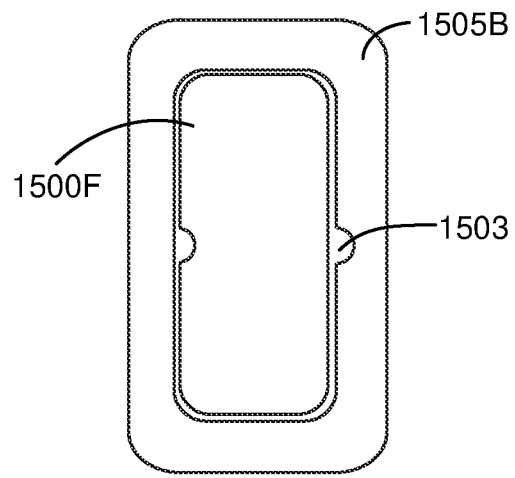
FIG. 15H  FIG. 15I
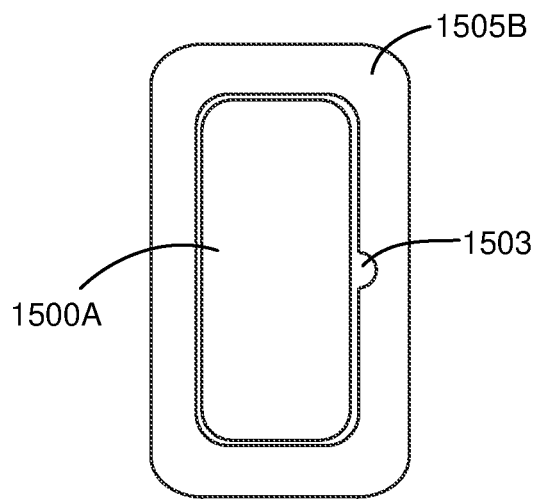
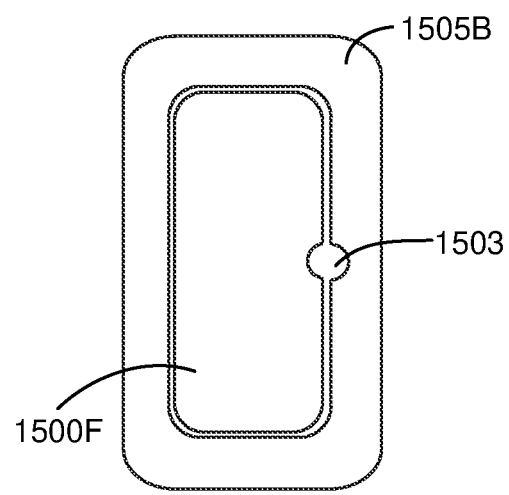
FIG. 15J  FIG. 15K

FIG. 16A

| CBD% \ THC% | 0-3 | 3-6 | 6-9 | 9-12 | 12-15 | 15-18 | 18-21 | 21-24 | 24-27 | 27-30 | 30-33 | 33-36 | 36-39 | 39-42 | 42-45 |
|---|---|---|---|---|---|---|---|---|---|---|---|---|---|---|---|
| 0-3 |  |  | X | X | X | X | X | X | X | X |  |  |  |  |  |
| 3-6 |  |  |  |  | X | X | X | X |  |  |  |  |  |  |  |
| 6-9 | X | X | X | X | X | X |  |  |  |  |  |  |  |  |  |
| 9-12 |  | X | X | X | X |  |  |  |  |  |  |  |  |  |  |
| 12-15 | X | X | X | X | X |  |  |  |  |  |  |  |  |  |  |
| 15-18 | X | X |  |  |  |  |  |  |  |  |  |  |  |  |  |
| 18-21 | X |  |  |  |  |  |  |  |  |  |  |  |  |  |  |
| 21-24 | X |  |  |  |  |  |  |  |  |  |  |  |  |  |  |
| 24-27 | X |  |  |  |  |  |  |  |  |  |  |  |  |  |  |
| 27-30 |  |  |  |  |  |  |  |  |  |  |  |  |  |  |  |
| 30-33 |  |  |  |  |  |  |  |  |  |  |  |  |  |  |  |
| 33-36 |  |  |  |  |  |  |  |  |  |  |  |  |  |  |  |

FIG. 16B

| CBD% \ THC% | 0-3 | 3-6 | 6-9 | 9-12 | 12-15 | 15-18 | 18-21 | 21-24 | 24-27 | 27-30 | 30-33 | 33-36 | 36-39 | 39-42 | 42-45 |
|---|---|---|---|---|---|---|---|---|---|---|---|---|---|---|---|
| 0-3 | X | X | X | X | X | X | X | X | X | X | X | X | X | X | X |
| 3-6 | X | X | X | X | X | X | X | X | X | X | X | X | X | X |  |
| 6-9 | X | X | X | X | X | X | X | X | X | X | X | X | X |  |  |
| 9-12 | X | X | X | X | X | X | X | X | X | X | X | X |  |  |  |
| 12-15 | X | X | X | X | X | X | X | X | X | X | X |  |  |  |  |
| 15-18 | X | X | X | X | X | X | X | X | X | X |  |  |  |  |  |
| 18-21 | X | X | X | X | X |  |  |  |  |  |  |  |  |  |  |
| 21-24 | X | X | X | X |  |  |  |  |  |  |  |  |  |  |  |
| 24-27 | X | X | X |  |  |  |  |  |  |  |  |  |  |  |  |
| 27-30 | X |  |  |  |  |  |  |  |  |  |  |  |  |  |  |
| 30-33 | X |  |  |  |  |  |  |  |  |  |  |  |  |  |  |
| 33-36 | X |  |  |  |  |  |  |  |  |  |  |  |  |  |  |

PHYTO MATERIAL TABLET, METHOD AND APPARATUS

CROSS-REFERENCE TO RELATED APPLICATIONS

This application is a continuation-in-part of U.S. application Ser. No. 15/878,804, filed on Jan. 24, 2018, which is a continuation of U.S. application Ser. No. 15/287,038, filed Oct. 6, 2016, which claims the benefit of the U.S. Provisional Application No. 62/237,601, filed on Oct. 6, 2015. The entire content of U.S. application Ser. No. 15/878,804, U.S. application Ser. No. 15/287,038 and U.S. Provisional Application No. 62/237,601 are incorporated herein by reference. This application also claims the benefit of U.S. Provisional Application No. 62/598,490, filed Dec. 14, 2017, and U.S. Provisional Application No. 62/651,922, filed Apr. 3, 2018, the entirety of each of which are incorporated herein by reference.

FIELD OF THE INVENTION

This disclosure relates generally to vaporization of phyto materials, and in particular to vaporizable phyto material tablets, vaporization devices for phyto material tablets and methods of forming phyto material tablets.

BACKGROUND

The following is intended to introduce the reader to the detailed description that follows and not to define or limit the claimed subject matter.

Various methods of vaporizing phyto materials, such as cannabis products, are known. For instance, PCT Publication No. WO2016/187695A1 of Davis purports to describe a vaporizer apparatus for a compressed tablet formed from a plant source material containing medicinal ingredients of therapeutic efficacy. In an embodiment, the apparatus includes: a holder for a compressed tablet; a microprocessor; a controlled air flow; and a controlled heat source; wherein the microprocessor is adapted to control the air flow and the heat source to vaporize the compressed tablet received in the compressed tablet holder at a desired rate. In another embodiment, the vaporizer apparatus includes a carousel for receiving a disc cartridge containing packaged compressed tablets. In still another embodiment, the vaporizer apparatus is adapted to recognize a type of compressed tablet placed into the holder, and to control an air flow and a heat source based on selected therapeutic compounds desired to be released from the recognized type of compressed tablet.

PCT Publication No. WO2016/187696A1 of Davis purports to describe a compressed vaporizer tablet and method. In an embodiment, the method comprises: obtaining one or more plant source materials containing one or more active medicinal ingredients; compressing the one or more plant source materials under pressure and heat into a tablet; and forming one or more through holes in the tablet, whereby the through holes provide increased tablet surface area during vaporization. The tablet may further include one or more ribbed edges to further increase the tablet surface area. The tablet is preferably individually sealed in a blister pack to increase shelf life of the tablet, and to provide safety and convenience features for use.

SUMMARY

The following introduction is provided to introduce the reader to the more detailed description to follow and not to limit or define any claimed or as yet unclaimed invention. One or more inventions may reside in any combination or sub-combination of the elements or process steps disclosed in any part of this document including its claims and figures.

In accordance with a first aspect of this disclosure, there is provided a phyto material tablet. The phyto material tablet can be formed to facilitate vaporization in a conduction and/or convection and/or induction and/or combination convection/conduction vaporizer.

The phyto material tablet may initially be a substantially solid tablet with a first exposed surface area. The tablet can be formed to facilitate fracturing or breaking into multiple pieces prior to being vaporized. Following fracturing, the tablet may be separated into a plurality of separate tablet pieces. The combined exposed surface area of the separate tablet pieces can be greater than the initially exposed surface area of the phyto material tablet.

In some cases, the phyto material tablet can be formed with one or more regions of weakness. The regions of weakness may facilitate fracturing the phyto material tablet into multiple pieces. For instance, the regions of weakness may include areas of reduced thickness formed into the tablets, such as recesses extending partially into the tablets. These regions of weakness can be formed without passing completely through the tablets. This may facilitate manufacturing of the tablets using phyto material which can be sticky.

In some cases, a phyto material tablet can be formed without any regions of weakness. A phyto material tablet omitting regions of weakness may occupy a smaller volume than one that a phyto material tablet formed with one or more regions of weakness.

In some cases, a phyto material tablet may be formed using a blend of phyto material products. The blend of phyto material products may include a first phyto material derived from cannabis that has a first ratio of specified components (i.e. a first ratio of THC, CBD, and terpenes) and a second phyto material derived from cannabis that has a second ratio of specified components (i.e. a second ratio of THC, CBD, and terpenes). The blend of phyto material products may include a first predetermined weight of the first phyto material blended with a second predetermined weight of the second phyto material. The blend may be defined to provide a specified ratio of key components In some embodiments, a phyto material tablet can include compressed ground phyto material shaped to define an outer tablet surface, the outer tablet surface including an upper surface, a side surface, and at least one tablet side surface; and at least one recess formed in the outer tablet surface; where the tablet omits any through-holes.

In some embodiments, the at least one recess includes at least one upper surface recess provided in the upper surface, the at least one upper surface recess configured to define a plurality of fracturing sections of the phyto material tablet; each recess defines a region of reduced thickness of the phyto material tablet that encourages fracturing of the tablet into the plurality of fracturing sections.

In some embodiments, the at least one recess includes a plurality of recess on the tablet outer surface.

In some embodiments, the compressed ground phyto material includes ground phyto material from a plurality of different cannabis strains.

In some embodiments, the tablet includes at least one non-cannabis terpene that is derived from a plant other than cannabis.

In some embodiments, the at least one non cannabis terpene is selected from the group consisting of pinene, limonene, linalool, caryophyllene, myrcene, humulene, borneol, eucalyptol, terpineol, nerolidol, phytol, geraniol, bisabolol, camphene, beta-amyrin, thujone, citronellol, pulegone, 1,8-cineole and cycloarteno.

In some embodiments, the tablet can include cannabis extract. The cannabis extract may be deposited on an outer surface of the tablet. In some cases, the cannabis extract may be mixed with the ground phyto material prior to compression of the tablet.

In some embodiments, a phyto material tablet may include a plurality of layers, where each layer includes a different combination of active components. In some embodiments, the tablet may include two or stratified layers.

In some embodiments, the layers of the tablet may be formed sequentially. A first layer can be deposited and compressed to form the first tablet layer and a subsequent layer can be deposited on the first tablet layer and subsequently compressed to form a combined multi-layer tablet. This process may be repeated for a plurality of layers.

In some cases, additional components, such as resin binders, may be deposited between the layers of compressed phyto material.

In some cases, the phyto material tablets may include an orientation marker. The orientation marker may provide a visual indication of a particular surface of the phyto material tablet. For example, the orientation marker may identify the top and/or bottom surface of the phyto material tablet.

In accordance with another aspect of this disclosure, there is provided a vaporizer for a phyto material tablet. In some embodiments, vaporizer may include or more features arranged to compress and/or fracture a phyto material tablet inserted into the vaporizer.

The vaporizer may include a heating chamber for vaporizing a phyto material tablet. One or more inner surfaces of the heating chamber can be shaped to fracture a tablet inserted therein. In some cases, the inner surfaces of the heating chamber can be shaped to selectively apply force to different areas of a tablet in the heating chamber (i.e. to apply different levels of force at points or areas across the surface of the tablet). For example, one or more inner surfaces of the heating chamber may be non-planar.

In some cases, the heating chamber lid may be used to apply force to a tablet inserted in the heating chamber. For example, as the lid is closed, force may be selectively applied to the tablet by protrusions or non-planar surface regions in the lid and/or bottom surface of the heating chamber. The applied force may compress the tablet within the heating chamber.

In some embodiments, the heating chamber lid can be provided by a removable mouthpiece.

In some embodiments, the heating chamber lid may include a protrusion or projecting member that extends into the heating chamber when the lid is in a closed position. The projecting member can apply force to a tablet inserted in the heating chamber.

In some embodiments, as the heating chamber lid is closed, force may be selectively applied to the tablet by the protrusions or non-planar surface regions in the lid and/or bottom surface of the heating chamber lid.

In some cases, a plunger may be used to initiate the application of force to the phyto material tablet. For example, a plunger may be positioned below, or forming part of the base of, the heating chamber. When a tablet is inserted into the heating chamber the plunger may be pushed upwards (i.e. into the heating chamber) to apply force to regions of the tablet.

In some cases, the plunger may form part of a lateral wall of the heating chamber. For instance, the plunger may be used to insert a tablet into the heating chamber. The plunger may initially extend partially into the heating chamber to apply a force on the side of the tablet. This force may then fracture the tablet. The plunger may then retract to allow the tablet to spread across a larger area within the heating chamber.

In some cases, the plunger may initially extend partially into the heating chamber to apply a force on a side of the tablet having a larger surface area. The applied force may also transfer to the force applied between the tablet and the inner walls of the heating chamber. The increased force between the tablet and the inner heating chamber walls can increase thermal transfer from the heating chamber walls to the tablet. This can facilitate penetration of conductive heating into the phyto material of the tablet faster than without the force being applied. In some cases, the plunger can be configured to apply a force between about 0.1 Newton and 1 Newton.

In some cases, the vaporizer may be configured to apply an initial heat level to the heating chamber. This initial heat level may facilitate fracturing the phyto material tablet. This initial heat level may be selected to be lower than the level required to vaporize the phyto material. Once the tablet is fractured, the heat level may be increased to a temperature sufficient to vaporize the phyto material.

In some case, the vaporizer may include a dispensing magazine. A magazine may be inserted into the vaporizer that includes a plurality of tablets. The vaporizer can include a transport mechanism that moves a tablet from the magazine into the heating chamber for vaporization. This may facilitate vaporizing multiple doses of phyto material without having to manually load and reload the vaporizer. In some cases, the transport mechanism may also be configured to fracture a tablet as it is inserted into the heating chamber.

In accordance with this broad aspect, there is provided a vaporization device comprising: an inhalation aperture; a heating chamber having a chamber base, at least one chamber sidewall, and a chamber lid that define a phyto material receiving cavity, the phyto material receiving cavity shaped to receive a phyto material tablet; at least one air inlet fluidly coupled to the heating chamber; at least one chamber vapor outlet fluidly coupled to the heating chamber and the inhalation aperture; a vapor flow path that extends from the at least one air inlet through the heating chamber to the at least one chamber vapor outlet and then to the inhalation aperture; and a heating element assembly positioned proximate the heating chamber, the heating element operable to heat phyto material within the phyto material receiving cavity, wherein when a phyto material tablet is positioned in the heating chamber and the at least one heating element is heated to a predetermined vaporization temperature, thermal energy from the heating element heats the phyto material tablet and causes emission of vapor from the phyto material tablet, whereby the emitted vapor is fluidly coupled to the inhalation aperture via the vapor flow path; wherein at least one inner surface of the phyto material receiving cavity includes a projecting member that is configured to compress at least a portion of the phyto material tablet when the phyto material tablet is received in the phyto material receiving cavity and the chamber lid is secured to the chamber base enclosing the phyto material receiving cavity.

In some embodiments, the chamber lid is moveably mounted to the chamber base, the chamber lid being moveable between an open position in which the heating chamber cavity is accessible and a closed position in which the heating chamber cavity is enclosed.

In some embodiments, the base and the one or more sidewalls define a base portion of the phyto material receiving cavity, the base portion having an open upper end; and an inner surface of the chamber lid includes a lid projecting member that extends into the base portion when the lid is in the closed position.

In some embodiments, the lid projecting member extends across substantially all of the open upper end when the lid is in the closed position.

In some embodiments, the vaporization device comprises a first body portion and a second body portion; the first body portion includes the chamber base and the at least one chamber sidewall; the second body portion including the chamber lid; the second body portion is moveably mounted to the first body portion between an open position and a closed position, in the open position the chamber lid is open and the heating chamber cavity is accessible and in the closed position the heating chamber cavity is enclosed by the chamber lid; the second body portion encloses a lid vapor flow path that is fluidly coupled to the heating chamber cavity when the second body portion is in the closed position.

In some embodiments, the chamber lid includes an ambient air inlet and when the second body portion is in the closed position the lid vapor flow path extends between the ambient air inlet and the heating chamber cavity.

In some embodiments, the at least one chamber vapor outlet is provided in the chamber lid; the first body portion comprises a downstream vapor flow path that extends between a first portion vapor inlet and the inhalation aperture; when the second body portion is in the closed position the lid vapor flow path extends between the at least one chamber vapor outlet and a lid outlet, the lid outlet being fluidly engageable with the first portion vapor inlet.

In some embodiments, a cooling assembly can be coupled to the lid vapor flow path.

In some embodiments, the vaporization device can include a tablet transport unit, the tablet transport unit operable to transport a phyto material tablet from a dispensing magazine into the heating chamber cavity.

In some embodiments, the dispensing magazine houses a plurality of phyto material tablets.

In some embodiments, the dispensing magazine is enclosed within a housing of the vaporization device.

In some embodiments, the heating element assembly comprises a plurality of heating elements, the plurality of heating elements including a first heating element positioned at a floor of the heating chamber and a second heating element positioned at the sidewalls of the heating chamber.

In some embodiments, the plurality of heating elements includes a third heating element positioned at the lid of the heating chamber.

In some embodiments, the chamber lid is moveably mounted to the chamber base, the chamber lid being moveable between an open position in which the heating chamber cavity is accessible and a closed position in which the heating chamber cavity is enclosed; the at least one projecting member includes at least one fracturing protrusion, and when a phyto material tablet is positioned in the heating chamber and the chamber lid is moved from the open position to the closed position, the fracturing protrusion applies a directed pressure at the phyto material tablet whereby fracturing of the phyto material tablet is promoted. This may facilitate increasing the exposed surface area of the phyto material tablet.

In some embodiments, the vaporization device includes a plunger that is moveable between an extended position and a retracted position, in the extended position the plunger projects into the heating chamber cavity, and in the retracted position the plunger is receded from the chamber cavity.

In some embodiments, the plunger is operable to translate a phyto material tablet from a dispensing magazine into the heating chamber cavity as the plunger moves from the retracted position to the extended position.

In accordance with another aspect of this disclosure, there is provided an apparatus for forming a phyto material tablet, the apparatus comprising: a base that defines a phyto material receiving volume having a volume base, a volume upper end, and at least one volume lateral side extending between the volume base and the volume upper end, wherein the volume upper end is open, the base comprising: a die having a sidewall that define a cavity that extends through at least a portion of the base in an axial direction, the sidewalls defining the at least one volume lateral side of the phyto material receiving volume; and a first compression member that is moveable within the cavity along the axial direction, the first compression member having a first compression surface that defines the volume base of the phyto material receiving volume; and a second compression member that is moveable relative to the base along the axial direction, the second compression member comprising a second compression surface that is aligned with and faces the volume upper end of the phyto material receiving volume; wherein the first compression member is moveable along the axial direction between a first member retracted position and a first member extended position, in the first member retracted position the first compression member is recessed below the volume upper end, and in the first member extended position the first compression member extends to at least the volume upper end of the phyto material receiving volume; the second compression member is moveable along the axial direction between a second member retracted position and a second member extended position, in the second member extended position the second compression member engages the volume upper end of the phyto material receiving volume, and in the second member retracted position the second compression member is axially spaced from the volume upper end; and the first compression member and second compression member are moveable towards one another to compress phyto material positioned within the phyto material receiving volume between the first compression surface and the second compression surface.

In some embodiments, at least one of the first compression surface and the second compression surface has an outwardly extending projection that extends outwardly in the axial direction.

In some embodiments, the die sidewall has an inwardly extending sidewall projection that extends inwardly to define a notch in the phyto material receiving volume.

In some embodiments, the apparatus includes a dispensing unit that is mounted to the base, where the dispensing unit includes an open dispensing end configured to face the volume upper end, where when the first compression member and second compression member are in their respective retracted position, the dispensing unit is configured to dispense phyto material into the phyto material receiving volume.

In some embodiments, the base includes a plurality of dies and a corresponding plurality of first compression members; the apparatus comprises a plurality of second compression members, each second compression member aligned with the volume upper end of the phyto material receiving volume defined by one of the dies and corresponding first compression member; and the apparatus comprises a plurality of tablet forming units, each tablet forming unit comprising one of the dies, the corresponding first compression member, and the corresponding second compression member.

In some embodiments, the apparatus includes a dispensing unit comprising an open dispensing end configured to face the volume upper end of each phyto material receiving volume, wherein when the open dispensing end is arranged to face the volume upper end of a particular phyto material receiving volume and the first compression member and second compression member associated with that particular phyto material receiving volume are in their respective retracted position, the dispensing unit is configured to dispense phyto material into the phyto material receiving volume of that particular phyto material receiving volume.

In some embodiments, the plurality of tablet forming units are moveably mounted to the dispensing unit; and the apparatus is configured to sequentially align each of the tablet forming units with the open dispensing end.

In some embodiments, the open dispensing end is shaped to overlie at least two of the tablet forming units at the same time.

In some embodiments, the plurality of tablet forming units are circumferentially arranged around a central apparatus axis; and the plurality of tablet forming units are rotatable about the central apparatus axis.

In some embodiments, the dispensing unit is stationary.

In some embodiments, the dispensing unit comprises an internal dispensing volume that extends between the open dispensing end and a second feed end, the internal dispensing volume including a sidewall that extends around the perimeter of the internal dispensing volume at the open dispensing end, and the sidewall contacts an upper surface of the base at the open dispensing end.

In some embodiments, the dispensing unit comprises an agitation member positioned within the internal dispensing volume, the agitation member being moveable within the internal dispensing volume.

In some embodiments, each die has a first radial width; the open dispensing end has a second radial width; and the second radial width is at least 1.5 times larger than the first radial width.

In accordance with an aspect of this disclosure, there is provided a method of forming a phyto material tablet. Phyto material derived from plant matter can be ground to a substantially consistent grind or coarseness. The phyto material may then be pressed into a tablet using a compression mold. In some cases, the phyto material may be filtered prior to pressing. This may provide a more consistent coarseness of phyto material.

The compression mold may include one or more protrusions. The protrusions may extend partially into, but not completely through, the mold cavity. When phyto material is pressed using the compression mold, regions of reduced thickness can be formed in the phyto material tablets by the protrusions. This may form break regions or regions of weakness to facilitate fracturing the tablets into multiple pieces.

In some cases, a phyto material mixture or slurry may be used. Phyto material may be mixed with phyto material extracts to form a phyto material slurry. This slurry may then be used to form phyto material tablets. For instance, the phyto material mixture may be loaded into the compression mold for molding into a phyto material tablet. In some cases, the phyto material mixture may be used to 3-D print phyto material tablets.

In accordance with this aspect of this disclosure, there is provided a method of forming a phyto material tablet, the method comprising: grinding phyto material to form ground phyto material having a predetermined particle size; compressing the ground phyto material; and forming at least one recess in an outer surface of the tablet.

In some embodiments, the at least one recess is formed while the ground phyto material is being compressed.

In some embodiments, the method includes loading the ground phyto material into a die that defines the sidewalls of a phyto material receiving volume having an open upper end; enclosing the ground phyto material within the phyto material receiving volume by moving an upper mold portion to the open upper end; compressing the ground phyto material by moving the upper mold portion and an opposite lower mold portion towards one another with the ground phyto material therebetween; wherein at least one of the upper mold portion, lower mold portion and sidewalls include at least one projection corresponding to the at least one recess.

In some embodiments, the method includes dispensing a first volume of a first phyto material, the first phyto material comprising a first strain of cannabis plant; dispensing a second volume of a second phyto material, the second phyto material comprising a second strain of cannabis plant; grinding the first volume and the second volume; and combining the ground first volume and the ground second volume to provide the ground phyto material.

In some embodiments, the first volume and the second volume are combined prior to grinding.

In some embodiments, the first volume and the second volume are combined after grinding; and combining the ground first volume and the ground second comprises: measuring a first predefined weight of the ground first volume; measuring a second predefined weight of the ground second volume; positioning the first predefined volume and the second predefined volume within a mixing container; and mixing the first predefined volume and the second predefined volume.

In some embodiments, the process of loading ground phyto material into a die, enclosing the ground phyto material within the die, and compressing the phyto material within the die is repeated multiple times to form a single phyto material tablet having multiple phyto material layers.

In some embodiments, the ground phyto material loaded into the die differs for at least two of the phyto material layers.

In some embodiments, additional components are deposited between the layers of ground phyto material. In some embodiments, the additional components include at least one non-cannabis terpene.

In some embodiments, the method includes filtering the ground phyto material.

In some embodiments, the method includes depositing at least one terpene on the phyto material tablet.

In some embodiments, the at least one terpene comprises at least one non-cannabis terpene that is derived from a plant other than cannabis.

In some embodiments, the at least one non cannabis terpene is selected from the group consisting of pinene, limonene, linalool, caryophyllene, myrcene, humulene, borneol, eucalyptol, terpineol, nerolidol, phytol, geraniol, bisabolol, camphene, beta-amyrin, thujone, citronellol, pulegone, 1,8-cineole and cycloarteno.

In some embodiments, the method includes positioning the tablet within a storage container; and depositing the at least one terpene on the phyto material tablet while the tablet is positioned within the storage container.

In some embodiments, sealing the storage container after the at least one terpene has been deposited.

In accordance with an aspect of this disclosure, there is provided a method of forming a phyto material tablet, the method comprising: grinding phyto material to form ground phyto material having a predetermined particle size, wherein the phyto material is derived from plant matter; loading the ground phyto material into a mold cavity of a compression mold, wherein the mold cavity is formed from a first portion and a second portion that together form the mold cavity when the periphery of the first portion and the second portion contact each other, and wherein at least one of the first portion and the second portion has at least one protrusion extending partially into the mold cavity; closing the compression mold and compressing the ground phyto material between the first portion and the second portion to form a phyto material tablet, wherein the phyto material tablet has at least one recess formed therein by the at least one protrusion, wherein the at least one recess extends partially from a top surface of the tablet to a bottom surface of the tablet and forms a region of structural weakness in the phyto material tablet whereby fracturing of the phyto material tablet is facilitated along the recess, and wherein the phyto material tablet has a greater exposed surface area after fracturing.

In accordance with an aspect of this disclosure, there is provided a method of forming a phyto material tablet comprising: a first extruder comprising a first diameter nozzle having a first diameter and fluidly coupled with a first mixing nozzle, the first extruder for extruding of a first portion of ground phyto material; loading the first portion of ground phyto material into a compression mold comprising a mold cavity formed from a first portion and a second portion together forming the mold cavity when the periphery of the first portion and the second portion contact each other, at least one of the first portion and the second portion having at least one protrusion extending partially into the mold cavity; closing the compression mold and compressing the ground phyto material between the first portion and the second portion to form a phyto material tablet, wherein the at least one protrusion forms a recess that extends partially into the phyto material tablet, wherein the recess defines a region of structural weakness in the phyto material tablet whereby fracturing of the phyto material tablet is facilitated along the recess, and wherein the phyto material tablet has an increased exposed surface area after fracturing.

In accordance with an aspect of this disclosure, there is provided a method of forming a phyto material tablet comprising: a first mixing nozzle having a mixing chamber and an output aperture; a first extruder comprising a first diameter nozzle having a first diameter and fluidly coupled with the first mixing nozzle, the first extruder for extruding of a first portion of ground phyto material; a second extruder comprising a second diameter nozzle having a second diameter and fluidly coupled with the first mixing nozzle, the second extruder for extruding of a second portion of liquid phyto material extract, the first mixing nozzle for receiving the first portion of ground phyto material and the second portion of liquid phyto material extract and mixing them within the mixing chamber to form a phyto material mixture, wherein the phyto material extract facilitates bonding of the ground phyto material; emitting the phyto material mixture from the output aperture into a mold cavity of a compression mold, wherein the mold cavity is formed from a first portion and a second portion, together forming the mold cavity when the periphery of the first portion and the second portion contact each other, at least one of the first portion and the second portion having at least one raised rib facing into the mold cavity; closing the compression mold and compressing the ground phyto material between the first portion and the second portion to form a phyto material tablet having at least one recess corresponding to the at least one raised rib, wherein the at least one recess extends partially through the tablet and defines a region of structural weakness in the phyto material tablet whereby fracturing of the phyto material tablet is facilitated along the recess, wherein the phyto material tablet has an increased exposed surface area after fracturing.

In some embodiments, the method may include opening the compression mold to separate the first portion and the second portion; ejecting the phyto material tablet from the compression mold using an ejector pin by imparting a force along one of the top surface and the bottom surface, the force being applied substantially across along an entirety of the one of the top surface and the bottom surface.

In some embodiments, the method may include coating the mold cavity with a ceramic coating to reduce an adhesion of the ground phyto material from the mold cavity for facilitating ejection of the phyto material tablet from the mold after compression.

In some embodiments, the method may include omitting a coating on the mold cavity, thereby forming the tablet in the absence of any lubricant.

In some embodiments, the method may include grinding phyto material to form ground phyto material having a predetermined particle size comprises filtering the ground material to remove ground phyto material particles having a particle size other than the predetermined particle size.

In accordance with an aspect of this disclosure, there is provided a method of forming a phyto material tablet comprising: grinding phyto material to form ground phyto material having a predetermined particle size; loading ground phyto material into a mold cavity of a compression mold, wherein the mold cavity is formed from a first portion and a second portion, together forming the mold cavity when the periphery of the first portion and the second portion contact each other, wherein at least one of the first portion and the second portion has at least one raised rib facing into the mold cavity; closing the compression mold and compressing the ground phyto material between the first portion and the second portion to form a phyto material tablet having a geometric shape corresponding to the shape of the cavity mold and having at least one recess molded into the phyto material tablet, wherein the at least one recess extends partially but not completely through the phyto material tablet, wherein the at least one recess defines a region of structural weakness in the phyto material tablet whereby fracturing of the phyto material tablet is facilitated at least along the recess.

In some embodiments, the ground phyto material comprises at least one of THC and CBD. In some embodiments, the ground phyto material comprises both THC and CBD.

In some embodiments, the method includes providing a grinder for grinding phyto material to form ground phyto material having a predetermined particle size.

In accordance with an aspect of this disclosure there is provided a system of providing a phyto material mixture, comprising: a first mixing nozzle having a mixing chamber and an output aperture; a first extruder comprising a first diameter nozzle having a first diameter and fluidly coupled with the first mixing nozzle, the first extruder for extruding a first portion of ground phyto material through the first diameter nozzle to the first mixing nozzle; a second extruder comprising a second diameter nozzle having a second diameter and fluidly coupled with the first mixing nozzle, the second extruder for extruding a second portion of liquid phyto material extract through the second diameter nozzle to the first mixing nozzle; wherein in a volumetric relationship the ratio of the second portion to the first portion is selected such that the phyto material extract forms a bond between the ground phyto material to enable the mixed ground phyto material and phyto material extract as a phyto material mixture to be emitted from the output aperture.

In some embodiments, the system may include a first heater for heating the first mixing nozzle to a first predetermined temperature, wherein the first predetermined temperature facilities a flow of the phyto material extract through the first mixing nozzle.

In some embodiments, the system may include a second heater for heating the first extruder to a second predetermined temperature, wherein the second predetermined temperature facilities a flow of the phyto material extract through the first extruder.

In some embodiments, the system may include a first container for containing the ground phyto material fluidly coupled with the first extruder for providing the ground phyto material thereto, wherein gravity assists feeding of the ground phyto material into the first extruder.

In some embodiments, the system may include a second container for containing the phyto material extract fluidly coupled with the second extruder for providing the phyto material extract thereto, wherein the second container is pressurized to assist feeding of the phyto material extract into the second extruder; a first fluid coupling between the second container and the second extruder, wherein the first fluid coupling comprises a first heater disposed about an outer diameter thereof for providing heat to the phyto material extract.

In accordance with an aspect of this disclosure there is provided a method of providing a phyto material mixture comprising: providing a first mixing nozzle having a mixing chamber and an output aperture; providing a first extruder comprising a first diameter nozzle having a first diameter and fluidly coupled with the first mixing nozzle; providing a second extruder comprising a second diameter nozzle having a second diameter and fluidly coupled with the first mixing nozzle; loading the first extruder with ground phyto material; loading the second extruder with liquid phyto material extract; extruding a first portion of ground phyto material into the mixing chamber; extruding a second portion of liquid phyto material extract into the mixing chamber; mixing of the first portion of ground phyto material with the second portion of liquid phyto material extract within the mixing chamber to form a phyto material mixture; extruding the phyto material mixture from the output aperture.

In some embodiments, the method may include varying a volumetric relationship of the second portion in relation to the first portion for having the phyto material extract to form a bond between the ground phyto material to allow the combination of the ground phyto material and phyto material extract as a phyto material mixture to form a three dimensional shape such that when the combination thereof is extruded from the mixing chamber output aperture the combination cools and allows the formation of the three dimensional shape as a phyto material mixture structure.

In some embodiments, the method may include measuring a first THC percentage of the ground phyto material; measuring a second THC percentage of the phyto material extract; measuring a third THC percentage of the phyto material mixture, wherein the first THC percentage is lower than the third THC percentage and the second THC percentage is higher than the third THC percentage.

It will be appreciated by a person skilled in the art that a tablet, apparatus or method disclosed herein may embody any one or more of the features contained herein and that the features may be used in any particular combination or sub-combination.

In some cases, a plurality of phyto material tablets may be provided within a container. The container can be configured as a blister package.

In some embodiments, terpenes may be added to the tablets while positioned within the blister package chambers, but prior to the tablets being sealed within the blister package chambers.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIG. 1A is a cut-away side view of an example phyto material forming assembly in accordance with an embodiment;

FIG. 1B is a cut-away side view of a mixing chamber of the forming assembly of FIG. 1A in accordance with an embodiment;

FIG. 1C is a schematic diagram of a system for forming phyto material using the forming assembly of FIG. 1A in accordance with an embodiment;

FIG. 3A is a bottom perspective view of a tablet forming apparatus in accordance with an embodiment;

FIG. 3B is a top perspective view of the tablet forming apparatus of FIG. 3A in accordance with an embodiment;

FIG. 3C is a perspective view of the tablet forming apparatus of FIG. 3A showing a compression mold closed in accordance with an embodiment;

FIG. 3D is a perspective view of the tablet forming apparatus of FIG. 3A illustrating a tablet positioned in the mold cavity following compression in accordance with an embodiment;

FIG. 3E is a perspective view of the tablet forming apparatus of FIG. 3A illustrating an example ejector mechanism in accordance with an embodiment;

FIG. 3F is a side view of the tablet forming apparatus of FIG. 3E in accordance with an embodiment;

FIG. 3G is a perspective view of a tablet being ejected from the tablet forming apparatus of FIG. 3A in accordance with an embodiment;

FIG. 5C is a cut-away side view of an example tablet dispensing apparatus for a vaporization device in accordance with an embodiment;

FIG. 5D is a top perspective of the example tablet dispensing apparatus of FIG. 5C in accordance with an embodiment;

FIG. 5E is a cut-away side view of another example tablet dispensing apparatus for a vaporization device in accordance with an embodiment;

FIG. 15F is a top perspective view of another example phyto material tablet in accordance with an embodiment;

FIG. 15G is a top view of another example heating chamber with the phyto material tablet of FIG. 15F in the heating chamber in accordance with an embodiment;

FIG. 15H is a top view of the heating chamber of FIG. 15E with another example phyto material tablet in the heating chamber in accordance with an embodiment;

FIG. 15I is a top view of another example heating chamber with the phyto material tablet of FIG. 15H in an inverted position in the heating chamber in accordance with an embodiment;

FIG. 15J is a top view of the heating chamber of FIG. 15I with the phyto material tablet of FIG. 15A in the heating chamber in accordance with an embodiment;

FIG. 15K is a top view of the heating chamber of FIG. 15I with the phyto material tablet of FIG. 15H in the heating chamber in accordance with an embodiment;

FIG. 16A illustrates an example plot of mixtures of THC and CBD obtainable in individual existing strains of cannabis;

FIG. 16B illustrates an example plot of mixtures of THC and CBD obtainable by combining multiple strains of cannabis.

Figure 2A:
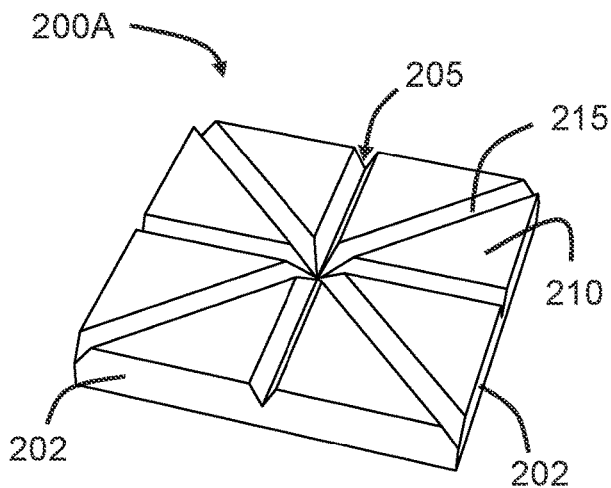
FIG. 2A is a top perspective view of an example phyto material tablet in accordance with an embodiment.
Figure 2B:
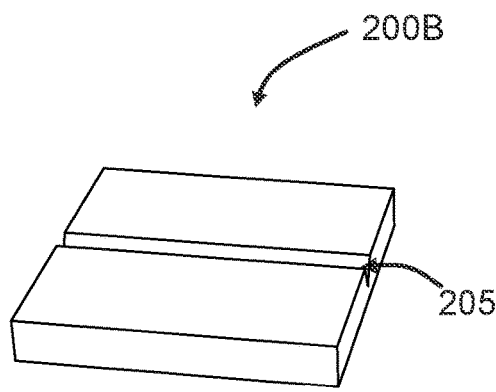
FIG. 2B is a top perspective view of another example phyto material tablet in accordance with an embodiment.
Figure 2C:
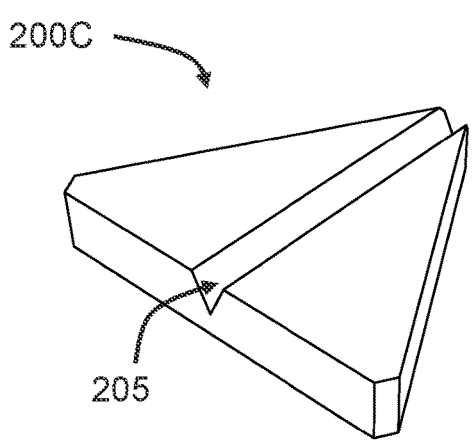
FIG. 2C is a top perspective view of another example phyto material tablet in accordance with an embodiment.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising," and variations thereof mean "including but not limited to," unless expressly specified otherwise. A listing of items does not imply that any or all of the items are mutually exclusive, unless expressly specified otherwise. The terms "a," "an," and "the" mean "one or more," unless expressly specified otherwise.

Embodiments described herein relate generally to vaporization of phyto materials. Various phyto materials derived from plant matter can be vaporized for aromatherapy or medicinal treatment regimens. For instance, phyto material from cannabis plants, such as the buds and/or leaves, may be vaporized. A user may inhale the cannabis vapor to achieve associated medicinal effects.

While interest in the therapeutic uses of phyto materials such as cannabis is growing, there are a number of challenges associated with its safe and effective use. These challenges include establishing dosing regimens, standardizing the potency and efficacy of cannabis products, and monitoring the use of cannabis by individual patients. These challenges also relate to the various forms in which cannabis can be delivered (e.g. ingestion, smoking, vaporizing). While vaporization of phyto materials avoids some of the deleterious side effects of smoking, there is often still uncertainty in the dose provided by vaporization due to variability in factors such as vaporization temperature, duration an amount of dose being consumed.

Phyto material products (e.g. loose leaf phyto material as well as extracts) may vary in potency from batch to batch, resulting in different experiences for the patient when consuming different batches of even the same phyto material product. Furthermore, the type or potency of phyto material product that a user consumes may vary over time, as their therapeutic needs change.

Controlling the dose provided to a user when vaporizing phyto materials such as cannabis products can be difficult. Often, users are provided with whole cannabis buds and instructed to manually prepare the buds for vaporization themselves. Thus, users may typically break or grind the cannabis products into suitably small pieces to facilitate vaporization. Depending on the type and size of the vaporization device used, users may inhale varying amounts of cannabis vapor in a session.

Given the uncertain quantity of cannabis product being consumed, it can be hard to track doses consumed by a user over time. Furthermore, the packing density of the phyto material in the heating chamber of a vaporization device can vary widely when end users insert loose phyto material into the vaporization devices. This may result in variance in the amount of the phyto material that is vaporized in a given vaporization session. For instance, in conduction vaporizers if the phyto material is too loosely packed, then sub-optimal vaporization may occur (e.g. it may take longer for the phyto material to be heated to a vaporization temperature).

To determine the amount of cannabis being inhaled, users may be required to weight the quantity of cannabis being loaded into a vaporization device. This process can be imprecise, in particular given the above-noted variance in vaporization quality. This process is also inconvenient and may require users to purchase additional equipment such as scales. This may be particularly undesirable for users who are in pain or experiencing other forms of illness or discomfort that is being treated by cannabis. Additionally, loading of the heating chamber can be a messy task and may result in a messy environment around the vaporization device.

Embodiments described herein may provide a vaporizable phyto material, such as a cannabis tablet. A vaporizable phyto material tablet may facilitate dose management for a user, by providing a known quantity of cannabis in an easily accessibly form factor. This may also reduce variance in how the phyto material is vaporized, by providing a consistent density of phyto material for vaporization. However, in some cases it may be difficult to ensure that all, or substantially all, of the cannabis in a tablet is easily vaporized.

Some previous systems have suggested manufacturing a compressed phyto material tablet with holes. For instance, PCT Publication NO. WO 2016/187695 A1 of Davis describes a tablet that is compressed using compression molds having at least one post or core to produce a through-hole in the compressed tablet. However, this manufacturing technique can result in the tablets being difficult to remove from the compression molds. Phyto material such as cannabis, and particularly buds from cannabis plants that contain the most THC and CBD, are known to be very sticky. Accordingly, the plant source material used to generate the compressed tablets may adhere to the compression molds. Furthermore, tablets with one or more holes can more easily fracture during manufacturing (e.g. during ejection from a compression mold), transport and loading into a heating chamber.

Embodiments described herein may provide a solid phyto material tablet. The solid phyto material tablet can be formed without any through holes.

In some embodiments described herein, the phyto material tablets may be fracturable or breakable into multiple pieces. This may facilitate vaporization of the phyto material tablet when positioned in a vaporization device.

Fracturing a phyto material tablet into multiple pieces can increase the surface area of the phyto material tablet available to be vaporized. Furthermore, this may ensure that the cannabis in the middle of the tablet can be vaporized. Accordingly, a greater proportion of the tablet may be vaporized. This may be particularly advantageous for vaporizers that use convection-based heating in which heated air is used to heat the phyto material tablet.

Forming a substantially solid phyto material tablet may also reduce or avoid manufacturing difficulties associated with the tablet sticking to the mold. A substantially solid phyto material tablet may also provide a more robust product for transportation. This additional robustness may also facilitate handling by an end user.

In some embodiments, the phyto material tablet can be manufactured of partially ground cannabis material. For instance, the cannabis material may initially be ground to have a substantially consistent particle size. Optionally, the cannabis material may also be filtered to provide the consistent particle size. In some cases, stems and other unwanted parts may be removed by filtering. The ground cannabis material may then be formed into a phyto material tablet, e.g. using a compression mold. The compression mold may shape the phyto material tablet as a substantially solid phyto material tablet or puck or pellet (e.g. a tablet that does not include any through holes).

In some cases, the phyto material tablet may be formed with one or more break regions. The break regions may facilitate breaking or fracturing the phyto material tablet into multiple pieces. The break regions may be regions of reduced strength or structural integrity so the tablet will fracture more easily in these break regions than in other regions of the phyto material tablet. This may facilitate separating the tablet into multiple pieces for vaporization. The compression mold used to form the phyto material tablets may be shaped to define break regions in the surface of the phyto material tablet.

In some embodiments, the phyto material tablet can be formed with one or more lines of weakness. The lines of weakness may then define the break regions. For example, the phyto material tablets may be formed with areas of reduced thickness or width (e.g. depressions/recess) that may be shaped into lines. These regions of reduced thickness may define the lines of weakness. This may facilitate breaking the phyto material tablet along the lines of weakness in response to an applied force.

The phyto material tablets may be formed with break regions arranged into a break pattern. For instance, the lines of weakness may form a pattern on a surface of the phyto material tablet to allow the tablet to break into multiple pieces corresponding to the defined pattern. The break regions may be arranged across the phyto material tablet so that the tablet separates into pieces having substantially similar sizes.

The phyto material tablets may be formed into various shapes. For example, the tablets may be formed into substantially symmetrical shapes, such as circular shapes, some triangular shapes, and regular polygon shapes. In some cases, the tablets may be formed into asymmetrical shapes. Optionally, this may enable registration of the tablets within a vaporization device. Registering the orientation of the tablet within a vaporization device may ensure that the vaporization device can fracture the tablet properly along the break regions.

In some cases, the phyto material tablets may be formed with orientation markers. In some cases, the phyto material tablets may be shaped to include one or more orientation markers. For example, one or more notches or recesses may be formed in the surface of the phyto material tablet. The notches or recesses may be formed with an asymmetric pattern that provides a visual identification of the orientation of the phyto material tablet.

In some cases, an orientation marker may be provided on an outer surface of the phyto material tablet. For example, a visual identifier may be provided on a top or bottom surface indicating that the surface is the top or bottom of the tablet (e.g. a 'T' printed or embossed on the top surface and/or a 'B' printed or embossed on the bottom surface). The visual identifier may be provided in many forms, for instance providing varying colors across the outer surface of the phyto material tablet.

Embodiments described herein may also provide a vaporization device for a phyto material tablet. In some cases, the vaporization device may include tablet fracturing components that can be used to fracture phyto material tablets inserted into the vaporization device. In some cases, the vaporization device may be used with phyto material tablets having break regions.

The vaporization device may define a vaporization chamber or heating chamber within which a phyto material tablet can be received. The heating chamber may be configured to encourage vaporization of the phyto material tablet. In some cases, one or more portions of the heating chamber can include protrusions or projecting members that extend into the cavity of the heating chamber. The projecting members may apply force to a phyto material tablet positioned in the chamber cavity. This may serve to compress the tablet, and may encourage fracturing.

In some cases, the vaporization chamber may include a tablet fracturing element. For instance, a projecting member may be configured to provide a tablet fracturing element. In some cases, at least one inner surface of the vaporization chamber may have a fracturing surface region. The fracturing surface region may be shaped or arranged to fracture a phyto material tablet positioned in the tablet region.

In some cases, multiple surfaces of the vaporization chamber may include fracturing regions. For instance, opposing surfaces of the vaporization chamber (e.g. the lid and base) may each be formed with one or more fracturing regions. These regions may concurrently apply force to opposing sides of a phyto material tablet to cause the tablet to break into multiple pieces.

For example, the vaporization chamber may include a lid that is used to enclose the phyto material tablet within the chamber. The lid may be moveable between an open position, in which a user is provided access to the vaporization chamber, and a closed position, in which the chamber is enclosed to define a vaporization oven. The lid may include a projection or projecting member that can be configured as a compression member and/or fracturing surface region. The fracturing surface region may apply a force to the phyto material tablet in the tablet region to fracture or break the phyto material tablet into multiple pieces.

For example, when the lid is moved to the closed position the fracturing surface region may contact the phyto material tablet and apply a force to the phyto material tablet. When the vaporization tablet is configured with a fracturing surface region, the force applied to the phyto material tablet may be applied irregularly across the surface of the phyto material tablet to encourage the tablet to break into multiple pieces.

Additionally or alternatively, the fracturing surface region may be provided by other surfaces of the vaporization chamber. For example, a bottom surface of the vaporization chamber may include a fracturing surface region. The phyto material tablet may then be pushed into the bottom surface of the vaporization chamber. This may induce the tablet to break into multiple pieces because of the irregular force applied on the tablet by the fracturing surface region on the bottom surface of the vaporization chamber. For instance, closing the lid of the vaporization chamber may push the tablet into the bottom surface of the chamber.

Various forms of fracturing surface regions may be used. For instance, the inner surface of the vaporization chamber may have a non-planar surface profile. For instance, the surface profile of at least one inner surface of the vaporization chamber may be irregular or uneven. In other cases, the surface profile may define regular patterns such as a curve or pyramid and/or may have multiple protruding regions.

In some cases, the surface that includes the fracturing surface region may be moveable. For instance, the vaporization device may include a plunger that pushes the phyto material tablet into the vaporization chamber. The plunger may extend into the tablet region to cause the tablet to contact the opposing surface of the vaporization chamber. The plunger may continue to extend into the tablet region (at least temporarily) after the phyto material tablet has contacted the opposing surface to apply a force on the tablet to induce it to fracture.

Various examples of vaporization devices may be described herein that can be used to vaporize a phyto material tablet that is fractured into multiple pieces. In some cases, these vaporization devices may be used in combination with phyto material tablets that are shaped to define regions of weakness. This may further facilitate fracturing the tablet into multiple pieces for improved vaporization. In some cases, however, the vaporization devices described herein may be used with other phyto material tablets or other vaporizable cannabis products. Similarly, embodiments of the phyto material tablets described herein may be used with vaporization devices other than the example devices described herein.

In some cases, the phyto material tablets described herein may be configured to increase the surface area for vaporization even in the absence of fracturing. The tablets may be configured to flex or compress when inserted into a vaporization device. For instance, the tablets may expand to contact the surfaces of a vaporizer heating chamber when the chamber lid is closed or when a plunger pushes the tablet into the chamber. This may allow an increased surface area of the tablet to contact the surfaces of the heating chamber to facilitate vaporization.

In some cases, the vaporization devices described herein may be configured to increase the surface area of the phyto material tablets that are exposed to heat for vaporization even in the absence of fracturing. The vaporization devices may include a plurality of heating elements usable to heat different sides of a phyto material tablet positioned in a heating chamber. For instance, two or more of the heating chamber base, heating chamber side, and heating chamber lid may include a heating element operable to heat a phyto material tablet. This may allow an increased surface area of the tablet to contact the heating elements of the heating chamber to facilitate vaporization.

In some cases, the vaporization devices may also include a vapor inlet that extends into the heating chamber. The vapor inlet may be shaped to increase a vapor inlet area, e.g. using a curved vapor inlet. This may further facilitate drawing air through the heating chamber, and in turn drawing vapor towards the inhalation aperture.

Furthermore, various examples of processes for manufacturing phyto material tablets are described. The phyto material tablets described herein may include phyto material tablets manufactured according to the example processes described herein, as well as tablets formed using other methods.

Phyto Material Tablet

The following is a general description of a phyto material tablet that may be used by itself or in combination with one or more aspects of the disclosure herein, including a vaporizer for a phyto material tablet and/or a method of forming a phyto material tablet. The following description contains various features of a phyto material tablet that may be used individually or in any combination or sub-combination.

Referring to FIGS. 2A to 2F, various examples of phyto material tablets 200 (e.g. phyto material tablets) are illustrated. The phyto material tablets 200 shown in FIGS. 2A-2F illustrate various geometric shapes of phyto material tablets, such as square tablets 200a and 200b, triangular tablets 200c, circular tablets 200d, pentagonal tablets 200e and various other shapes of tablets such as half circle square tablets 200f, although it should be understood that various other shapes may also be used such as other polygonal shapes and various irregular shapes for example. Providing the tablets 200 with a flat side surface, as shown in FIGS. 2A-2C and 2E-2F may also facilitate pushing the tablets 200 with a consistent force to translate them laterally, while also potentially avoiding undesired fracturing.

Each phyto material tablet 200 may be formed using a pre-defined dose of phyto material. The pre-defined dose of phyto material may be formed including using homogenized phyto material. The homogenized phyto material may be configured to include a plurality of different types of phyto material (e.g. different strains of cannabis) that have been mixed to provide a consistent mixture of ground phyto material.

Having a phyto material tablet 200 with a defined dose quantity may facilitate dose management for users of the phyto material tablets 200. For example, a phyto material tablet 200 may be shaped using 0.1 g of phyto material. This may allow a user to easily consume an appropriate dose when vaporizing the phyto material tablet 200. The phyto material tablets 200 may be formed using different quantities of phyto material depending on the desired dose to be delivered. For example, phyto material tablets 200 may be formed using 0.2 g of phyto material, 0.3 g of phyto material, 0.4 g of phyto material, 0.5 g of phyto material, 0.6 g of phyto material, 0.7 g of phyto material, 0.8 g of phyto material, 0.9 g of phyto material, and/or 1 g. A more granular range of phyto material tablets may also be provided, e.g. using, 0.11 g, 0.12 g, 0.13 g, 0.14 g, 0.15 g, 0.16 g, 0.17 g, 0.18 g, 0.19 g, 0.2 g etc. of phyto material.

The size of the phyto material tablets 200 may also vary. For instance, the size may vary based on the dose being provided. In some cases, the size of the phyto material tablets 200 may also vary to accommodate different vaporization devices. For example, the phyto material tablets may be formed to be, 5 mm, 6 mm, 7 mm, 8 mm, 9 mm, 10 mm, 11 mm, 12 mm, 13 mm, 14 mm, 15 mm, 16 m, 17 mm, 18 mm, 19 mm, and/or 20 mm along its longest axis. The thickness of the phyto material tablets 800 may also vary. For example, the tablets 800 may be formed with a thickness of 1 mm, 2 mm, 3 mm, 4 mm, 5 mm, 6 mm, 7 mm, and/or 8 mm in various examples. For example, phyto material tablet 200a formed from pressed cannabis (phyto material) may be provided with dimensions of approximately 14 mm diameter (or another shape)×2 to 5 mm thickness. In some embodiments, tablets that are cylindrical in shape may have a diameter of about 10 mm-10.5 mm and a thickness of about 3.5 mm-4 mm. In a preferred embodiment, a cylindrical tablet may have a diameter that is about three times its thickness.

The dimensions of the phyto material tablet may vary depending on how the phyto material tablet is distributed and inserted into a vaporization device. For instance, where the phyto material tablet is stored in a blister package, the ratio of the tablet thickness or height to the tablet width may be selected to increase the structural integrity of the tablet and prevent fracturing or breakage during removal from the packaging. In other cases, the tablet may be provided with a lower ratio of tablet thickness to tablet width, for instance where a plurality of tablets are positioned within a dispensing apparatus that is inserted or insertable within a vaporization device.

Figure 2D:
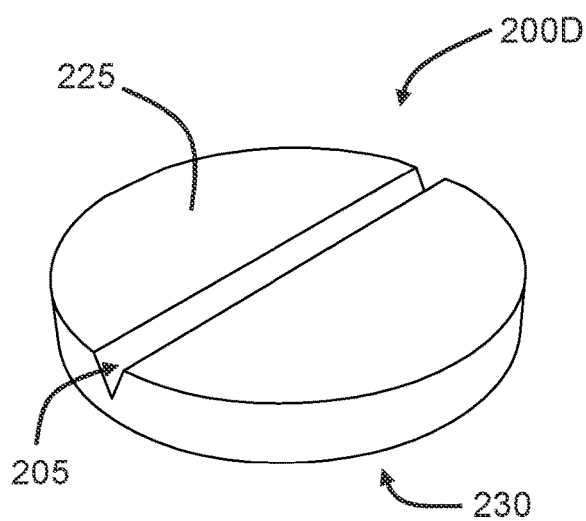
FIG. 2D is a top perspective view of another example phyto material tablet in accordance with an embodiment.
Figure 2E:
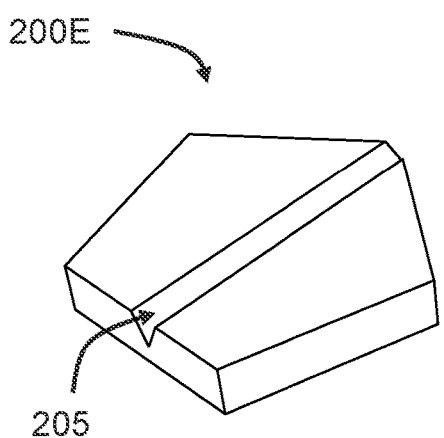
FIG. 2E is a top perspective view of another example phyto material tablet in accordance with an embodiment.
Figure 2F:
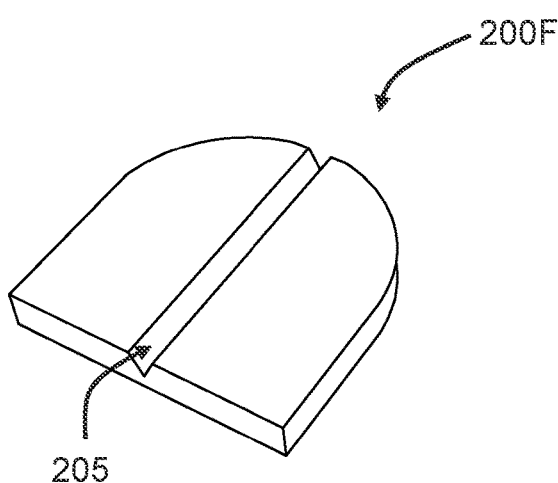
FIG. 2F is a top perspective view of another example phyto material tablet in accordance with an embodiment.
Figure 2G:
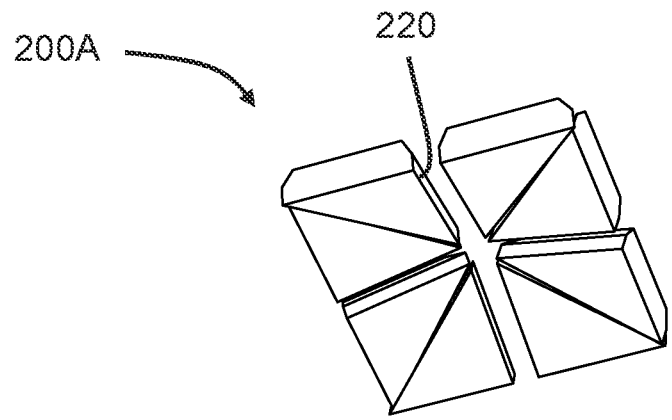
FIG. 2G is a bottom perspective view of the example phyto material tablet of FIG. 2A broken into multiple pieces in accordance with an embodiment.
Figure 2H:
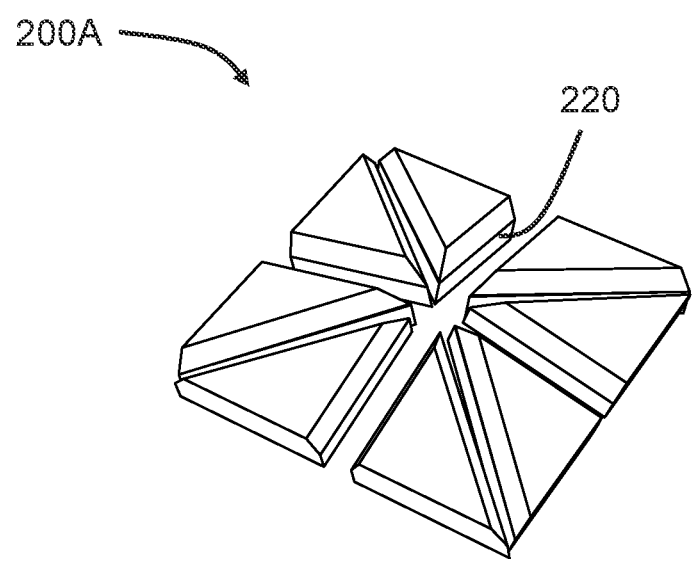
FIG. 2H is a top perspective view of the example phyto material tablet of FIG. 2A broken into multiple pieces in accordance with an embodiment.

As shown in FIGS. 2A-2F, the tablets 200 may include break regions 205. The break regions 205 may be formed as recesses 215 in the surface 210 of the tablets 200. By selectively applying a force to opposing sides of a break region, the tablets 200 may be fractured into multiple pieces. FIGS. 2G and 2H illustrate an example of tablet 200a after being fractured along recessed ribs 215.

When formed, the tablets 200 have a first or initial exposed surface area. This initial exposed surface area refers to the outer surface 210 of the tablet 200 that may contact surrounding air. This outer surface 210 may be heated directly by an externally applied heat or heated air. Following fracturing, the tablets 200 have a second exposed surface area that is greater than the initial exposed surface area. This allows a greater proportion of the tablet 200 to be heated directly by contact with a heating surface or heated air.

Once the tablet is fractured, the exposed surface area of the tablet is increased. For instance, as shown in FIGS. 2G and 2H surface regions 220 that previously were not exposed are exposed following fracturing of the tablet 200A. Prior to fracturing, the surface regions 220 were within the solid phyto material tablet 200A. Following fracturing, the surface regions 220 are now exposed to provide an increase in net surface area of the phyto material tablet, or the surface area that contacts the air.

The phyto material tablets 200 may be formed of compressed cannabis material. The cannabis material may be ground prior to compression. The coarseness of the ground cannabis material may be adjusted to increase or decrease the airflow through the tablets 200. The coarseness can similarly be selected to provide a sufficiently dense tablet 200 to provide structural integrity and a desired size/quantity of dose.

In some embodiments, the pressure applied when forming the phyto material tablets 200 may be adjusted to increase or decrease the airflow through the tablets 200. In turn, this may increase or decrease the conduction of heat through the tablets 200. Accordingly, the specified pressure used may vary depending on the type of vaporization device for which the phyto material tablets are intended.

In some cases, the phyto material may also be combined with other plant-derived products. For instance, cannabis resin may be mixed with the phyto material. In other cases, products such as Nicotine, CBD and other extracts, or phyto material from different plants may be mixed together. This may allow greater control of the dose provided by tablets 200. Optionally, the resin found within the cannabis used to form the tablet can be used as the binding agent. Accordingly, additional resin may not be required.

Cannabis plants, and in particular female cannabis plants include a plurality of different phyto material components including phyto cannabinoids, such as Cannabidiol (CBD)

and Tetrahydrocannabinol (THC), as well as flavonoids and terpenes. The various phyto material components in a cannabis plant may have different therapeutic properties. Phyto material tablets described herein may be configured to have a combination of phyto cannabinoids. In some cases, the phyto material tablets may be configured to combine phyto cannabinoids with other components, such as flavonoids and/or terpenes.

Phyto cannabinoid may occur in various forms, such as acid forms and non-acid forms. For example, THC may have an acid form of tetrahydrocannabiniolic acid that is indicated as THCa, while the decarboxylated form is indicated simply as THC. When phyto material products are used in vaporization devices, the acid form of phyto cannabinoids may undergo decarboxylation due to the heat applied by the device. As a result, THCa may be decarboxylated into THC.

Cannabis plants can include a variety of different phyto cannabinoids, such as: cannabidiol, represented as CBDa in acid form or CBD in decarboxylated form; cannabichromene, represented as CBCa in acid form or CBC in decarboxylated form; cannabigerol, represented as CBGa in acid form or CBG in decarboxylated form; tetrahydrocannabivarin, represented as THCVa in acid form or THCV in decarboxylated form; cannabidivarin, represented as CBDVa in acid form or CBDV in decarboxylated form; and cannabinol, represented as CBNa in acid form or CBN in decarboxylated form.

Terpenes are aromatic metabolites typically found in plant oils. Terpenes may act as both a defense mechanism and pollinator attractant for the plants. Cannabis plants produce more than one hundred different terpenes. Each type of terpene may provide different therapeutic properties, such as differing aromatic characteristics.

Phyto cannabinoids and terpenes may be processed in the same biosynthesis pathways. Terpenes may provide entourage effects when combined with phyto cannabinoids. The terpenes may assist the expression of the phyto cannabinoids when consumed by a user. In some cases, terpenes may enhance desirable effects of phyto cannabinoids. In some cases, terpenes may moderate adverse effects of other phyto cannabinoids. By controlling the quantities, and relative quantities, of phyto cannabinoids and terpenes in each phyto material tablet, the therapeutic effects of the phyto material tablets can be controlled for a user. This may facilitate providing a user with a controlled dose, based on the desired therapeutic effects.

A variety of different terpenes may be used with phyto material tablets. For example, Pinene is one example of a terpene that may be used in phyto material tablets. Pinene may provide an aroma of pine, and may also be found in other naturally occurring products such as pine needles, rosemary, and basil. When consumed, Pinene may assist in increasing a user's alertness and may moderate some side effects of THC, such as short-term memory loss. Pinene may also provide anti-inflammatory benefits and may help improve airflow into a user's lungs.

Caryophyllene is another example of a terpene that may be used in phyto material tablets. Caryophyllene may provide a spicy and woody aroma, and may also be found in other naturally occurring products such as cloves, black pepper, cinnamon leaves, and Thai basils. When consumed, Caryophyllene may assist in relieving stress and acting as an anti-inflammatory.

Humulene is another example of a terpene that may be used in phyto material tablets. Humulene may provide a spicy and woody aroma, and may also be found in other naturally occurring products such as coriander, hops, cloves, and basil. When consumed, Humulene may assist in suppressing appetite and acting as an anti-inflammatory.

Limonene is another example of a terpene that may be used in phyto material tablets. Limonene can often be found in Sativa-dominant strains of cannabis, which may contain greater than 0.5% Limonene. Limonene may provide a citrus aroma, and may also be found in other naturally occurring products such as rosemary, juniper, peppermint, and rinds of citrus fruits. When consumed, Limonene may assist in relieving stress and elevating mood. Limonene may also provide antifungal and antibacterial properties.

Linalool is another example of a terpene that may be used in phyto material tablets. Linalool may provide a floral aroma, and may also be found in other naturally occurring products such as coriander and lavender. When consumed, Linalool may assist in relieving stress, enhancing mood, and providing sedating effects. Linalool may also act as an anti-inflammatory. Linalool may assist in moderating side effects of THC that can contribute to anxiety.

Myrcene is another example of a terpene that may be used in phyto material tablets. Myrcene occurs frequently in cannabis plants, and can often be found in Indica-dominant strains of cannabis, which may contain greater than 0.5% Myrcene. Myrcene may provide an earthy aroma, and may also be found in other naturally occurring products such as mango, hops, thyme, basil and lemongrass. When consumed, Myrcene may provide muscle relaxant and sedating effects and may act as an anti-inflammatory.

Ocimene is another example of a terpene that may be used in phyto material tablets. Ocimene may provide a sweet herbal aroma, and may also be found in other naturally occurring products such as mint, mangoes, parsley, and pepper.

Terpinolene is another example of a terpene that may be used in phyto material tablets. Terpinolene may provide a slight pine aroma, and may also be found in other naturally occurring products such as nutmeg, tea tree, apples, cumin, sage, rosemary and lilac. When consumed, Terpinolene may provide relaxing effects that may be sedating and may reduce anxiety or excitement.

In some cases, a phyto material tablet may be formed with a single layer of phyto material. In other cases, phyto material tablets may include multiple layers, where each layer includes a different combination of active components. In some embodiments, the tablets may be formed with two or stratified layers.

The tablet may be formed with the layers sequentially compressed on top of one another to define the stratified layers of the tablet. A first layer can be deposited and compressed to form the first tablet layer and a subsequent layer can be deposited on the first tablet layer and subsequently compressed to form a combined multi-layer tablet. This process may be repeated for a plurality of layers.

In some cases, additional components, such as resin binders, may be deposited between the layers of compressed phyto material. In some cases, other components such as terpenes may be included in the tablet, e.g. deposited on a layer or on the outer surface of the tablet. In some cases, components such as oils or extracts may be deposited between layers and then contained between the layers of phyto material. This may provide a tablet with an enclosed oil or extract portion.

For example, a coating of flavonoids and/or terpenes may be deposited on one or more surfaces of the phyto material tablet. In some cases, the coating may be deposited on a particular surface of the tablet, such as the bottom surface.

This may encourage the components of the coating to be vaporized and consumed first by a user.

In some cases, the tablets can also be formed with an orientation marker. This may ensure that a user inserts the tablet into a heating chamber with the correct orientation. For example, the orientation marker may include an asymmetric shape. The tablets may include one or more notches or recesses that are asymmetrically arranged to provide an orientation marker (see e.g. FIG. 7N). In other cases, a visual orientation marker may be provided on a top or bottom surface of the tablet (see e.g. FIG. 7P).

The phyto material tablets 200 may be compressed to a sufficiently dense and hard form to resist breakage during handling prior to insertion into a vaporization device. The tablets 200 may retain a substantially rigid shape yet allow for being fractured inside the heating chamber of a vaporization device. In some cases, the tablets 200 may be fractured by applying a variable pressure across the surface 210. In some cases, the tablet 200 may be partially heated to facilitate fracturing.

In some cases, the phyto material tablets 200 can be compressed to a sufficiently rigid form to enable puncturing through a blister pack when being removed. In some cases, the phyto material tablets 200 can be compressed to a sufficiently rigid form to enable being housed in a dispensing magazine within a vaporization device.

The shapes of the tablets 200 may also be selected to increase the exposed surface area. For instance, the lateral sides 202 of the tablets may be formed with indents (see e.g. FIGS. 7A-7F) to increase the area exposed to air flow. This may ensure that the tablets 200 may still be suitably vaporized if there is a failure to fracture properly.

In some cases, the sides of the tablets may include one or more vertically extending recess. These recesses may provide airflow channels to allow heated air to contact an increased surface of the tablets. The recesses may also facilitate airflow past the tablets, to allow a user to inhale vapor more easily. In some cases, the recesses may be aligned with corresponding shapes in a vaporization chamber to increase the surface area of the tablet that contact a conduction heater that may be provided by the sides of the chamber.

The recesses may also facilitate removal of the tablet from a heating chamber. For example, where the tablet does not fracture or does not substantially fracture upon vaporization, the recesses may be used to grasp the tablets (e.g. using a tool such as a pick) for removal from the heating chamber. In some cases, the recesses may also provide orientation and/or registrations markers for the phyto material tablets.

Figure 7A:
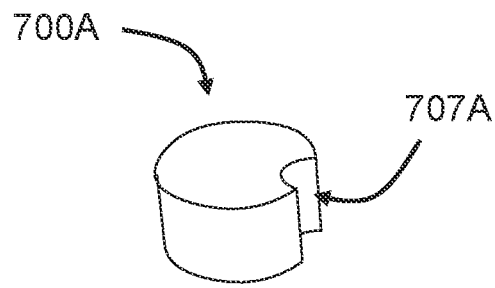
FIG. 7A is a top perspective view of another example phyto material tablet in accordance with an embodiment.
Figure 7B:
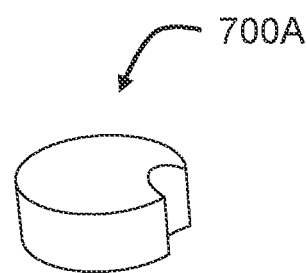
FIG. 7B is another top perspective view of the example phyto material tablet of FIG. 7A.

FIGS. 7A-7F illustrates examples of tablets 700A-700C having recesses 707 formed therein. As shown in FIGS. 7A and 7B, the tablet 700A includes a single recess or notch 707A. In addition to increasing exposed surface and/or providing airflow channels, the recess 707A may also be used to align the tablet 700A within a vaporization chamber. In the example shown, the recess 707A is semi-circular in shape, although alternative shapes may be used for the recess such as triangular and/or rectangular notches.

Figure 7C:
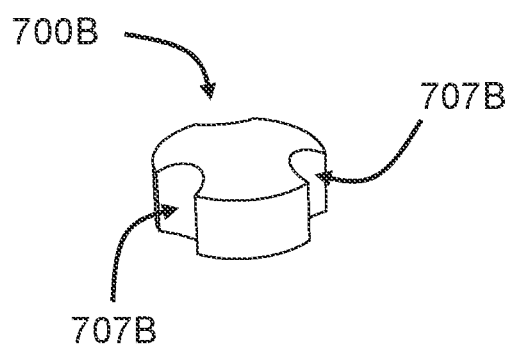
FIG. 7C is a top perspective view of another example phyto material tablet in accordance with an embodiment.
Figure 7D:
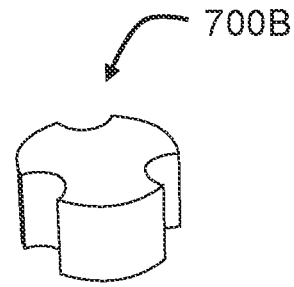
FIG. 7D is another top perspective view of the example phyto material tablet of FIG. 7C.
Figure 7E:
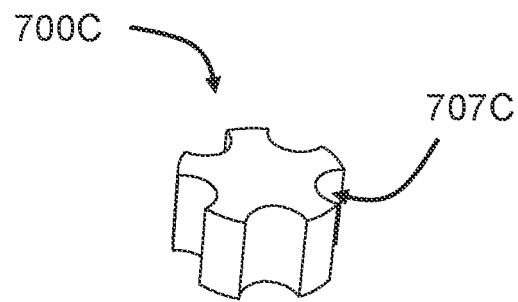
FIG. 7E is a top perspective view of another example phyto material tablet in accordance with an embodiment.
Figure 7F:
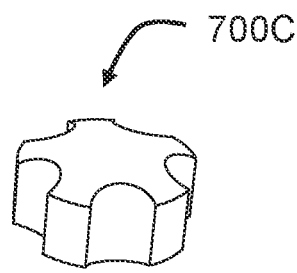
FIG. 7F is another top perspective view of the example phyto material tablet of FIG. 7E.

FIGS. 7C and 7D illustrate an example of a tablet 700B that includes a plurality of recesses 707B. In the example shown, tablet 700B includes three recesses 707B. FIGS. 7E and 7F illustrate another example of a tablet 700C with a plurality of recesses 707C. In the example shown, tablet 700C includes five recesses 707C. The shapes of tablets 700 may also vary, as with tablets 200A-200F described herein above.

In various examples, one or both of the top surface 225/725 and bottom surface 230/730 of a tablet 200/700 may be non-planar. For instance, the top surface 225/725 and/or bottom surface 230/730 may be curved. This may reduce contact between adjacent tablets 200/700 in a container, which may prevent tablets 200/700 from fracturing during transport.

Figure 7G:
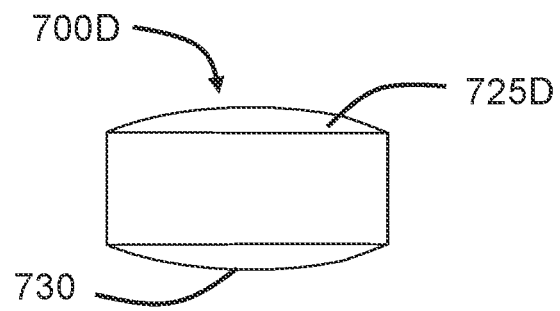
FIG. 7G is a side view of an example phyto material tablet in accordance with an embodiment.

FIG. 7G illustrates a side profile of another example tablet 700D. Tablet 700D has a non-planar (here shown as convex curved) upper surface 725D. Tablet 700D also has a non-planar bottom surface 730.

Figure 7H:
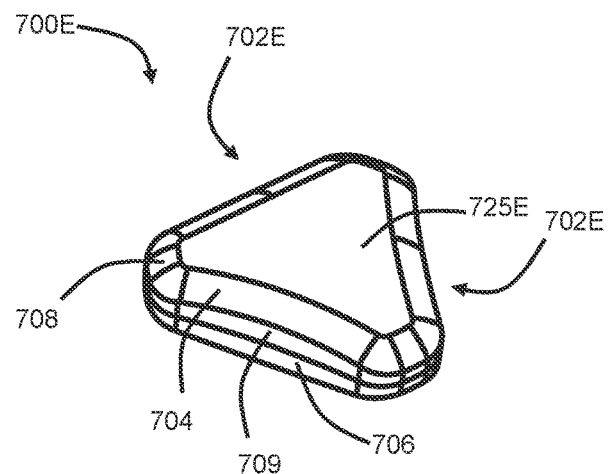
FIG. 7H is a top perspective view of another example phyto material tablet in accordance with an embodiment.

FIG. 7H illustrates another example of a tablet 700E. Tablet 700E is generally shaped as a triangular prism. The upper surface 725E and lower surface (not shown) of tablet 700E are generally triangular in shape.

The sides 702E of tablet 700E are shaped into multiple sections. An upper section 704 of each side 702E is outwardly angled from the top surface 725E. A lower section 706 is outwardly angled from the bottom surface of tablet 700E. In some cases, the upper section 704 and lower section 706 may meet at a vertex. In other cases, as shown, an intermediate side section 709 may extend between the upper section 704 and lower section 706. The intermediate side section 709 may be generally vertical (e.g. perpendicular to a top or bottom surface plane of tablet 700E). The corners 708 of tablet 700E are also outwardly angled from the top surface 725E and bottom surface of the tablet 700E.

In some cases, a phyto material tablet may be formed with a variable density. For example, the density of a phyto material tablet may increase gradually from a first side of the tablet to a second, opposing side, of the tablet. By positioning the less densely packed portion of a tablet proximate a vapor inlet of a vaporization device, the flow of air therethrough may be promoted.

In some cases, the region of reduced density may be identified by a recess 707A in the tablet 700. For example, the portion of tablet 700A proximate the recess 707A may be less densely packed than the other side of the tablet 700A opposite the recess 707A. This may facilitate alignment of the less densely packed region with a vapor inlet.

Figure 7I:
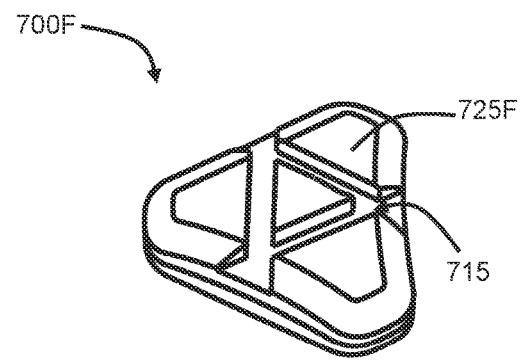
FIG. 7I is another top perspective view of a variant of the example phyto material tablet of FIG. 7H.

FIG. 7I illustrates another example of a phyto material tablet 700F. Phyto material tablet 700F has a generally triangular shape similar to phyto material tablet 700E. However, in tablet 700F, recesses 715 are formed in the top surface 725F. In some cases, recesses may also be formed in the bottom surface of tablet 700F.

The recesses 715 may provide airflow channels along the surface of tablet 700F. This may facilitate convective heating of the tablet 700F. This may also facilitate airflow through a heating chamber in which the tablet 700F is positioned. In some cases, the recesses 715 may be configured to define break regions within tablet 700F to encourage tablet 700F to fracture into multiple pieces.

Figure 7J:
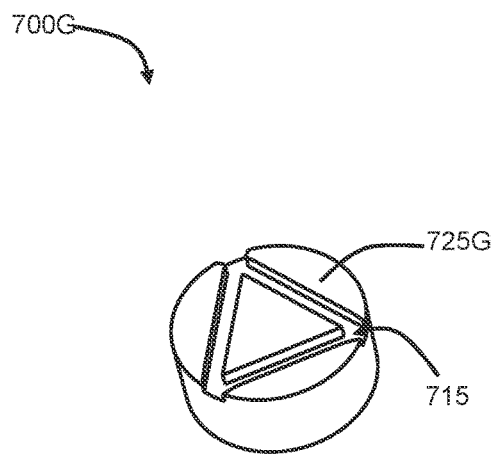
FIG. 7J is a top perspective view of another example phyto material tablet in accordance with an embodiment.

FIG. 7J illustrates another example tablet 700G. Tablet 700G has a generally circular profile with smooth sidewalls. Tablet 700G also includes recesses 715 formed in the top surface 725G. In some cases, recesses may also be formed in the bottom surface of tablet 700G (not shown). The recesses 715 may facilitate air flow over the top surface 725G. In some cases, the recesses 715 may also facilitate fracturing of tablet 700G.

Figure 7K:
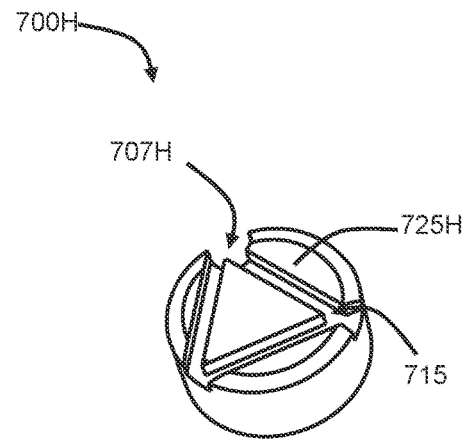
FIG. 7K is a top perspective view of another example phyto material tablet in accordance with an embodiment.

FIG. 7K illustrates another example of a phyto material tablet 700G. Phyto material tablet 700H is generally similar to tablet 700G in that phyto material tablet 700H has recesses 715 formed in the top surface 725H (and possibly the bottom surface as well). Phyto material tablet 700H also includes a notch or recessed section 707H in the sidewall.

Figure 7L:
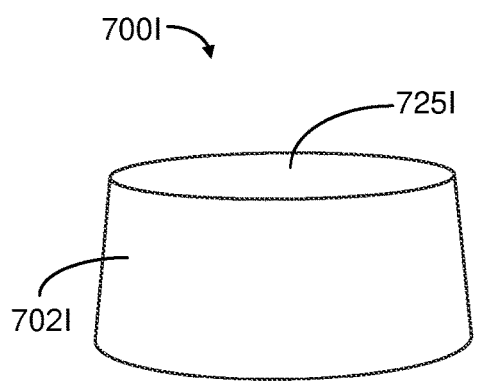
FIG. 7L is a side perspective view of another example phyto material tablet in accordance with an embodiment.
Figure 7M:
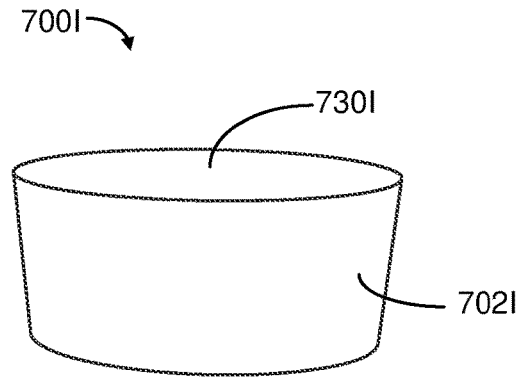
FIG. 7M is a side perspective view of the phyto material tablet of FIG. 7L in an inverted position in accordance with an embodiment.

FIGS. 7L and 7M illustrate another example of a phyto material tablet 700I. Phyto material tablet 700I is an example of a phyto material tablet with a top surface 725I that has a smaller surface area than its bottom surface 730I. The relative sizes of the top and bottom surfaces may be defined to provide an orientation marker, indicating an insertion orientation for the vaporization device.

For example, the tablet 700I may be formed with a plurality of different layers of phyto materials and/or coatings on surface portions. It may thus be desirable for a particular portion of the tablet 700I to be vaporized initially.

For example, the bottom surface of the tablet 700I may be infused with components such as terpenes. The components may be deposited onto the bottom surface, for example after the tablet 700I has been compressed. The deposited components may permeate into the tablet 700I through capillary action. This may provide a distribution of the deposited components that is greater proximate the bottom surface and decreases with progression into the body of the tablet.

By providing an orientation marker, a user can visually determine the appropriate orientation for the tablet to be inserted into the vaporizer. The user may then be able to position the surface having the greater concentration of the deposited components in contact with a heated surface of the vaporizer. The surface having the majority of the infused components (e.g. terpenes) will tend to vaporize more rapidly given its proximity to the heater (and also possibly due to a lower vaporization temperature for the deposited components) and enter as vapor inhaled by a user earlier.

Depositing components such as terpenes on an outer surface of the tablet may facilitate uptake of other components vaporized in the tablet, such as THC and/or CBD. Terpenes that are present in the vapor initially consumed by a user may prepare the user's endocannabinoid system for reception of the THC/CBD and may help to enhance the associated therapeutic benefits.

Figure 7N:
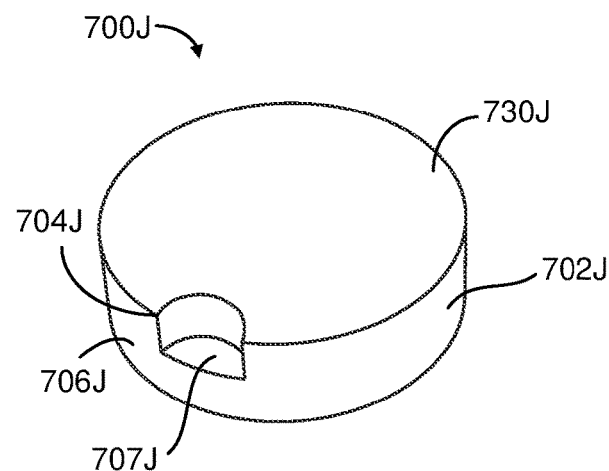
FIG. 7N is a top perspective view of another example phyto material tablet in accordance with an embodiment.

FIG. 7N illustrates another example of a phyto material tablet 700J. Phyto material tablet 700J is a generally cylindrical phyto material tablet. As shown in FIG. 7N, the tablet 700J includes a notch or recessed section 707K in the sidewall 702J. However, the recessed section 707K does not extend along the entire height of the sidewall 702J. Rather, the recessed section 707K is only provided in a lower portion 704K of the sidewall 706K proximate the bottom surface 730J (or an upper portion proximate the top surface in other embodiments).

The recessed section 707K may provide an orientation indicator for the tablet 700J. A user may identify the bottom surface of tablet 700J by the notch 707K, while identifying the top surface of the tablet 700J by the absence of a notch (or vice versa).

In some cases, the lower portion 704K of the tablet 700J may be formed using a different combination of phyto material components from the lower section 706K. The recessed section 707k can be positioned to correspond to one of those sections. This may ensure that a user positions the correct section at the base of the heating chamber, for instance where the phyto material tablet 700J is configured with portions 704/706 having phyto material components intended to be vaporized partially sequentially within a vaporization session. When a user inserts the tablet into the vaporization device and vaporizes the tablet, this may increase the likelihood of the components of the tablet being vaporized in the correct sequence.

Figure 7O:
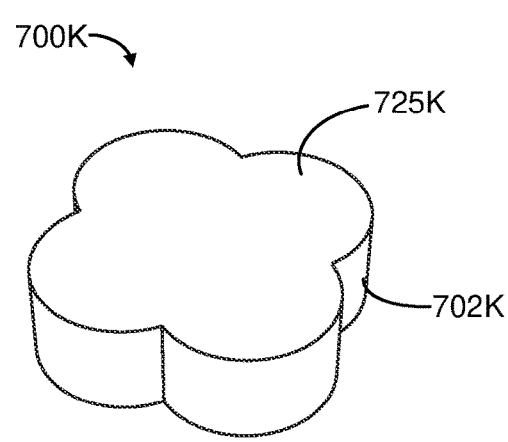
FIG. 7O is a top perspective view of another example phyto material tablet in accordance with an embodiment.

FIG. 7O illustrates another example of a phyto material tablet 700K. In phyto material tablet 700 K, rather than providing recesses in the sides 702K, the tablet 700K includes four extending sections that extend outwardly along the top surface 725K and bottom surface. The outwardly extending sections may function similarly to the recesses 707, e.g. facilitating removal of the tablet 700K and in some cases providing airflow channels.

Figure 7P:
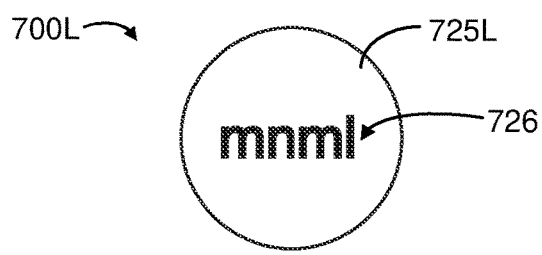
FIG. 7P is a top view of another example phyto material tablet in accordance with an embodiment.

FIG. 7P illustrates another example of a phyto material tablet 700L. Tablet 700L is an example of a phyto material tablet in which an orientation marker 726 has been printed on the top surface 725L. In some cases, the orientation marker 726 may be combined with a tablet identifier that may identify the type of tablet or the brand of the tablet.

In the example shown, the orientation marker 726 is marked on the top surface 725L. In other cases, the orientation marker 726 can be printed on the surface of the tablet 700L, e.g. using a food coloring ink. In some cases, the ink used to print the orientation marker 726 may incorporate phyto components such as terpenes.

For example, a turmeric based ink may be used. In other cases, spirulina may be used to print the orientation marker 726. When printed on the surface of a phyto material tablet 700L formed using cannabis, a turmeric ink may provide an orientation marker having a blue hue. The turmeric based ink may also be infused with components such as terpenes when printed onto the tablet 700L.

Additionally or alternatively, the tablets 200/700 may have an external coating deposited thereon after being formed into a compressed tablet. For instance, the tablets 200/700 may include a coating on one or both of the top surface and bottom surface. The coating may include components such as one or more flavonoids and/or one or more terpenes.

In some cases, the coating may be applied to the bottom surface of the tablets 200/700. This may encourage the components in the coating to be emitted first, for instance where the bottom surface of the heating chamber is heated. For example, providing terpenes on the bottom surface of a tablet that is vaporized from the bottom may help release the terpenes earlier, enabling entourage effects when consumed by a user. This may also provide an increase in flavor sensation by a user, as the terpenes and flavonoids can be consumed by the user within a first inhalation.

The tablets 200/700 may be packaged into various containers. For instance, the tablets 200/700 may be packaged in a blister pack or tube. In some cases, a childproof blister pack may be used or a childproof tube may be used. This may prevent unintended consumption of the tablets 200/700.

Figure 12:
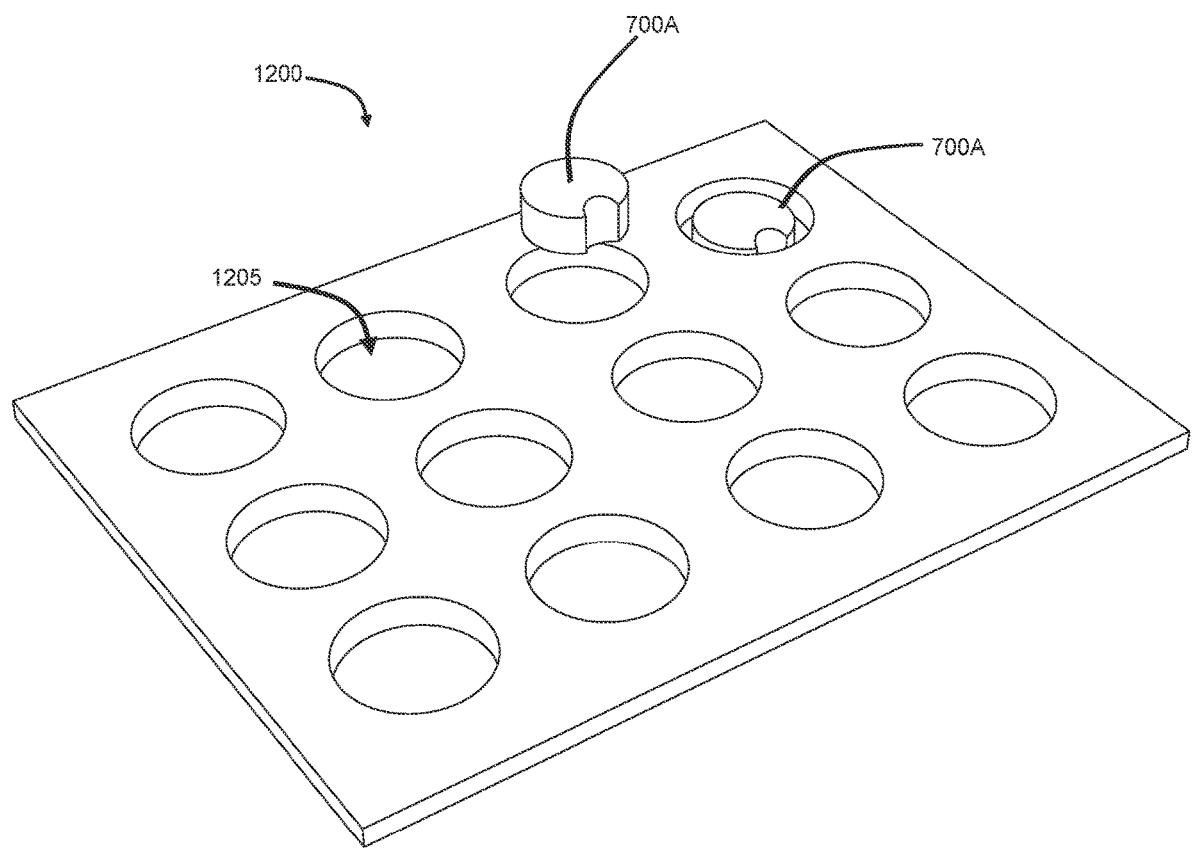
FIG. 12 is a top perspective view of a container for a plurality of phyto material tablets in accordance with an embodiment.

The container may be selected to protect the tablets 200/700 from breaking prior to use. An example of a container 1200 for a plurality of tablets 700A is shown in FIG. 12. The container 1200 is an example of a blister pack container in which a plurality of tablets 700A are provided in individual segments 1205. Each tablet 700A can be individually removed from the segments 1205 for vaporization.

In some cases, a spacer may be provided between adjacent tablets 200/700 in a container. For instance, a paper spacer may be used. This may prevent adhesion between the adjacent tablets 200/700. In other cases touching surfaces of the adjacent tablets may not be flat, and instead can be curved to reduce possible adhesion.

In some cases, a plurality of tablets 200 may be housed within a dispensing container. For instance, a dispensing magazine may be provided to house a plurality of tablets 200. The dispensing magazine may be used with a vaporization device to allow multiple tablets 200 to be individually vaporized in turn without having to manually load and re-load the device. An example of a dispensing magazine and associated vaporization device is described herein below with reference to FIGS. 5A-5I.

The phyto material tablets 200 may be manufactured using various techniques. For instance, in some cases a compression mold may be used to form the phyto material tablets 200 (as shown in FIGS. 3A-3G). In other cases, phyto material tablets 200 may be 3-D printed (as shown in FIG. 1C).

As described herein, the tablets 200/700 may be provided in various different shapes. The different shapes of tablets described herein may be used independently of, or in combination with, the other tablet features described herein above, such as the break regions, side wall recesses, orientation markers, multi-layer tablets and additional coatings. Additional examples of phyto material tablets are also described herein below, for instance in relation to FIGS. 14A-14O and 15A-15K.

Method of Forming a Phyto Material Tablet

The following is a general description of a method of forming a phyto material tablet that may be used by itself or in combination with one or more aspects of the disclosure herein, including a vaporizer for a phyto material tablet and/or a phyto material tablet. The following description contains various features of a method of forming a phyto material tablet that may be used individually or in any combination or sub-combination.

In some embodiments herein, to form the phyto material tablets 200, buds may be removed from a cannabis plant. In some cases, the leaves of the cannabis plant, separate from the buds, may also be extracted. The buds, with or without leaves, may then be ground to a desired coarseness. This ground material can then be mixed to provide a substantially homogenized phyto material mixture.

In some cases, to ensure that the cannabis product is ground to a consistent coarseness, the phyto material may be filtered. This may ensure that undesired components, such as stems, may be removed from the phyto material before forming tablets 200. This may also ensure a consistent ground material for the tablets. For example, the ground phyto material may be filtered after grinding. In other cases, a grinder with an integrated filter may be used to filter the phyto material while it is being ground.

For instance, a grinder may incorporate a mesh filter with a defined pore size. The pore size of the mesh may be selected based on a desired density of phyto material tablet. For example, a pore size of about 1 mm, 2 mm, 3 mm, 4 mm or 5 mm may be used. Particles that cannot pass through the pores of the mesh may continue to be ground until they are sufficiently small to pass through the mesh. The filtered, ground material may then be used to form phyto material tablets.

In some cases, phyto material from different cannabis plants (e.g. having different components and or different ratios of various components) may be combined prior to forming phyto material tablets. For example, phyto material harvested from different cannabis plants may be ground together to provide a homogenous ground phyto material mixture.

In some cases, phyto material from multiple strains of cannabis plants may be ground together. The ground combination of phyto material may be mixed to provide a substantially homogenized mixture. The mixture may then be tested to evaluate the quantity of various components, e.g. phyto cannabinoids and/or terpenes. The mixture may be modified, with various different strains added until desired quantities are obtained. Providing a homogenized mixture using phyto material from a plurality of strains may facilitate providing various combinations of different phyto cannabinoids, terpenes and other components that may not otherwise be available from strains of cannabis.

FIG. 16A illustrates an example of various quantities of THC and CBD that may be obtained from existing individual strains. As shown in FIG. 16A, while there are a number of different combinations of relative quantities of THC and CBD that can be obtained, there are some concentrations that do not occur in existing strains of cannabis.

FIG. 16B illustrates an example of various quantities of THC and CBD that may be obtained from blending various strains of phyto material in accordance with embodiments described herein. As shown in FIG. 16B, a large variety of different quantities of CBD and THC can be provided in a homogenized mixture when different strains and different components are mixed together.

In some cases, the mixture may include a combination of phyto material and phyto material extracts. Combining phyto material extracts with loose leaf phyto material may further facilitate obtaining a desired combination of phyto material components, such as phyto cannabinoids and/or terpenes.

The ground cannabis material or phyto material mixture can then be pressed into a tablet. For example, a mold may be used to press the cannabis material. The shape of the mold may be selected based on the desired shape of tablet. The shape may also be selected to increase the initial surface area (e.g. to ensure greater surface area is exposed if tablet does not fracture). Once pressed, the tablet may be left to cure.

In some cases, vertical recesses or indents may be formed in the sides of the tablets. These indents may provide airflow channels for the tablets. This may facilitate use with a conduction vaporizer, by allowing air to flow past the tablet more easily.

In general, the tablets described herein can be formed without any through holes. Pressing the tablets without through holes may ensure that less material break offs and is wasted during manufacturing. A solid tablet may also provide greater structural integrity for transport and handling prior to vaporization.

The compression mold may include protrusions or extensions that extend partially into a mold cavity. These protrusions can be shaped to form break regions or crumple marks in the surface of a phyto material tablet 200. This may assist in fracturing the phyto material tablet 200 for vaporization.

The compression mold may have substantially smooth molding surfaces. Accordingly, the protrusions may extend gradually out from the mold surfaces (e.g. as curved or triangular protrusions) rather than sharply. This may reduce the likelihood of phyto material sticking to the mold after compression. In some cases, the mold surfaces may be coated with an anti-stick coating, such as a ceramic coating, to reduce the likelihood of phyto material sticking thereto. For example, a titanium nitride coating may be used. In other cases, other ceramic or oxide coatings may be applied to the compression mold surfaces to reduce the phyto material adhering to the compression mold surfaces.

In some cases, the tablet forming apparatus may include an ejector mechanism. The ejector mechanism can apply a substantially consistent force across a surface of the tablet 200, such as side surface 202, to eject the tablet from the tablet forming apparatus.

Referring now to FIGS. 3A-3D, shown therein is an example of a tablet forming apparatus 300 that may be used to form phyto material tablets in accordance with an embodiment. In the example shown in FIGS. 3A-3G, the tablet forming apparatus 300 is a compression molding apparatus that may be referred to generally as mold 300. The mold 300 includes a mold cavity 315. The mold cavity 315 can receive ground phyto material (e.g. cannabis) to be formed into a tablet, such as tablets 200 described herein above.

The mold 300 includes a first mold portion 305 and a second mold portion 310. At least one of the first mold portion 305 and second mold portion 310 is moveable towards and away from the other mold portion. When the first mold portion 305 and second mold portion 310 are moved together (i.e. with outer edges in contact, or nearly in contact) they can enclose, or substantially enclose, the mold cavity 315.

One or both of the first mold portion 305 and second mold portion 310 may include at least one protrusion that extends into the mold cavity 315. The protrusions can be used to define break regions in the phyto material tablets. The protrusions can extend partially into the mold cavity 315 without extending completely through to avoid forming holes in the tablets. This may reduce the likelihood of phyto material adhering to the protrusions, and reduce fracturing of the tablets during manufacturing.

As shown in FIGS. 3A, 3B and 3D, the first mold portion 305 has a plurality of protrusions in the form of raised ribs 320. The ribs 320 can be used to define a plurality of corresponding lines of weakness (break regions) in tablets formed using the mold 300. The protrusions 320 may be arranged to define a desired break pattern for the tablet, e.g. to define a desired number of pieces or section into which the tablet is inclined to break. In some cases, as shown in FIGS. 3A, 3B and 3D, the protrusions 320 may be arranged to define a break pattern with substantially equally sized pieces into which the tablet is inclined to break. In some cases, tablets 700 may also be formed with vertically extending recesses. Accordingly, the mold 300 may also include protrusions that extend along the vertical length of the inner sides of mold cavity 315.

FIG. 3B illustrates an example of a process for loading ground phyto material into the mold cavity 315. The phyto material may be fed into the mold via conduit 325. The conduit 325 may be coupled to a phyto material forming system, such as system 100 shown in FIGS. 1A and 1B.

The phyto material loaded into cavity 315 may be derived from plant matter. For example, the phyto material may include parts removed from a cannabis plant, such as the buds and/or leaves. This phyto material may include at least one of THC and CBD.

The phyto material can be ground prior to loading into the compression mold 300. The phyto material may be ground to provide ground phyto material having a predetermined particle size (e.g. a predetermined coarseness). The particle size of the ground phyto material may be adjusted based on the desired density of the phyto material tablet being formed. The conduit 325 may have a diameter much larger than the particle size (or grinder pore size) of the ground material being fed into the cavity 315. This may reduce clogging of conduit 325.

A grinder may be used to form the ground phyto material. Depending on the predetermined particle size selected for a particular tablet 200/700, different grinders may be used to process the phyto material. For instance, grinders such as those used to grinding of herbs for Chinese medicine may even be used. For example, the phyto material can be chopped by using blades rotating at high speed (20,000 to 30,000 rpm) in a blade grinder designed for dry spices. In some cases, the rotating blades may have sharp edges to cut the phyto material. Alternatively, the rotating blades may have dulled edges. In such cases, the blades may whip the phyto material within a grinding chamber rather than chopping the phyto material.

In other cases the grinder may be provided in the form of a hammer mill. Phyto material can be inserted into a grinding chamber through a feed chute, typically with a gravity feed. The phyto material can be repeatedly struck by hammers attached to a shaft that rotates at high speed within the mill's grinding chamber. The phyto material is crushed or shattered by a combination of: repeated hammer impacts, collisions with the walls of the grinding chamber, and particle on particle impacts. A perforated filter, such as a metal screen covering a discharge opening of the hammer mill can retain coarse material for further grinding, while allowing properly sized materials to pass. The metal screen may include pores having a pore size of about 1 mm, 2 mm, 3 mm, 4 mm or 5 mm in various embodiments.

In some cases, the phyto material may be filtered to ensure that the proper coarseness is achieved. Filtering may remove ground phyto material particles larger than the predetermined particle size. For example, the phyto material may be filtered following grinding using a filter with the desired particle size. In other cases, the phyto material may be filtered prior to grinding, e.g. to remove leaves and stems. In some examples, described herein, the ground phyto material may be combined with other phyto material components, such as phyto cannabinoid extracts and/or terpenes, into a homogenized phyto material mixture or slurry that may be used to form the phyto material tablets.

In some cases, phyto material from multiple cannabis plant strains may be combined to provide the phyto material mixture. The relative quantities of the different strains can be adjusted to provide a desired combination of phyto cannabinoids and other components. The combined phyto material can be mixed to provide a substantially homogenized phyto material mixture. A sample of the mixture may then be tested to determine the relative quantities of phyto cannabinoids and other components. Based on the results of the test, further components may be added to the mixture to provide a desired phyto material mixture.

Mixing the phyto materials to provide a homogenized phyto material mixture may allow each cannabis plant to provide a more consistent yield. Within a cannabis plant, the quantities of various components (e.g. CDB, THC) found in the leaves and buds may vary across the plant (e.g. the leaves at the top may have different profiles from the leaves at the bottom). By mixing the ground phyto material, these profiles can be harmonized.

In some cases, the mixture may include both loose leaf/ground phyto material and phyto material extracts. For example, terpenes extracted from cannabis or other phyto materials may be combined with phyto material harvested from one or more cannabis plants.

Providing a homogenized phyto material mixture, with a defined ratio of phyto material components, may ensure greater consistency in user experience when consuming the phyto material. The phyto material mixture may also provide greater flexibility in preparing a phyto material tablet having specific combinations of components that may not occur naturally within a strain of cannabis.

In some cases, the specified components of the phyto material mixture may include components derived from phyto material other than cannabis. For instance, terpenes from phyto material other than cannabis may be used in the phyto material tablets. This may account for losses during harvesting of the cannabis plants. This may also allow the phyto material tablets to provide a greater range of combinations of phyto material components.

In cannabis plants, phyto cannabinoids and terpenes can be found within glandular trichomes on female cannabis plants. These glandular trichomes are hair-like protrusions that extend from the flowers and leaves. When cannabis plants are handling during harvesting, these trichomes may become damaged unless very precise handling methods are used. However, implementing sufficiently precise handling methods may substantially increase the costs of preparing phyto material tablets. Additionally, some phyto material components such as terpenes may evaporate or partially evaporate while the phyto material is cured and dried.

In some cases, terpenes derived from other phyto materials can be combined with the phyto material mixture used to form the phyto material tablets. Additionally or alternatively, flavonoids can be combined with the phyto material mixture used to form the phyto material tablets. This may facilitate preparation of the tablets (e.g. by avoiding difficult and costly handling and harvesting processes), while also allowing for controlled combinations of phyto material components.

Once prepared, the phyto material mixture can be loaded into mold cavity 315, e.g. using conduit 325. As mentioned, the mold cavity 315 can be formed by a first portion 305 and a second portion 310. At least one of the first mold portion 305 and second mold portion 310 can include an extending protrusion such as rib 320. The compression mold 300 may then be closed to press the phyto material into a tablet.

Referring now to FIG. 3C, shown therein is an example of the compression mold 300 that has been closed to compress ground phyto material (or a phyto material mixture) positioned between the first mold portion 305 and the second mold portion 305. This may compress the ground phyto material into a tablet, such as phyto material tablet 200A shown in FIG. 2A.

Various types of presses may be used to close the compression mold 300. For example, a hydraulic press can be used to control the compression mold 300. This may facilitate compressing the phyto material tablets to a suitable density and hardness to retain a rigid shape while allowing for fracturing when positioned in the heating chamber of a vaporization device.

Closing the compression mold 300 with phyto material positioned between the first portion 305 and the second portion 310 can form a phyto material tablet with a shape corresponding to the shape of the compression mold 300. As mentioned, the compression mold 300 may include one or more extending protrusions such as ribs 320. Accordingly, at least one break region 205 (e.g. a recess or depression or region of reduced thickness) can be formed in the tablet. Each break region 205 can correspond to a protrusion in the compression mold 300. For instance, the phyto material tablet 200a has recessed ribs 215 corresponding to the protruding ribs 320 provided on the first mold portion 305.

In some cases, the side surfaces of the mold cavity 315 may be shaped to define non-planar side surfaces for the tablets. For instance, the inner side surfaces of cavity 315 may include one or more inwardly extending sections (e.g. a convex protrusion) that can be shaped to define a recess (e.g. a concave recess or notch) in the side of the tablet. In other cases, the inner side surfaces of cavity 315 may be shaped to define angled or rounded side surface sections.

FIG. 3D illustrates the compression mold 851 being opened following compression of ground phyto material. A phyto material tablet 200a is shown within the mold cavity 315. As shown in FIG. 3D, the phyto material tablet 200a includes recesses 215 that correspond to the protrusions 320 on the first mold portion 305.

The ribs/recesses/depressions/regions of reduced thickness 215 can create regions of structural weakness in the phyto material tablet 200a. These regions of structural weakness (also referred to as break regions) can be defined with an arrangement that facilitates fracturing of the tablets 200 into multiple pieces. Fracturing a tablet 200 can increase the exposed surface area of the tablet. This may facilitate vaporization of the tablet 200 by increasing the ease of vaporization and/or by increasing the vaporization yield for each tablet 200.

The protrusions 320 on the compression mold 300 can be arranged so as not to perforate fully through a tablet compressed therein. For instance, as shown in FIGS. 2D and 3G, the break region 205 extends partially into the tablet 200D from the top surface 225 towards the bottom surface 230. However, the break region 205 does not extend completely through the tablet 200D.

Referring now to FIG. 3E, shown therein is an example of an ejector mechanism 330 that may be used with the compression mold 300 in accordance with some embodiments. The ejector mechanism 300 can be used to eject the phyto material tablet 200A from the second portion 310 of the compression mold 300. The ejector mechanism 330 may be used in embodiments where the second mold portion 310 provides a compression cavity in which the tablet 200 is formed.

The ejector mechanism 330 may include an ejection actuator or pin. The ejector actuator may be configured to apply pressure to one of the top surface 225 and bottom surface 230 of a tablet 200 positioned in the compression mold 300. The ejector mechanism 330 may apply a substantially constant pressure along the entirety of the top surface 225 or bottom surface 230 to eject the tablet from the compression mold cavity 315. For example, the ejector pin may be coupled to a substantially planar plate 335. The plate 335 may be provided as part of the first mold portion 305 or the second mold portion 310. In the example shown in FIG. 3E, the plate 335 forms the base of the second mold portion 310.

In some cases, the cavity of the compression mold 300 may be coated to reduce adhesion of the ground phyto material thereto. For instance, a ceramic coating may be applied to the mold cavity. This may facilitate ejection of the tablet 200 from the mold 300 after compression.

The coating applied to the compression mold 300 may be selected to prevent contamination of the tablets 200. The tablets 200 may be formed substantially entirely of plant derived material (e.g. cannabis plant material and cannabis extract). That is, the tablets 200 can be formed devoid of any external contaminants such as binders or lubricants, although resin from the plant material may act as a binder. This may ensure that the tablets 200 are formed purely, or substantially purely, of plant derived material.

In some cases, extracts from the plant material may be used to form the tablets 200. The use of a cannabis extract may facilitate binding the tablets 200. The extract may also be used to control the potency of tablets 200 being formed. In some cases, however, the tablets 200 may be manufactured solely using plant matter and resins naturally occurring in the plant matter. This may be preferred for users who are averse to any contaminants, which may include additives used to manufacture the cannabis extracts. The phyto material tablets may bind themselves once compressed and further together using the natural resins.

FIG. 3F illustrates a side view of the compression mold 300. In FIG. 3F, the top portion 305 is lowered towards bottom portion 310 to enclose the cavity 315. As shown in FIG. 3F, the ejector mechanism 330 is coupled to a lower side of the second mold portion 310. To eject a tablet 200, the ejector mechanism 330 can push the base of the second mold portion 310 upwards to raise the tablet 200 out of the mold cavity 315. The tablet 200 may then be removed from the mold 300, e.g. by sliding or lifting the tablet 200 off the surface of the second mold portion 310.

FIG. 3G illustrates an example process for removing a phyto material tablet 200 from the compression mold 300. FIG. 3G may illustrate a process for removing the phyto material tablet 200 after the phyto material tablet 200 is ejected from the mold cavity 315, e.g. using an ejector mechanism such as ejector pin 330. In the example shown in FIG. 3G, the tablet 200 is removed from the compression mold 300 using an ejection actuator 340 such as a retractable plunger. As shown in FIG. 3G, the tablet 200 may be laterally translated out of the compression mold 300 using a plunger 340 or similar mechanism.

Figure 5A:
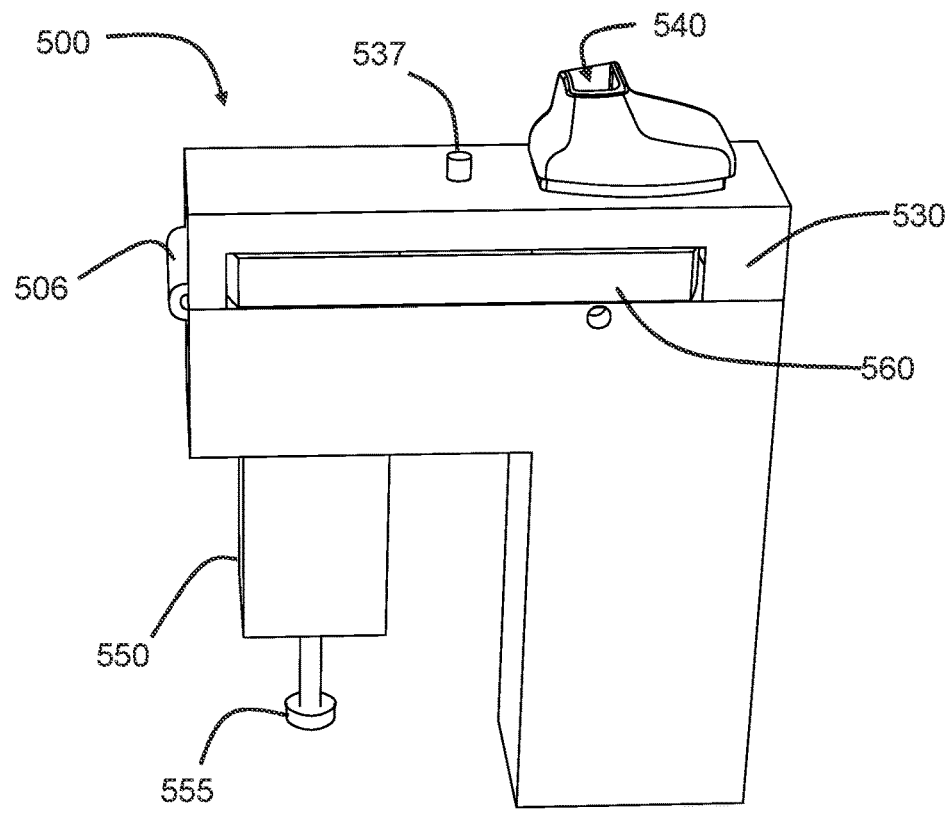
FIG. 5A is a perspective side view of an example vaporization device having a tablet dispensing apparatus in accordance with an embodiment with a lid in a closed position.

In some cases, the tablet 200 may be inserted into a multi-tablet container or magazine 550 (see e.g. FIGS. 5C-5E). For instance, a plurality of tablets 200 may be loaded into the magazine 550 as they are formed. The magazine 550 may facilitate dispensing of individual tablets 200 to a user. In some cases, a magazine 550 may be configured to be inserted into a suitable vaporization device that can retrieve individual tablets for vaporization as desired (see e.g. FIG. 5A).

In some cases, one or more of the sides of the phyto material tablet 200 may be flat or substantially planar. This may facilitate extracting the tablet 200 from the compression mold 300 by providing a surface that can be pushed by the ejection actuator 340.

As mentioned, in some embodiments the phyto material used to form the phyto material tablets may include a combination of ground plant material and cannabis extracts. Using cannabis extracts (such as oils extracted using a C02 process) to form the tablets 200 may improve tablet binding. This may also facilitate control the potency of the phyto material tablet. For instance, phyto material having a lower percentage of an active ingredient, such as THC, may be blended with a phyto material extract having a greater concentration of the active ingredient. This may provide a slurry with a desired overall THC level greater than possible from the phyto material alone. This may also facilitate varying the potency of the tablets 200 as desired; by controlling the quantity of phyto material and phyto material extract being used.

Referring now to FIGS. 1A-1C, shown therein is an example of a phyto material forming assembly 100. FIG. 1A illustrates a side view of an inside detail of the phyto forming assembly 100.

The assembly 100 may be used to create a phyto material slurry that can be used to form the phyto material tablets 200. For instance, the phyto material slurry may be loaded into a compression mold 300 via conduit 325 as shown in FIG. 3B.

The phyto material slurry may include a combination of phyto material and phyto material extract. The relative quantities and potencies of the phyto material and phyto material extract may be adjusted using the assembly 100 to produce a slurry having the desired potency of active ingredients. This may further ensure that the tablets 200 provide a consistent dose when vaporized by a user.

The assembly 100 can include a first extruder 103. The first extruder 103 may be used to extrude a first portion of ground phyto material 419. In some cases, the first extruder 103 may be coupled to the output of a grinder used to process the phyto material into ground phyto material 419.

The first extruder 103 can include an output nozzle 103a. The output nozzle 103a can be fluidly coupled to a first mixing nozzle 101. The first mixing nozzle 101 can include a mixing chamber 102. The first mixing nozzle 101 can also include an output aperture 102a. The output nozzle 103a can be used to transmit/load ground phyto material to a mixing chamber 102 provided by the first mixing nozzle 101. FIG. 1B illustrates a side view of an inside detail of the mixing chamber 102 and output aperture 102a of mixing nozzle 101.

The assembly 100 can include a second extruder 104. The second extruder 104 may be used to extrude a liquid phyto material extract 418. The second extruder 104 can also have an output nozzle 104a. The output nozzle 104a can be fluidly coupled with the first mixing nozzle 101.

The mixing nozzle 101 may receive a first portion of ground phyto material 419 from the first extruder 103. The mixing nozzle may also receive a second portion of phyto material extract 418 from the second extruder 104. The mixing nozzle 101 can mix the received ground phyto material 419 and phyto material extract 418 within the mixing chamber 102 to form a phyto material mixture 420. The phyto material mixture 420 can be emitted the output aperture 102a for use in forming a phyto material tablet. For instance, the phyto material mixture 420 may be emitted into the mold cavity 852 to form a phyto material tablet 800 using compression mold 851.

In some cases, the relative proportions of the ground phyto material 419 and phyto material extract 418 may be varied. For instance, the first portion of the ground phyto material 419 may be varied in volumetric relationship with the second portion of the phyto material extract 418 to ensure that the phyto material mixture 420 includes sufficient phyto material to form a tablet. Additionally, as mentioned above, the relative proportions may be adjusted based on the desired potency of the tablets 200 being formed. The ratio of ground phyto material 419 and phyto material extract 418 can also be varied to adjust the viscosity of the mixture 420. The ratio of ground phyto material 419 and phyto material extract 418 can also be controlled to provide defined quantities of various phyto material components, such as phyto cannabinoids, terpenes, flavonoids etc.

To ensure a desired component profile of tablet 200, the THC concentration (e.g. percent concentration) of the ground phyto material 419 can be measured. Similarly, the percentage of the phyto material extract 418 can also be measured. The ratio of phyto material extract 418 to ground phyto material 419 may then be determined to provide the mixture with a desired THC percentage.

In some cases, phyto material extract 418 can have a higher (sometimes much higher) percentage of THC than ground phyto material 419. Accordingly, the THC percentage of the phyto material mixture 420 may be greater than the THC percentage of the ground phyto material 419 and less than the THC percentage of the phyto material extract 418.

In some cases, additional additives may be included in the phyto material mixture 420. For instance, vitamins and/or other oils suitable for inhalation may be added to phyto material mixture. This may provide a user with additional benefits (e.g. from the vitamins) or produce a mixture 420 that provides a desired smell or flavor when vaporized.

In some cases, the assembly 100 may also include one or more heating components. For instance, a first heater 105 may be included that is arranged to heat the mixing nozzle 101 to a first predetermined temperature. The first predetermined temperature may be selected to facilitate the flow of phyto material extract 418 through the first mixing nozzle 101.

Additionally or alternatively, a second heater 106 may be included that is arranged to heat the first extruder 103 to a second predetermined temperature. The second predetermined temperature may be selected to facilitate a flow of the phyto material extract 418 through the second extruder 104.

In some cases, the assembly 100 may also include a first container 107 that can be fluidly coupled to the first extruder 103. The container 107 may contain ground phyto material 419. The container 107 may be used to provide the ground phyto material 419 to the first extruder 103. In some cases, the container 107 may be arranged at least partially above the first extruder 103. Accordingly, feeding of the ground phyto material 419 into the first extruder 103 may be gravity-assisted.

In some cases, the assembly 100 may also include a second container 108 that can be fluidly coupled with the second extruder 104. The second container 108 may contain the phyto material extract 418. The second container 108 may be used to provide the phyto material extract 418 to the second extruder 104. In some cases, the second container 108 may be pressurized to assist feeding the phyto material extract 418 into the second extruder 103.

As mentioned, the assembly 100 may include one or more heaters. The second container 108 may be fluidly coupled to the second extruder 104 by a fluid coupling 109. The fluid coupling 109 may include a heater 110 disposed about an outer diameter thereof for providing heat to the phyto material extract 418. This may facilitate the flow of phyto material extract to the second extruder 104.

In some cases, the phyto material mixture 420 may be provided as the input to a mold, such as compression mold 300, for use in forming phyto material tablets 200. In other cases, the phyto material mixture 420 may be used as raw material for 3D printing phyto material products, such as phyto material tablets 200.

For example, the phyto material extract 418 may be combined with the ground phyto material 419 to form the phyto material mixture 420. This mixture may be selectively emitted from the output aperture 102a to form a three dimensional shape. The mixture 420 extruded from the mixing chamber output aperture 102a may then be allowed to cure/cool. The phyto material mixture 420 may then form into a shaped phyto material mixture structure 420a. For instance, the phyto material mixture structure 420a may be formed into a desired shape of tablet 200.

Depending on the type of vaporizer, the process of forming tablets 200 may be adjusted. For instance, for convection vaporizers, an increased surface area may be particularly desirable. Accordingly, the tablets 200 can be formed to provide a maximum surface area when vaporized (e.g. by providing a large exposed surface area using indents etc. and/or by facilitating fracturing in a vaporizer). For conduction vaporizers, a more densely packed phyto material tablet 200 may be preferred. Accordingly, a densely packed tablet 200 that includes multiple break regions may facilitate use with both conduction vaporizers (because of the packing density) and convection vaporizers (because of the increased fracturability).

In some cases, one or more phyto material components may be added to the phyto material tablets after the tablets are formed. For example, one or more terpenes may be added to (e.g. deposited on) the phyto material tablets after the tablets are formed to reduce or avoid evaporation during the manufacturing of the tablets.

In some cases, the phyto material components may be added to the phyto material tablets after the phyto material tablets have been inserted into, but not sealed within, a container. For instance, a phyto material tablet may have one or more phyto material component added thereto after being positioned within a chamber of a blister pack. The blister pack chamber may subsequently be sealed to enclose the tablet with the phyto material component deposited thereon. This may further reduce evaporation.

Figure 13A:
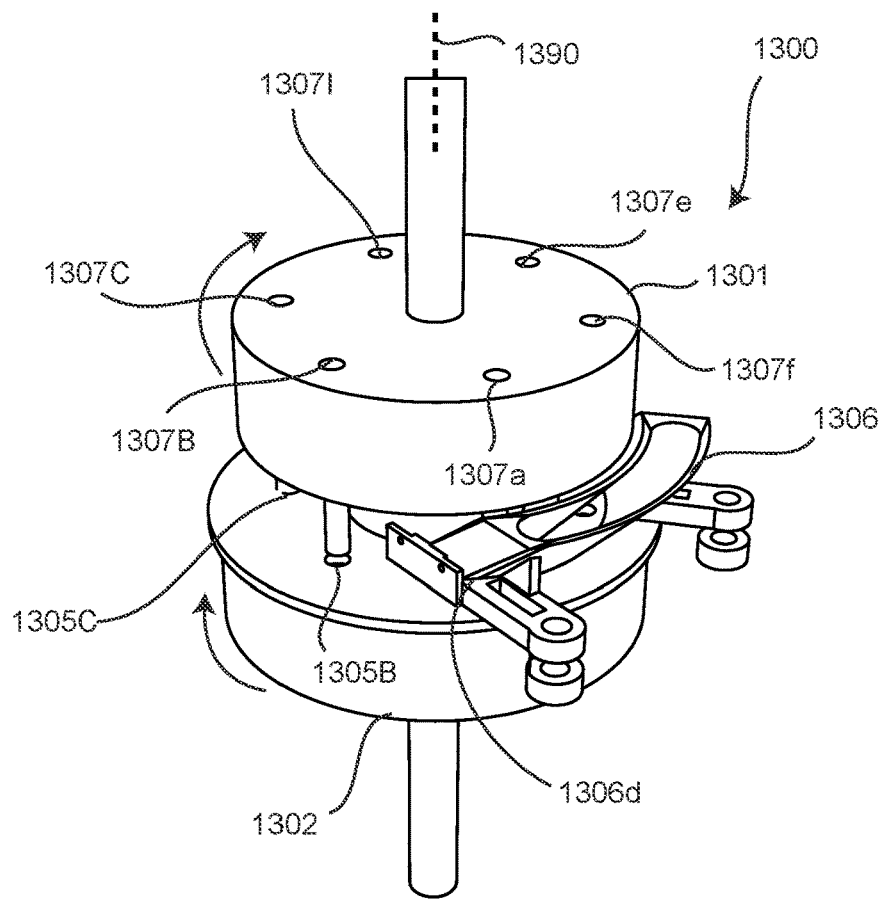
FIG. 13A is a perspective view of an example tablet forming apparatus in accordance with an embodiment.
Figure 13B:
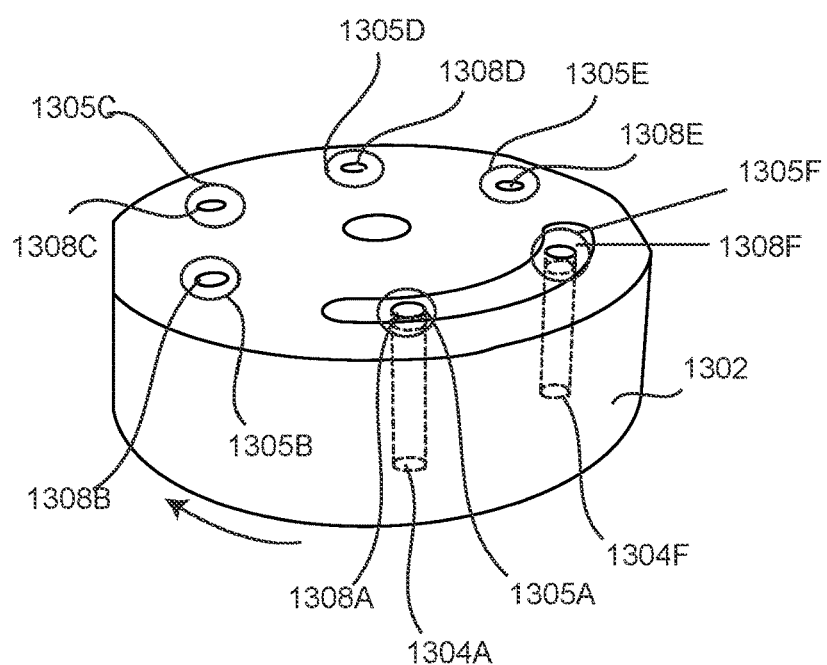
FIG. 13B is a perspective view of a second section of the tablet forming apparatus of FIG. 13A in accordance with an embodiment.
Figure 13C:
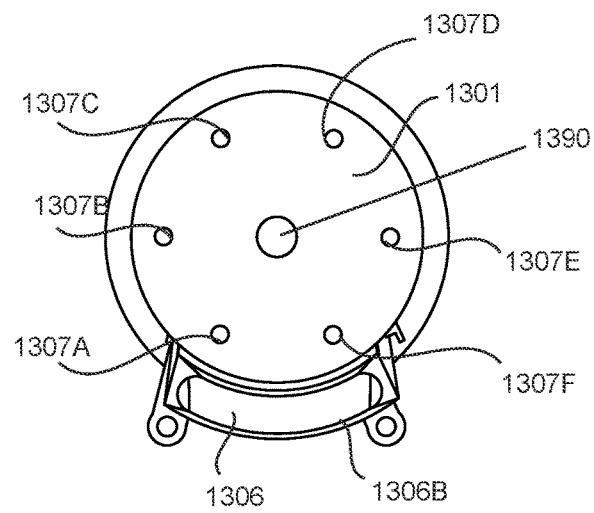
FIG. 13C is a top view of a first section of the tablet forming apparatus of FIG. 13A in accordance with an embodiment.
Figure 13D:
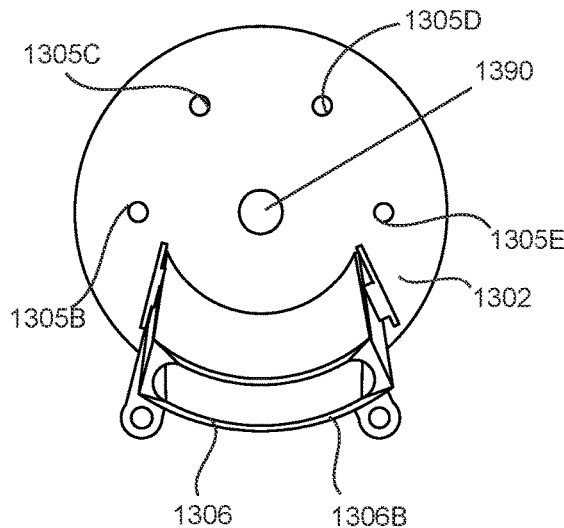
FIG. 13D is a perspective view of the second section of the tablet forming apparatus of FIG. 13A with a phyto material dispensing apparatus in accordance with an embodiment.
Figure 13E:
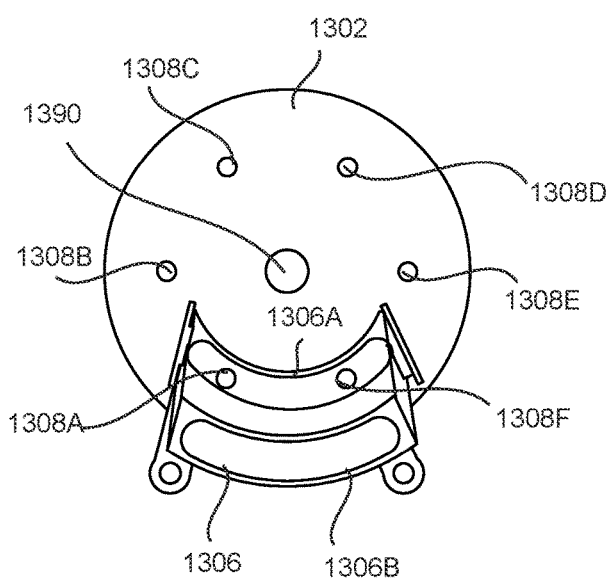
FIG. 13E is a perspective view of the second section of the tablet forming apparatus of FIG. 13A with a phyto material dispensing apparatus shown in a partial cut-away in accordance with an embodiment.
Figure 13F:
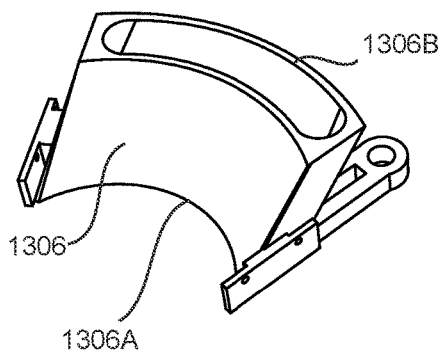
FIG. 13F is a side perspective view of an example phyto material dispensing apparatus that may be used with the tablet forming apparatus of FIG. 13A in accordance with an embodiment.
Figure 13G:
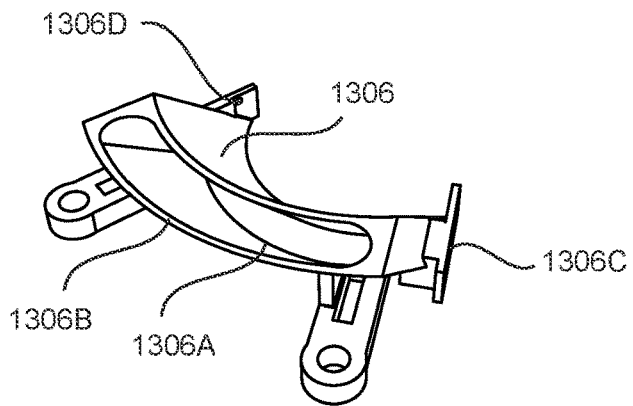
FIG. 13G is top perspective view of the phyto material dispensing apparatus of FIG. 13F in accordance with an embodiment.
Figure 13H:
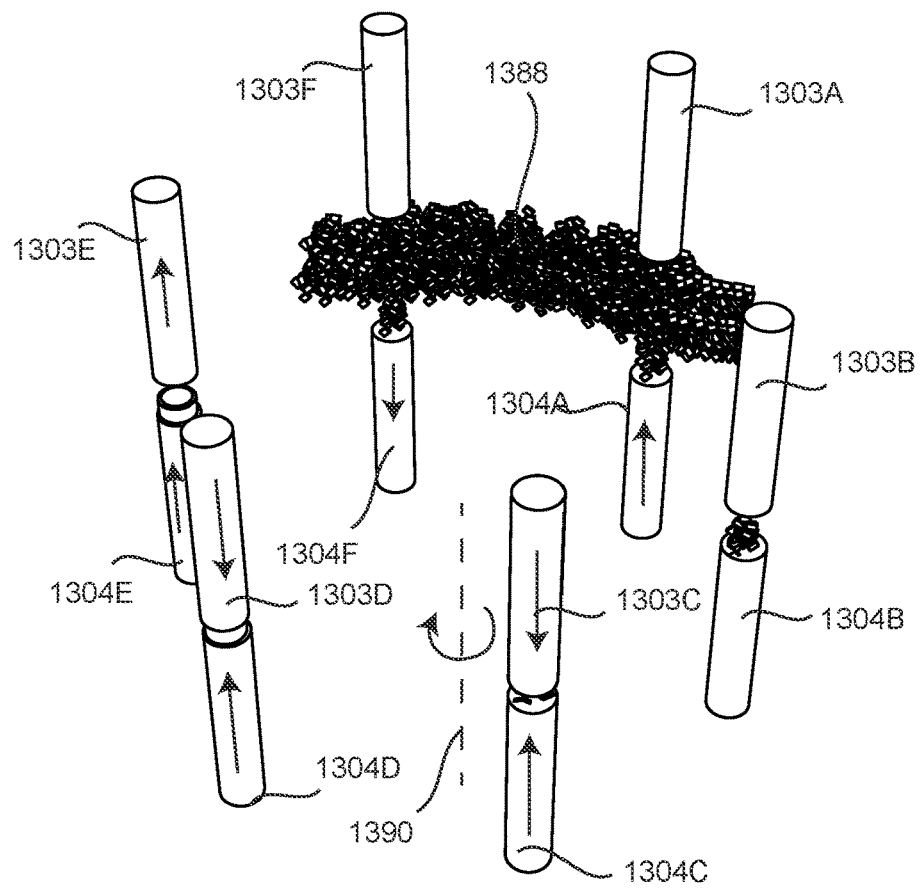
FIG. 13H is a perspective view of tablet compression members that may be used in the tablet forming apparatus of FIG. 13A with the tablet compression members in a first position in accordance with an embodiment.
Figure 13I:
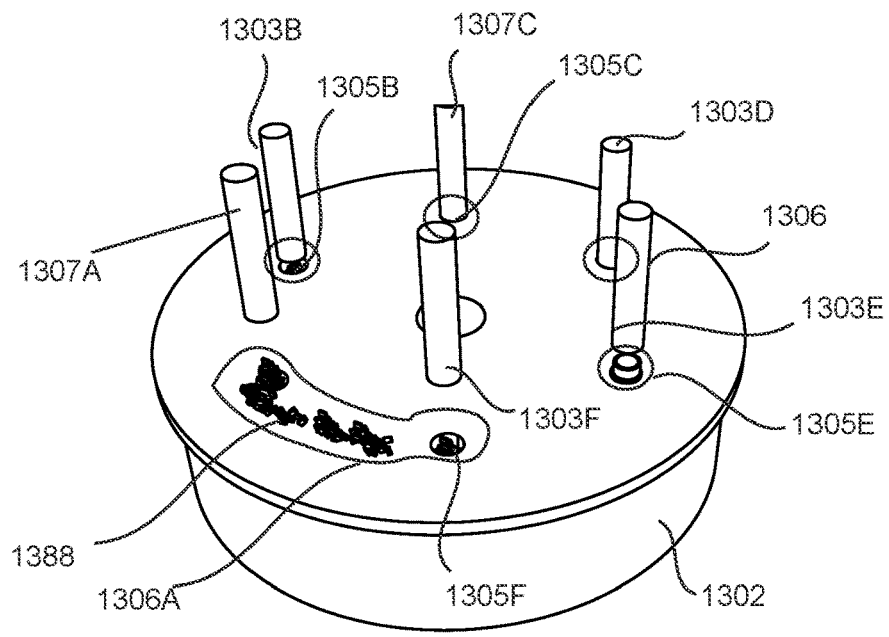
FIG. 13I is a perspective view of the second section of the tablet forming apparatus of FIG. 13A and tablet compression members in accordance with an embodiment.
Figure 13J:
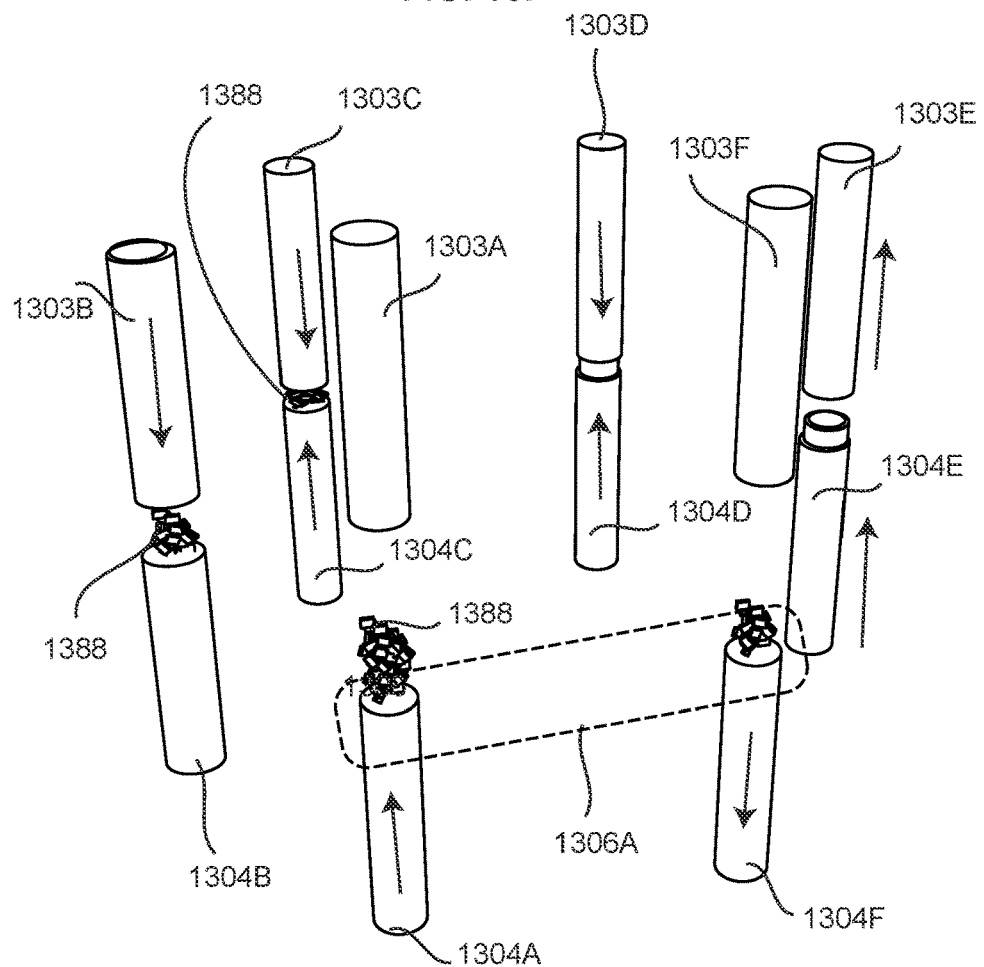
FIG. 13J is a perspective view of tablet compression members that may be used in the tablet forming apparatus of FIG. 13A with the tablet compression members in a first position in accordance with an embodiment.
Figure 13K:
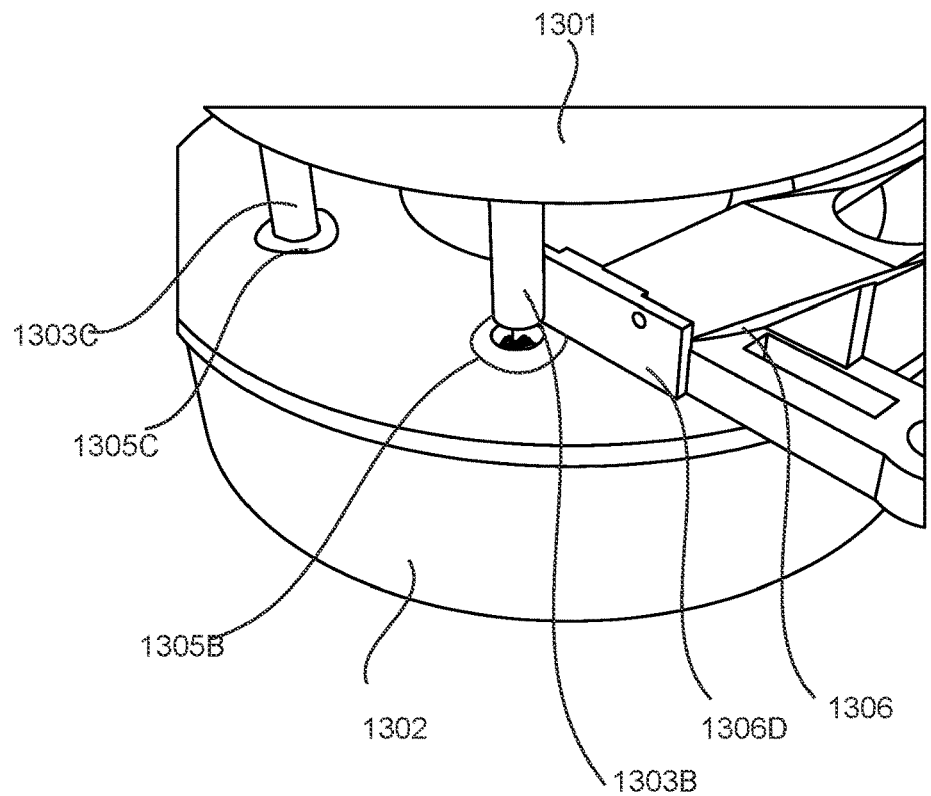
FIG. 13K is a perspective view of a portion of the tablet forming apparatus of FIG. 13A with compression members forming a phyto material tablet in accordance with an embodiment.
Figure 13L:
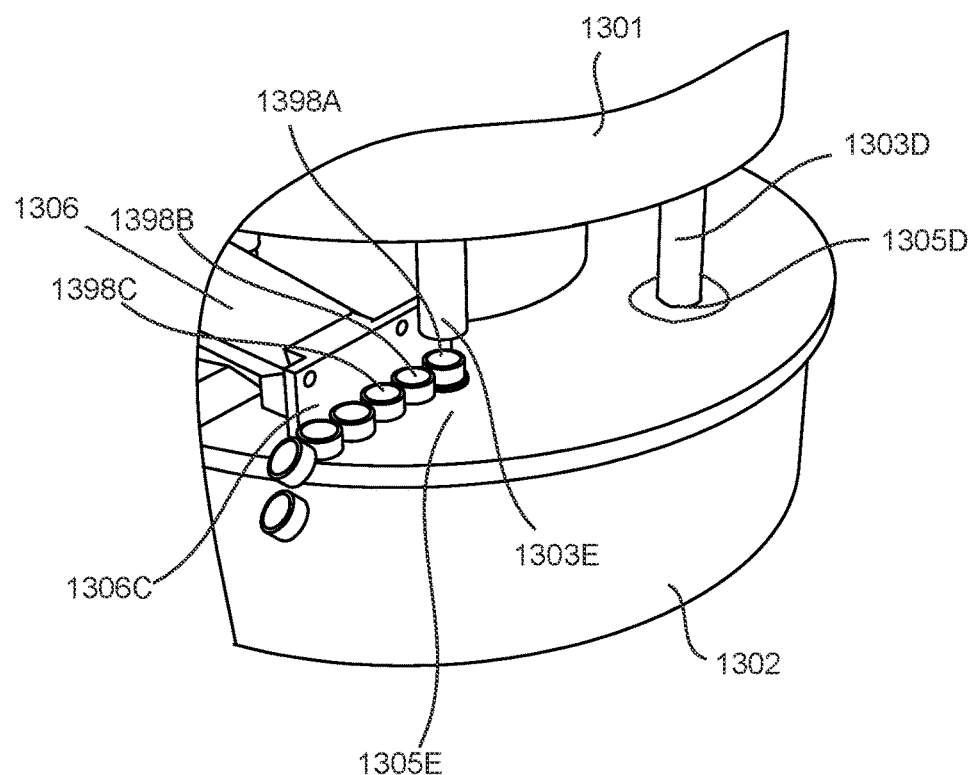
FIG. 13L is a perspective view of a portion of the tablet forming apparatus of FIG. 13A with a plurality of phyto material tablets shown in accordance with an embodiment.
Figure 13M:
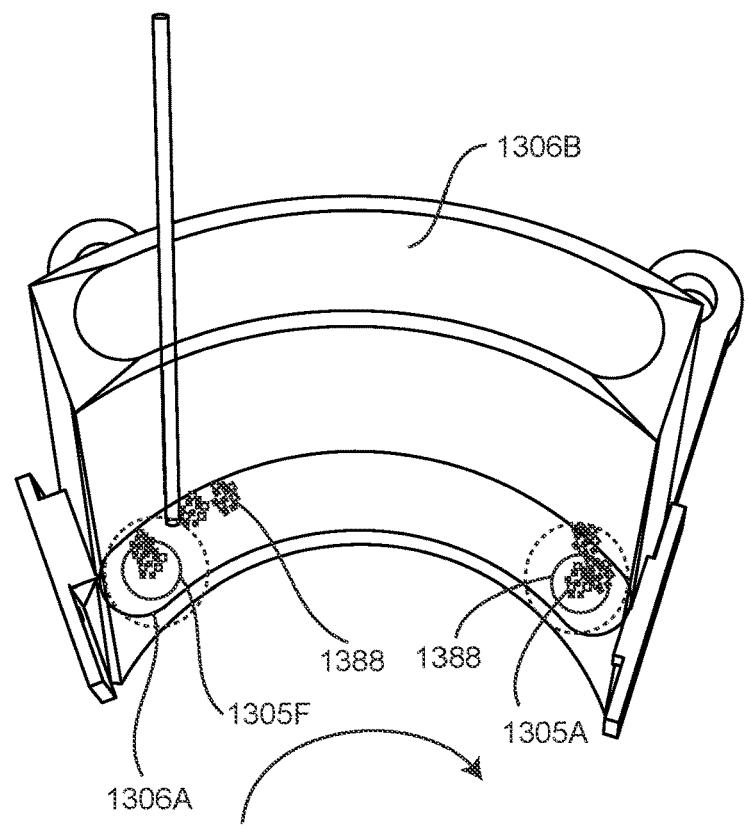
FIG. 13M is a perspective view of an example phyto material dispensing apparatus in accordance with an embodiment.
Figure 13N:
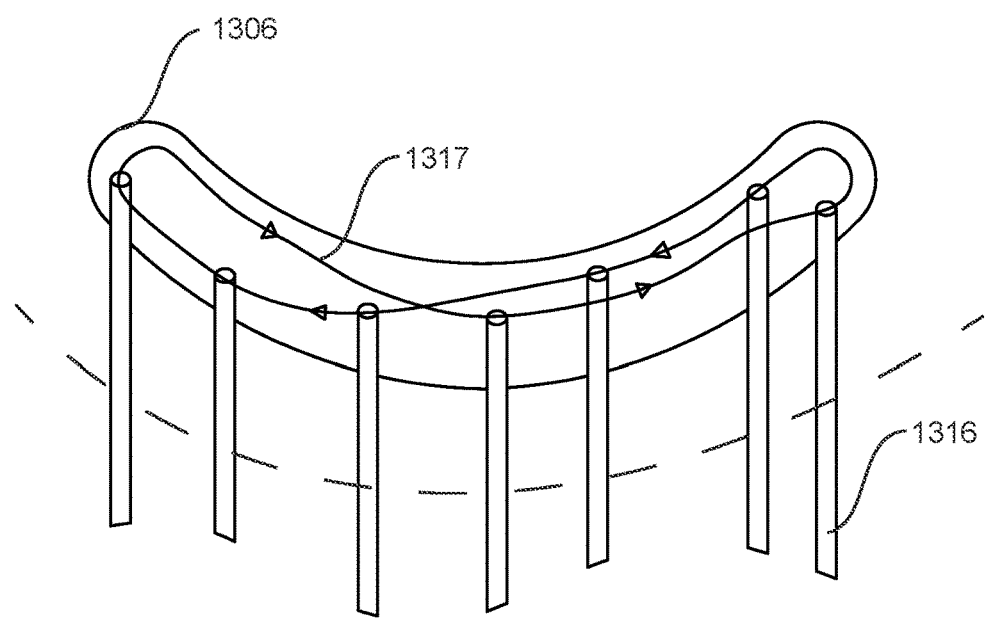
FIG. 13N is a perspective view of an example agitation member that may be used with the example phyto material dispensing apparatus of FIG. 13M in accordance with an embodiment.

Referring now to FIGS. 13A-13N, shown therein is another example of a tablet forming apparatus 1300 that can be used to form a phyto material tablet. The tablet forming apparatus 1300 can be configured to form phyto material tablets using compression members and corresponding molds or dies.

The tablet forming apparatus 1300 includes a first section 1301 and a second section 1302. In the example shown, the first section 1301 is an upper section positioned above the second lower section 1302. The first section 1301 and second section 1302 are concentrically aligned with one another about a central axis 1390.

One or both of the first section 1301 and second section 1302 can rotate about the central axis 1390. In the example shown, the first section 1301 and second section 1302 are cylindrical sections that are both rotatable about the central axis 1390.

The tablet forming apparatus 1300 can include a first plurality of compression members or punches 1303a-1303f. The first section 1301 can include a first plurality of channels or cavities 1307a-1307f through which the compression members 1303a-1303f can translate axially (i.e. through which the punches 1303 can move vertically). Each compression member 1303a-1303f can correspond to a particular channel 1307a-1307f.

The tablet forming apparatus 1300 can include a second plurality of compression members 1304a-1304f. The second section 1302 can include a second plurality of channels or cavities 1308a-1308f through which the compression members 1304a-1304f can translate axially (i.e. through which the punches 1304 can move vertically). Each compression member 1304a-1304f can correspond to a particular channel 1308a-1308f.

The channels 1307a-1307f can be distributed circumferentially around the cylindrical first section 1301. Similarly, the channels 1308a-1308f can be distributed circumferentially around the second section 1302. The spacing of the channels 1307 and 1308 can be aligned, so that when the first section 1301 faces the second section 1302, each channel 1307 can be aligned to face a corresponding channel 1308.

A plurality of tablet dies 1305a-1305f can be positioned between the first section 1301 and second section 1302. As shown, the tablet dies 1305 may be defined in a surface of the second section 1302 facing the first section 1301 (see e.g. FIG. 13K). The tablet dies 1305 can be spaced circumferentially around the tablet forming apparatus 1300. The dies 1305 can be positioned with same arrangement as the channels 1307/1308. When in use, the first section 1301, second section 1302 and dies 1305 can be aligned so that separate tablet forming units are defined by aligning each die 1305 with one channel 1307 and one channel 1308.

In operation, to form a phyto material tablet, a tablet forming unit can be defined with a first compression member 1303 aligned with a second compression member 1304 and with a die 1305 positioned between the first compression member 1303 and second compression member 1304. Phyto material (e.g. ground phyto material and/or homogenized phyto material as described herein above) can be dispensed into the die 1305. The first compression member 1303 and second compression member 1304 can be moved towards one another to compress the phyto material within the die 1305. The first compression member 1303 and second compression member 1304 may each be mounted to respective cam mechanisms to facilitate relative movement towards and away from one another. The compression of the phyto material can shape a tablet which can then be ejected from die 1305.

In the example shown, the dies 1305 are circular. However, the shape of the dies 1305 may be adjusted based on the desired shape of a phyto material tablet, such as the tablets 200/700 described herein above. For example, rectangular or triangular dies may be used. In some cases, the dies may include sidewall projections that can be used to form recesses or notches in the sides of the tablets.

The surfaces of the compression members 1303/1304 facing the die 1305 can also be modified based on the desired tablet configuration. In the example shown, the compression members have substantially smooth, planar surfaces. However, one or both of the compression members may include projections members such as ribs that can be used to form recesses in the upper and/or lower surfaces of a tablet. In some cases as a surface area of the tablet is increased, increased pressure can be applied to form the compressed tablet.

In the example shown, the tablet forming apparatus 1300 includes six tablet forming units. In other examples, different numbers and arrangement of tablet forming units (e.g. 1, 2, 3, 4, 5 and so on) may be used.

The phyto material may be dispensed using a dispensing apparatus 1306. The tablet forming apparatus 1300 may mount the dispensing apparatus 1306 so that the first section 1301, second section 1302 and dies 1305 are moveable relative to the dispensing apparatus 1306. For example, the dispensing apparatus 1306 may be stationary while the first section 1301 and second section 1302 are rotatable about the central axis 1390. The dispensing apparatus 1306 may be removably mounted to tablet forming apparatus 1300 (e.g. to a housing thereof). This may allow dispensing apparatus 1306 to be removed for cleaning.

The dispensing apparatus 1306 can be used to position phyto material in the dies 1305 prior to compression into tablets. As shown, the dispensing apparatus 1306 can provide a gravity-assisted feed of phyto material. The dispensing apparatus 1306 may also be configured to eject the tablets from the dies 1305 following compression.

The dispensing apparatus 1306 may include a first die facing end 1306*a* and an opposed second end 1306*b*. As shown, the second end 1306*b* may be open and exposed from the tablet forming apparatus 1300. The second end 1306*b* may allow phyto material to be loaded into the dispensing apparatus 1306. Phyto material may be added into the second end 1306*b* on a periodic or continual basis as phyto material is depleted from the dispensing apparatus 1306.

The first end 1306*a* can also be open. The first end 1306*a* can be positioned facing the upper surface of the second section 1302. Phyto material that is positioned within the dispensing apparatus 1306 can be fed into the dies 1305 view the first end 1306*a*.

The dispensing apparatus 1306 can define an internal phyto material hopper positioned between the first end 1306*a* and second end 1306*b*. The internal phyto material hopper can be used to store phyto material prior to deposition into the dies 1305. In some cases, the inner surfaces of the phyto material hopper may be provided with an anti-stick coating (e.g. a ceramic coating). This may reduce adhesion between the inner walls and the phyto material contained therein.

The tablet dispensing apparatus 1306 can be shaped to correspond to the arrangement of dies 1305. As shown, the dies 1305 are arranged circumferentially around the top surface of the second section 1302. Accordingly, the tablet dispensing apparatus 1306 has a curved shape that corresponds to the circumferential arrangement of dies 1305.

The tablet dispensing apparatus 1306 can be configured to be longer than it is wide. In the example of the curved tablet dispensing apparatus 1306, the dispensing apparatus 1306 has a greater circumferential extent than its radial width. For example, the tablet dispensing apparatus 1306 may have a circumferential extent that is about four times greater than its radial width. In some cases, the ratio of circumferential extent and radial width may be about 5:1 or 6:1.

The width of the dispensing apparatus 1306 may also be greater than the width of the phyto material receiving volume defined for each die 1305. The width of the dispensing apparatus 1306 may be at least two times greater than the width of the phyto material receiving volume defined for each die 1305. For example, the dispensing end of dispensing apparatus 1306 may have a width that is about 3× to 4× to 5× greater than the radial width of the phyto material receiving volume. This may facilitate the flow of phyto material into the dies 1305, in particular when an agitation member 1316 is used. In other cases the hopper may have a width that is about 8× greater than the radial width of the phyto material receiving volume.

The dispensing apparatus 1306 can be positioned with the hopper at a primarily vertical angle relative to the second section 1302 (e.g. more vertical than horizontal). This may encourage phyto material to fall into the dies 1305, while avoiding contact with the first section 1301.

As mentioned, the dies 1305 are rotatable with respect to the tablet dispensing apparatus 1306. When a die 1305 is positioned underlying the first end 1306*a*, phyto material from within the dispensing apparatus 1306 can be dispensed into the die 1305. The deposited phyto material can then be compressed into a tablet by moving the compression members 1303/1304 together. The tablet may then be ejected from the apparatus 1300.

The dispensing apparatus 1306 may also include a volume control member 1306*d*. The volume control member 1306*d* may control the volume of phyto material deposited into a die 1305. As the second section 1302 rotates with respect to the dispensing apparatus 1306, the volume control member 1306*d* may skim phyto material from the upper side of the die 1305 and retain the skimmed phyto material within the hopper cavity.

The dispensing apparatus 1306 may also include an ejector member 1306*c*. The ejector member 1306*c* may be used to eject formed tablets from the upper surface of the second section 1302.

FIGS. 13H-13J illustrate an example of the operation of the tablet forming apparatus 1300 with components of the apparatus 1300 omitted to facilitate understanding. As shown in FIG. 13H, the tablet forming apparatus 1300 may include six tablet forming units that each include compression members 1303/1304 and a die 1305. In operation, each tablet forming unit may perform the same operations sequentially as the dies 1305 are rotated with respect to a phyto material dispensing apparatus 1306.

As shown in FIG. 13I, a die 1305f can be positioned aligned with the first end 1306a of the dispensing apparatus 1306. The compression members 1303f and 134f are both in retracted positions to enable phyto material to be dispensed into die 1305f.

The upper compression member 1303f may be in a retracted position to avoid engaging the dispensing apparatus 1306. The retracted position of the lower compression member 1304f can be below the surface of the second section 1302 defining a lower surface of a phyto material receiving volume defined by the sidewalls of die 1305f. The retracted position of the lower compression member 1304f may be adjusted to define a desired volume of phyto material to be used in forming the tablet. By lowering the compression member 1304f when phyto material is being dispensed, the volume may be increased. By raising the compression members 1304f when phyto material is being dispensed, the volume may be decreased.

Phyto material from the dispensing apparatus can then be dispensed to fill the phyto material receiving volume. Subsequently, as the die 1305f is rotated relative to the dispensing apparatus 1306, the volume control member 1306d can skim phyto material that extends above the surface of the second section 1302. As a result, the phyto material can be contained within a phyto material receiving volume that is defined by the upper surface of compression member 1304f, the sidewalls of die 1305f, and an open end at the surface of the second section 1302. The skimmed phyto material can be retained within the dispensing apparatus 1306 to be used in a subsequent die 1305.

The volume control member 1306d may be positioned contacting the upper surface of the second section 1302. This may ensure that all, or substantially all, of the phyto material that is deposited above the phyto material receiving volume can be skimmed and retained within the dispensing apparatus 1306.

The first end 1306a may have a sidewall defining the lower end of the hopper volume. The sidewall of the first end 1306a may also engage the surface of the second section 1302 to prevent phyto material from exiting the dispensing apparatus 1306 other than into dies 1305.

This process of positioning the compression members 1303/1304 in retracted positions, dispensing phyto material, and skimming the phyto material can be repeated for each die 1305 sequentially as they rotate with respect to the dispensing apparatus 1306.

Once phyto material has been dispensed into die 1305f, the die 1305f can rotate so that it is no longer aligned with dispensing apparatus 1306. The upper compression member 1303 may then be lowered to enclose the phyto material receiving volume. The compression members 1303 and 1304 can then be moved towards one another to compress the dispensed phyto material into a phyto material tablet. The force applied between the compression members 1303 and 1304 may be adjusted based on a desired density of tablet.

Once the tablet has been compressed, the upper compression member 1303 can be retracted. A phyto material tablet may then be provided within the phyto material receiving volume. The lower compression member 1304 may then extend into an extended position flush with, or slightly protruding from the upper surface of the second section. The tablet may then be removed from the tablet forming apparatus 1300.

As the die rotates, the tablet may be removed by engaging the tablet dispensing apparatus 1306. The ejector member 1306c can force the tablet from the surface of the lower compression member 1304. As additional tablets are formed and ejected, they can be translated off the edge of the second section 1302 (FIG. 13L). The formed tablets can then be positioned within a container, such as a blister pack or dispensing magazine as desired. Since the dispensing apparatus 1306 can remain stationary, each tablet can be ejected at substantially the same position. This may facilitate loading into a container.

In some cases, the tablets may be positioned within a container, such as a blister pack, once formed. One or more components, such as phyto cannabinoids or terpenes can then be added to the tablets while held within the container. The tablets can then be sealed within the container after the components are added. This may reduce losses associated with drying and curing, as well as damage that may occur during pressing.

In some cases, the dispensing apparatus 1306 may include an agitation member 1316. The agitation member 1316 can be positioned within the hopper volume of the dispensing apparatus 1306. The agitation member 1316 can be movable within the hopper volume. This may ensure that phyto material in the hopper volume does not become stagnant and possibly clogged in the dispensing apparatus 1306. This may also prevent the phyto material from becoming bunched proximate the volume control member 1306d when phyto material is skimmed from the dies 1305.

As shown in FIG. 13N, the agitation member 1316 can be moved through the hopper volume along an agitation path 1317 that generally resembles a FIG. 8. The agitation member 1316 may also move vertically within the hopper volume to further agitate phyto material that may become stuck to the inner surfaces of the dispensing apparatus 1306.

In some cases, the dies 1305 may be rotated continuously with respect to the dispensing apparatus 1306. In other cases, the dies 1305 may be rotated with respect to the dispensing apparatus 1306 at sequential intervals. For example, the dies 1305 may be rotated to face the first end 1306a of dispensing apparatus 1306 individually. In other cases, two dies 1305 can be positioned facing the first end 1306a (see e.g. FIG. 13E). The dies 1305 may be positioned below the first end 1306a for a period of time to allow the phyto material to fall into the phyto material receiving volume. As mentioned above, the phyto material receiving volume may be adjusted so that a defined quantity of phyto material (e.g. 0.2 g, 0.3 g etc.) can be positioned therein. While the dies 1305 are positioned below the first end 1306a, the agitation member 1316 may be moved to encourage phyto material to be deposited and occupy the entire phyto material receiving volume.

In some examples, the tablet forming apparatus 1300 may rotate once every second. In other cases, the tablet forming apparatus 1300 may rotate about once every two seconds.

In some embodiments, the tablet forming apparatus 1300 may be configured to form multi-layer tablets. For example, the tablet forming apparatus 1300 may include two or more dispensing apparatuses, such as dispensing apparatus 1306. The dispensing apparatuses may be positioned at intervals along the rotation of the dies 1305. In some cases, each dispensing apparatus may be configured to provide a different phyto material mixture to be included in the tablets.

In some embodiments, an initial tablet layer may be provided by lowering the compression member 1304 to a first receded height defining a first phyto material receiving volume. Phyto material can be deposited into the die, and an initial tablet layer formed as described above, by compressing the deposited phyto material mixture between the compression members 1303 and 1304. A subsequent layer of phyto material mixture may then be deposited on top of the first compressed layer, and this additional layer can be compressed with the first layer in the same manner.

In some cases, a subsequent tablet layer may be provided by lowering the compression member 1304 to a second receded height, further below the upper surface of the die 1305. This may provide a second phyto material receiving volume that allows additional phyto material to be deposited. This may enable the same amount of phyto material mixture to be deposited for the first and second layers. In some cases, the upper compression member 1303 may also be lowered further along with the compression member 1304 so that the first compressed tablet layer recedes to the bottom of the phyto material receiving volume. This may ensure that the maximum available area of the second phyto material receiving volume can be used to receive the second layer of phyto material.

In some cases, the process of layering phyto material and phyto material mixtures may be repeated multiple times to provide the desired layering for the phyto material tablet. In some cases, cannabis extracts or other components may be deposited between layers of phyto material. The extracts or cannabis oils may be deposited to facilitate ingestion of extracts or oils that may typically come in liquid forms in a vaporizer intended for phyto material and phyto material tablets. In some cases, the deposited materials may provide additional binding between the layers of compressed phyto material. In some cases, this may allow the tablet to provide a staged or sequential experience when consumed by a user. For example, different flavonoids or terpenes may be deposited in a sequence to provide a changing taste when the tablet is consumed.

In some embodiments, the phyto material used to form a tablet may include tobacco instead of, or in addition to, cannabis phyto material. For example, a phyto material tablet may be formed by compressing tobacco with an additional deposition of other phyto components, such as CBD or terpenes. For example, CBD may be used as a binder for a compressed tobacco tablet. In some cases, tobacco may be included as a layer in a multi-layer phyto material tablets that also includes layers from other phyto materials such as cannabis.

Vaporizer for Phyto Material Tablet

The following is a general description of a vaporizer for a phyto material tablet that may be used by itself or in combination with one or more aspects of the disclosure herein, including a phyto material tablet and/or a method of forming a phyto material tablet. The following description contains various features of a vaporizer that may be used individually or in any combination or sub-combination.

A vaporization device or vaporizer provided in embodiments described herein may facilitate increasing the surface area of a phyto material tablet to be vaporized.

A vaporization device or vaporizer provided in embodiments described herein may also facilitate providing a controlled dose of phyto material vapor to a user.

In general, the vaporizer can include a heating chamber. The heating chamber can be shaped to receive a phyto material tablet. The vaporizer may be configured to fracture the phyto material tablet once loaded into the heating chamber. This may create airflow channels between the fractured pieces of the phyto material tablet to facilitate vaporization.

One or more surfaces of the heating chamber may include a fracturing region shaped to facilitate fracturing of the phyto material tablet. For example, a lower surface of the heating chamber may be shaped to fracture the phyto material tablet.

The lower surface may have various shapes configured to apply a variable force on the phyto material tablet when the tablet is pressed into the heating chamber. For example, the lower surface may be textured or dome shaped in some embodiments. In some embodiments, the lower surface may include extending spikes or protrusions that may interact with the phyto material tablet when it is inserted into the heating chamber. The lower surface may break the phyto material tablet into at least two pieces. In some cases, the phyto material tablet may be broken into more than two pieces. Breaking the tablet into pieces may facilitate airflow around and through the tablet during vaporization. This may also increase the exposed surface area of the plant material in the tablet to ensure that more plant material is consumed during vaporization. In some cases, multiple surfaces of the heating chamber may include fracturing regions.

To fracture a tablet positioned in the heating chamber, the lid of the heating chamber may be closed to apply force to a top surface of the tablet. Fracturing regions may be provided on one or both of the lower lid surface (i.e. the heating chamber top surface) or the heating chamber bottom/lower surface. When the heating chamber lid is closed, the phyto material tablet can be sandwiched between the lid and the base of the heating chamber and broken into the at least two pieces.

In some cases, one or more sides of the heating chamber may be heated to facilitate fracturing a phyto material tablet positioned therein. For example, a lower surface of the heating chamber may be heated. The lid may include a fracturing member that extends into the heating chamber to fracture a tablet positioned therein.

Figure 4A:
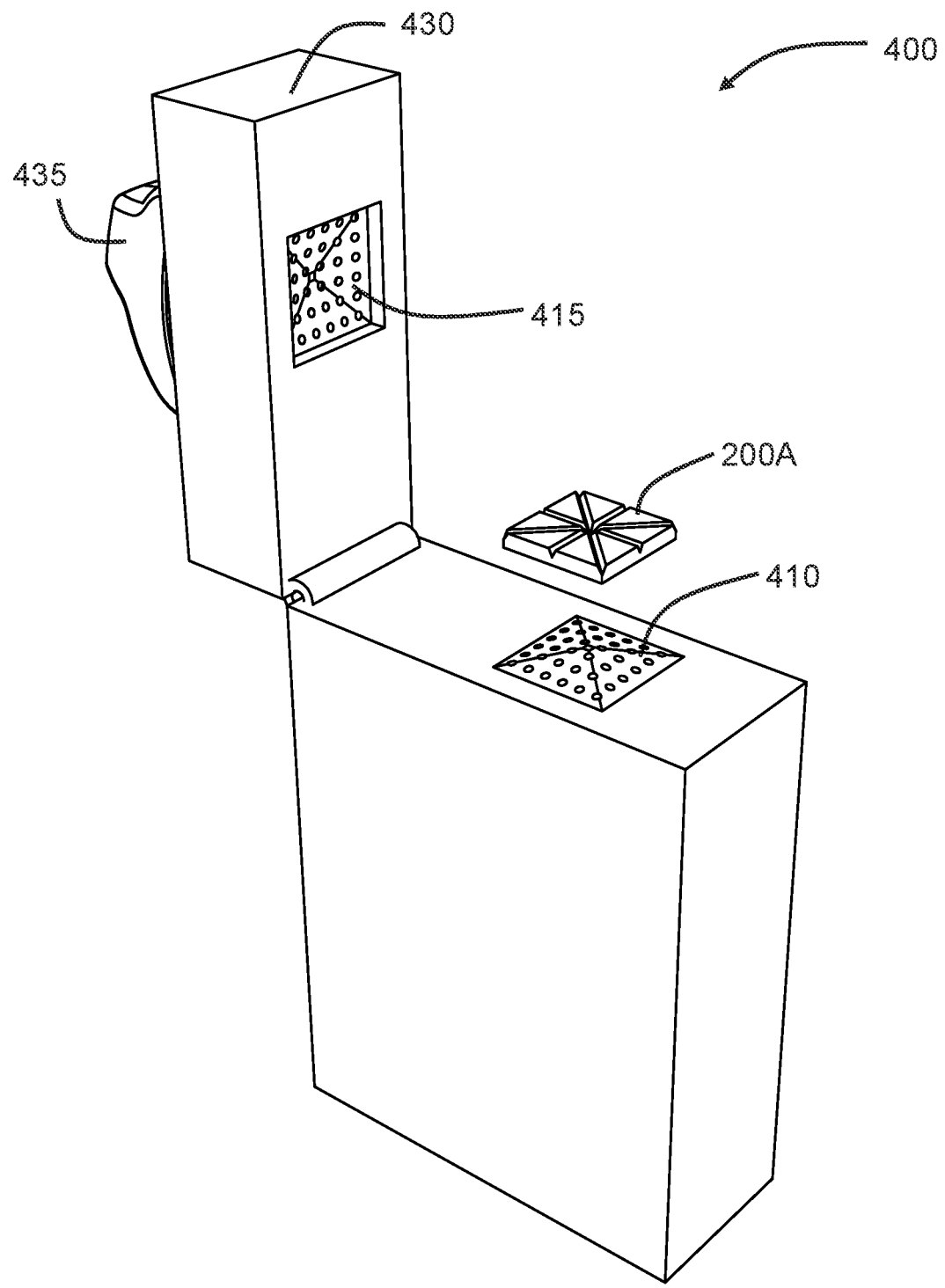
FIG. 4A is a top perspective view of an example vaporization device with a lid in an open position in accordance with an embodiment.
Figure 4B:
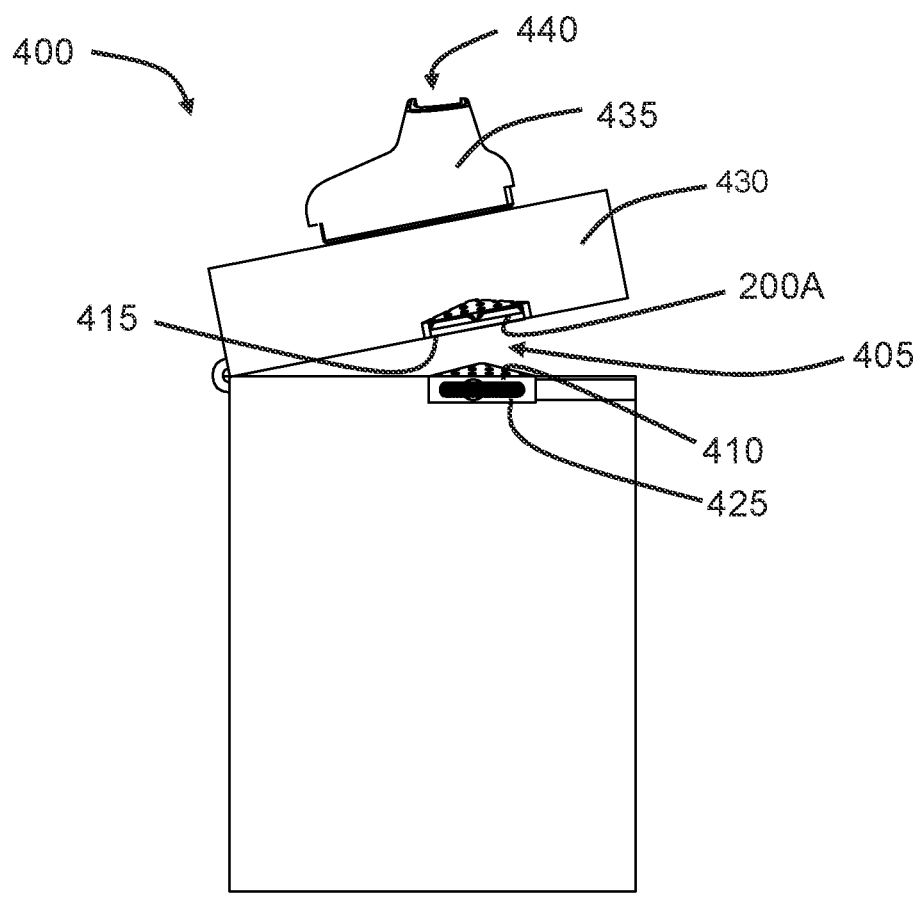
FIG. 4B is a side view of the vaporization device of FIG. 3H with the lid in a partially open position in accordance with an embodiment.
Figure 4C:
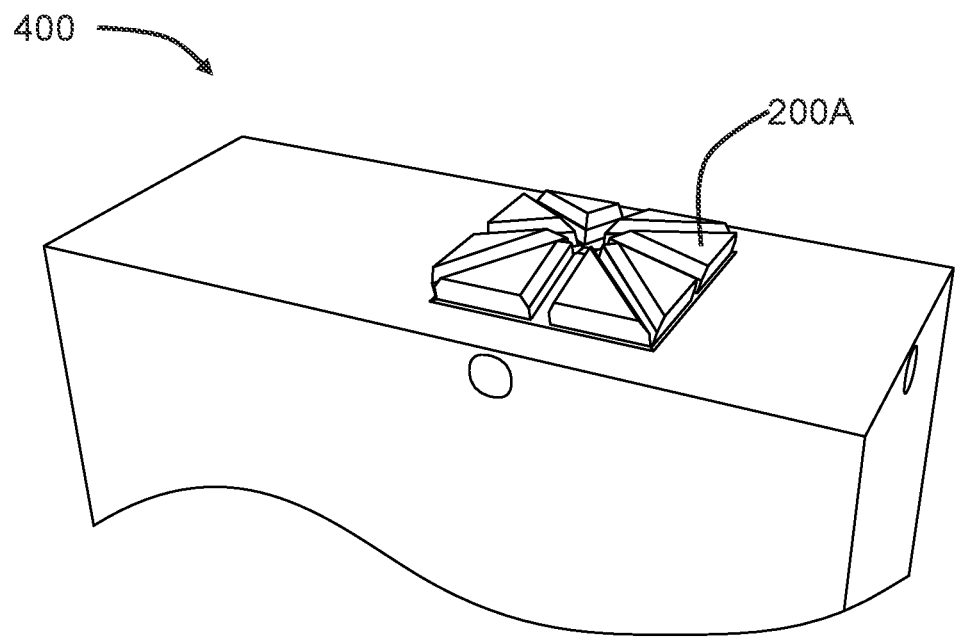
FIG. 4C is a cut-away perspective view of a tablet positioned in the heating chamber of the vaporization device of FIG. 3H in accordance with an embodiment.

Referring to FIGS. 4A-4C, shown therein is an example vaporization device 400 in accordance with an embodiment. The vaporization device 400 shown in FIGS. 4A-4C is an example of a vaporizer configured to compress a phyto material tablet. The vaporization device 400 may also fracture a phyto material tablet, such as tablets 200, into multiple pieces. This may facilitate operation of a convection heating assembly.

The vaporization device 400 includes a heating chamber 405. A tablet 200 can be positioned in the heating chamber 405 to be vaporized. The heating chamber 405 can include one or more heating elements. In general, the heating elements can be selected to provide thermal energy to the heating chamber 405 to heat the phyto material tablet 200 to a predetermined vaporization temperature (or temperatures) to cause the tablet 200 to be vaporized. The vapor released by vaporizing the tablet 200 can be inhaled by a user through the inhalation aperture 440 provided on mouthpiece 435.

In some cases, as shown in FIG. 4B, the heating chamber 405 may include one or more convection heating elements 425. In other cases, the heating chamber 405 may include one or more conduction heating elements. In yet other cases, the heating chamber 405 may include at least one convection heating element and at least one conduction heating element.

In some cases, the heating chamber 405 can include a convection heating element 425 as shown in FIG. 4B. The convection heating element 425 can be used to heat air passing therethrough to a predetermined temperature. This heated air can then pass through a phyto material tablet 200 positioned in the heating chamber 405. The predetermined temperature can be selected to heat the phyto material tablet 200 sufficiently to vaporize the phyto material tablet 200.

The heating chamber 405 can include at least structural feature such as a rib or protrusion or pointed pyramid shape usable to apply a directed force at various locations on a surface of a phyto material tablet 200 inserted in the heating chamber. The structural feature may be shaped to apply the directed force with varying levels across the surface of the phyto material tablet 200. This may fracture the tablet 200.

The inside walls of the heating chamber 405 can be shaped to facilitate fracturing the phyto material tablet 200. For instance, as shown in FIG. 4B, the lower wall or bottom surface 410 of the heating chamber 405 is pyramid shaped (here shown as a rectangular pyramid). When a tablet 200 is positioned on the bottom surface 410 of the heating chamber 405 and a downward force is applied, the pyramid shaped bottom surface 410 may facilitate the fracturing of the tablet 200 by applying an unevenly distributed force to the lower surface 230 of the tablet 200.

In some examples, as shown, the top surface 415 of the heating chamber 405 may also be shaped to facilitate fracturing the tablet 200. For example, as shown in FIGS. 4A and 4B, the top surface 415 has a recess that is shaped to correspond to the pyramid shaped bottom surface 410.

When the lid 430 of the device 400 is closed, the top surface 415 and bottom surface 410 of the heating chamber 405 combine to apply force to the top surface 225 and bottom surface 230 of tablet 200 respectively. However, the force is not applied evenly across the surface 210 of the tablet 200, due to the shape of the heating chamber 405. As a result, the mechanical force can cause the tablet 200 to bend, and ultimately break. When the tablet includes break regions, the reduced structural integrity in those break regions can induce the tablet 200 to break into pieces along those break regions.

In some cases, the tablet 200 may not fracture completely. However, the mechanical force applied by the top surface 415 and bottom surface 410 of the heating chamber 405 may still cause the tablet 200 to deform along the break regions.

FIG. 4B illustrates the lid 430 of the vaporization device 400 being closed. A tablet 200A positioned in the heating chamber 405 can be fractured as a result of the lid 430 being closed. As the lid 430 is closed, the tablet 200A can be compressed within the heating chamber 405. The inner surfaces 410/415 of the heating chamber 405 can apply variable forces on the tablet 200A to fracture or crush the tablet 200A. This can increase the exposed surface area of the tablet to facilitate vaporization.

As mentioned, one or more of the inner surfaces of the heating chamber 405 may include a fracturing region. The fracturing region may be non-planar (e.g. textured, triangular, curved/dome shaped) or may include protrusions. The fracturing region may apply a variable force to a phyto material tablet 200A when the tablet is pushed onto that surface. For example, the upper surface 415 or base 410 of the vaporization chamber 405 may be configured to press the phyto material tablet into the opposing surface of the vaporization chamber 405. One or both of the upper surface 415 and base 410 can be shaped to apply a variable force across the surface of the tablet 200. This variable force may induce the phyto material tablet 200 to break into pieces, exposing a larger surface area of the phyto material tablet 200 for vaporization.

In some examples, the heating chamber 405 may be heated to facilitate fracturing the tablet 200. For example, once the phyto material tablet 200 is loaded into the heating chamber 405, the heating element 425 may be activated. In some cases, a user may enable activation of the heating element 425 using input controls. For instance, a user may operate an activation switch to enable the heating element 425 to be activated (or deactivated).

The heating element 425 may heat one or more of the inner walls of heating chamber 405 that contact the tablet 200A. Heating the tablet 200A may facilitate fracturing the tablet 200A in addition to the mechanical forces applied to the tablet 200A when the lid 430 is closed. For instance, the heating element 425 may heat the lower surface 410 of the heating chamber 405. This, in turn, can heat the bottom surface 230 of the tablet 200 to facilitate breaking of the tablet.

FIG. 4C illustrates an example of the phyto material tablet 200A after being fractured by the vaporization device 400. As shown in FIG. 4C, an increased surface area of the tablet 200A is exposed when the tablet is fractured. This may expose a greater proportion of the tablet 200 to heated air passing through the heating element 425. This may also provide additional air channels for heated air to flow through the tablet 200A and to inhalation aperture 440.

Referring now to FIGS. 5A-5I, shown therein is another example of a vaporization device 500 in accordance with an embodiment. Vaporization device 500 is an example of a vaporization device that may be used with a dispensing magazine 550. A dispensing magazine 550 including a plurality of tablets 200 may be inserted into the vaporization device 500. The vaporization device 500 may then insert the tablets individually into a heating chamber 505 for vaporization.

The vaporization device 500 can include a transport mechanism 560. The transport mechanism 560 can be used to transport one or more tablets 200 from the dispensing magazine 550 to the heating chamber 505 for vaporization.

As with vaporization device 400, the vaporization device 500 includes a heating chamber 505. However, in vaporization device 500, although the base 510 of the heating chamber 505 remains constant, the top surface 515 changes as the transport mechanism 560 is rotated. That is, the heating chamber 505 may be formed from the base 510 and the first top surface 515A or from the base 510 and the second top surface 515B.

Figure 5B:
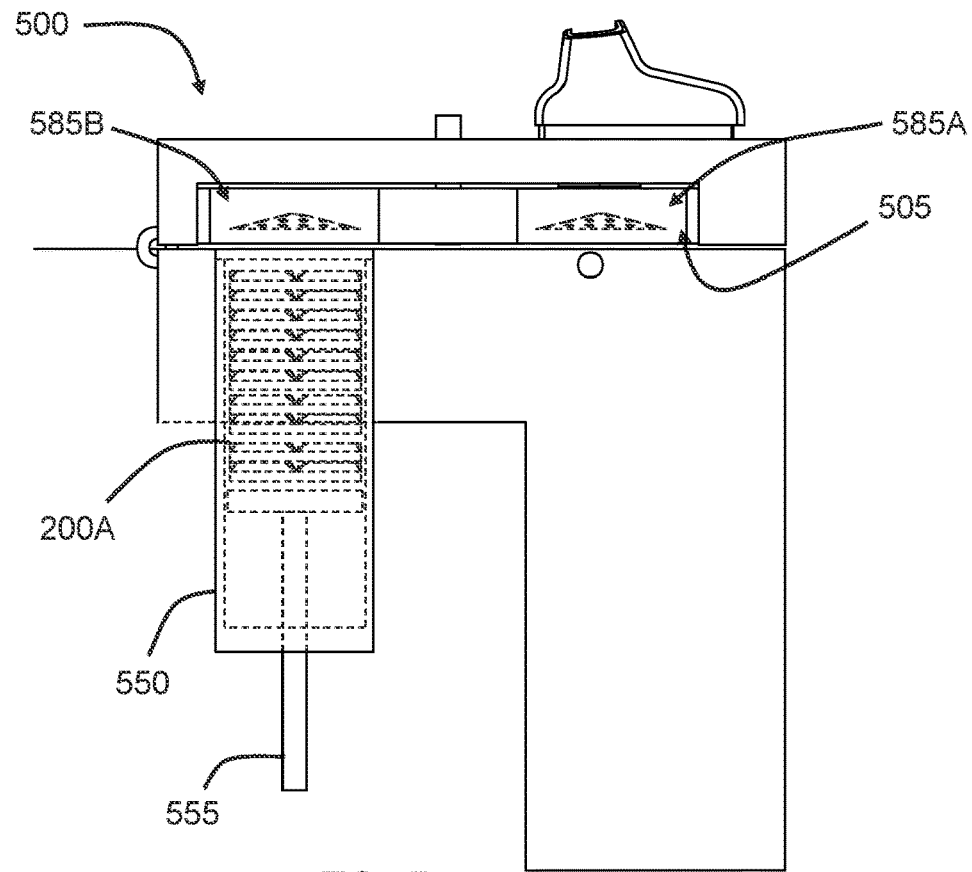
FIG. 5B is a cut-away side view of the example vaporization device shown in FIG. 5A in accordance with an embodiment.

The transport mechanism 560 may receive a tablet 200 from the dispensing magazine 550. For instance, as shown in FIG. 5B, a tablet 200 may be received in tablet region 585B when the transport mechanism 560 is in a first orientation. In the first orientation, tablet region 585B may be aligned with (e.g. overlie) the dispensing magazine 550. Accordingly, a tablet 200 may be directed into tablet region 585B by the dispensing magazine 550.

In the first orientation, the tablet region 585A may be aligned with the base 510 of heating chamber 505. Accordingly, the tablet region 585A may define the top surface 515 of the heating chamber 505 in the first orientation.

The transport mechanism 560 may then rotate (see e.g. FIG. 5G) to a second orientation. In the second orientation, the tablet region 585B may be aligned with the base 510 of heating chamber 505. Accordingly, the tablet region 585B may define the top surface 515 of the heating chamber 505 in the first orientation. The tablet 200 inserted into the tablet region 585B may then be vaporized in the heating chamber 505.

In the second orientation, tablet region 585A may be aligned with (e.g. overlie) the dispensing magazine 550. Accordingly, a tablet 200 may be directed into tablet region 585A by the dispensing magazine 550.

Figure 5F:
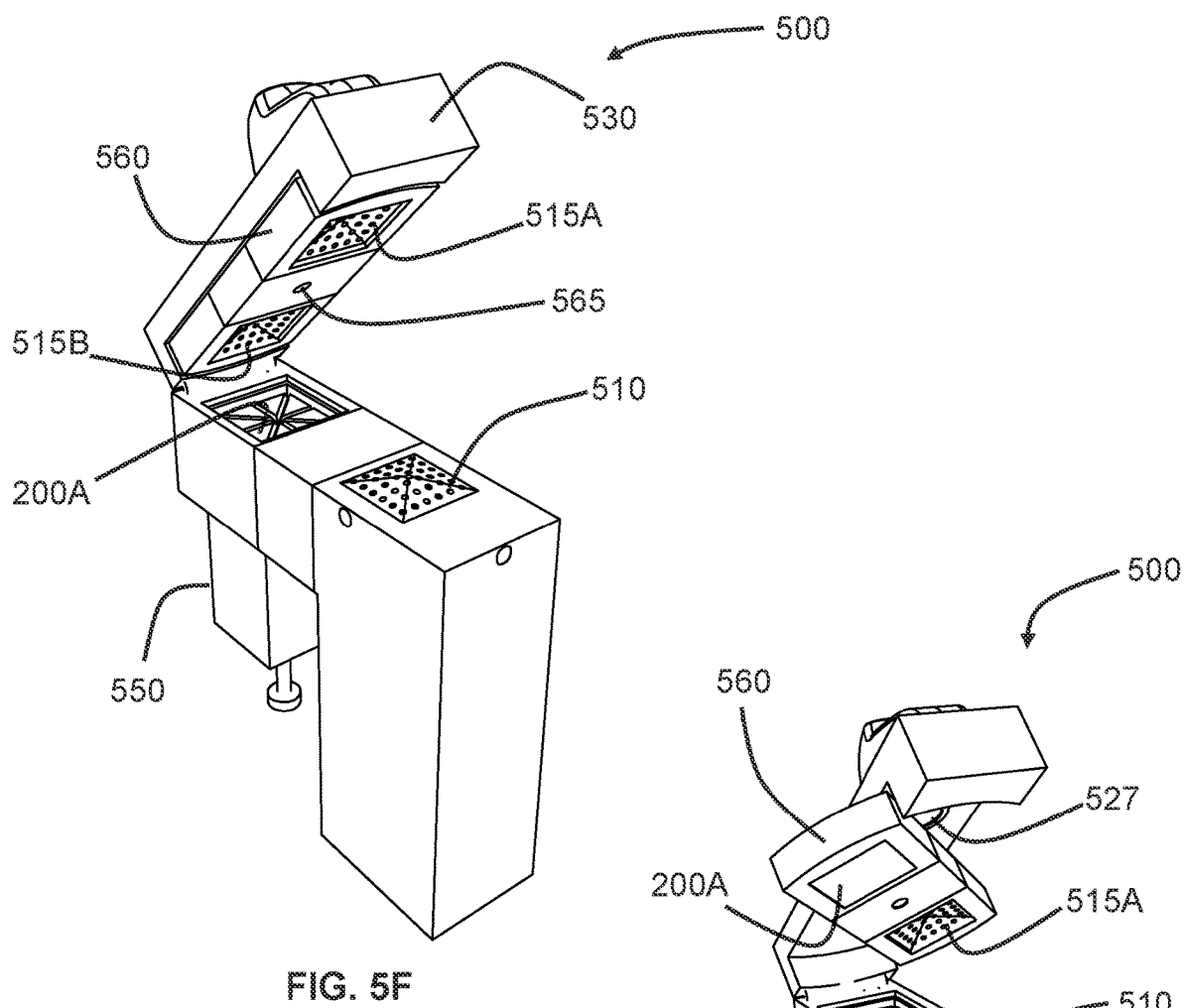
FIG. 5F is a top perspective view of the example vaporization device shown in FIG. 5A with the lid in an open position in accordance with an embodiment.
Figure 5G:
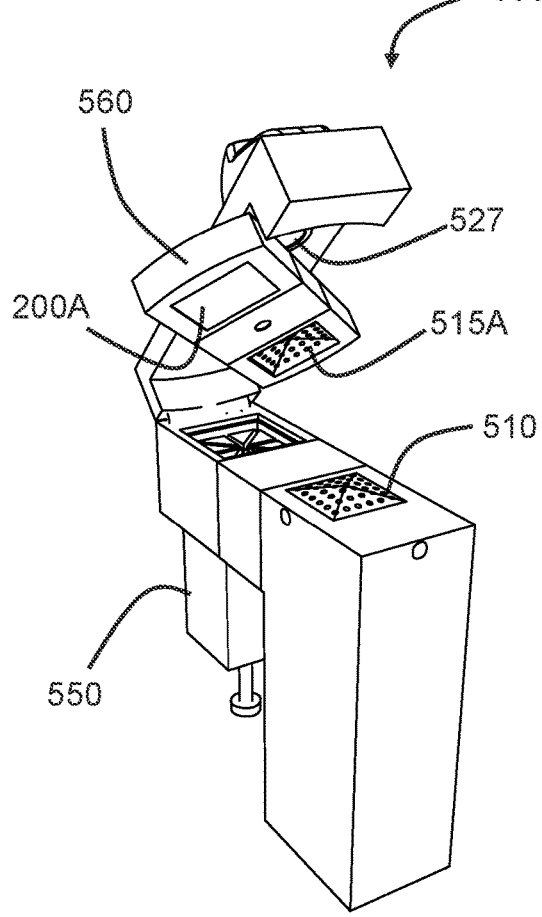
FIG. 5G is a top perspective view of the example vaporization device shown in FIG. 5A with the lid in the open position showing an example transport mechanism in accordance with an embodiment.

As shown in FIGS. 5F and 5G, the lid 530 of the vaporization device 500 may be open when the transport mechanism 560 is rotated between the first orientation and the second orientation. Accordingly, in some embodiments, the top surface of the tablet region 585B and the bottom surface 510 may also interact to fracture the tablet 200 received in tablet region 585B when the lid 530 is closed (in a manner analogous to vaporization device 400). The lid 530 can be coupled to the base 510 of the heating chamber by a pivotable coupling 506 such as a hinge.

In other embodiments, the vaporization device may remain closed while the transport mechanism is rotated. This may reduce the possibility of the tablet 200 being lost while moving from the dispensing magazine 550 to the heating chamber 505.

When a tablet 200 is positioned in the heating chamber 505, one or more heating elements can be activated (as discussed above with reference to FIG. 4). A user may operate a control input 537 to enable the heating element(s) to become active. When the tablet 200 is vaporized, vapor can pass through the upper surface 515A of the heating chamber 805 and enter vapor inlet 527. The vapor may be drawn into the vapor inlet 527 by a user inhaling from inhalation aperture 540. A user can then inhale the released vapor through aperture 540.

As shown in FIG. 5B, the dispensing magazine 550 can a fresh phyto material tablet 200 into the tablet region 585B. As shown in FIG. 5C, the dispending magazine 550 can include a dispensing plunger 555 that pushes the tablet 200 into tablet region 585B. The plunger 555 may also include a plate 556 to push the tablets 200 from the base 552 of the magazine 550 towards the top 554 of the magazine 550. The plunger applies an upward (relative to the base 552 of the magazine) force to the plurality of phyto material tablets 200 held in the magazine 550 to facilitate loading into the vaporization device 500. The tablets 200 may then pass through the top 554 and into the tablet region 585.

In some cases, the plunger 555 may include a ratchet mechanism to ensure that only one tablet 200 is loaded at a given time. However, this may be omitted in other examples.

In some cases, the plunger 555 may be operated manually by a user of the vaporization device 500 to insert a tablet 200 into the tablet region 585. Alternatively, the plunger 555 may include an automatic insertion mechanism. For example, as shown in FIG. 5E, a spring 555B may be used to push the plunger towards the top 554 of the magazine 550 and in turn push the tablets 200.

FIG. 5F illustrates the vaporization device 500 with the lid 530 opened. This may facilitate manually removing a spent phyto material tablet 200. When the lid 530 is opened, the phyto material tablet 200 in tablet region 585A can be removed from the heating chamber 505. For instance, the tablet 200 may be removed manually e.g. by hand or by using a brush. A subsequent phyto material tablet 200 can already be loaded into the tablet region 585B for movement into the heating chamber 505 via transport mechanism 560.

FIG. 5G illustrates the transport mechanism 560 being rotated to transport phyto material tablet 200A into the heating chamber 505. As shown here, the transport mechanism 560 can rotate about a rotation axis 565 to move the tablet 200 into the heating chamber 505.

Figure 5H:
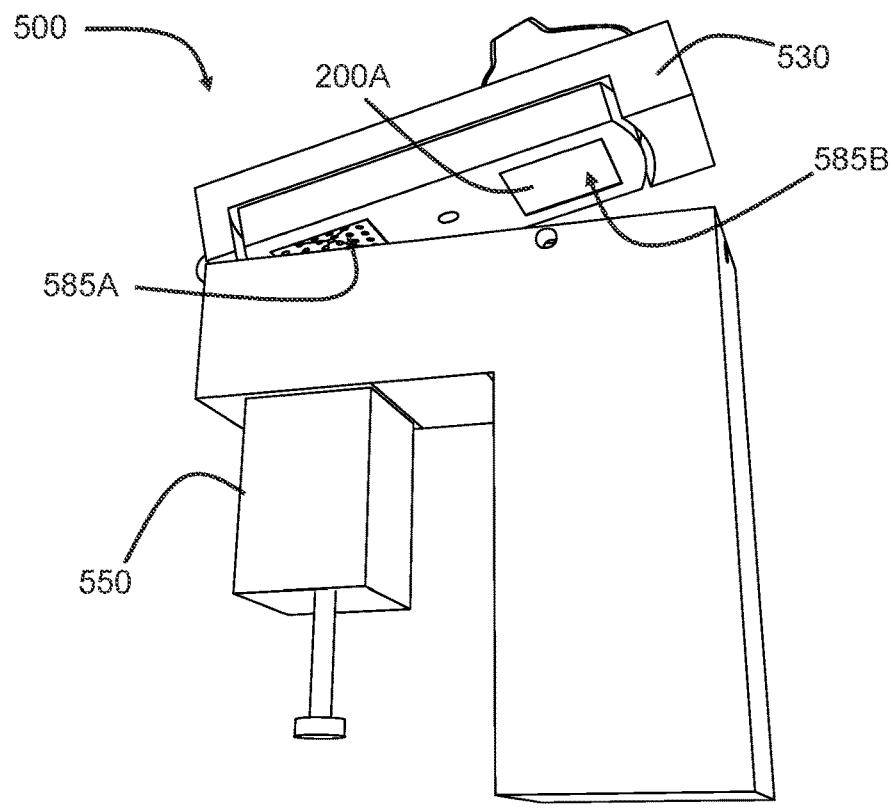
FIG. 5H is a bottom perspective view of the example vaporization device shown in FIG. 5F with the lid in a partially open position in accordance with an embodiment.
Figure 5I:
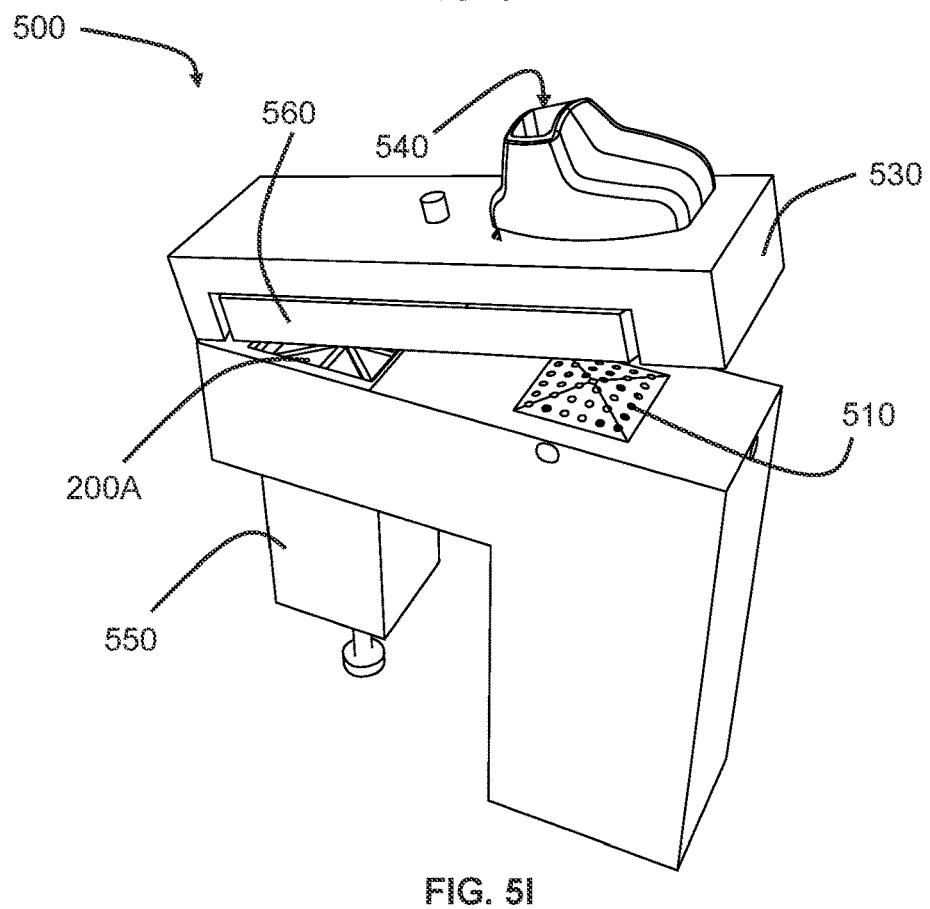
FIG. 5I is a top perspective view of the example vaporization device shown in FIG. 5F with the lid in a partially open position in accordance with an embodiment.
Figure 5J:
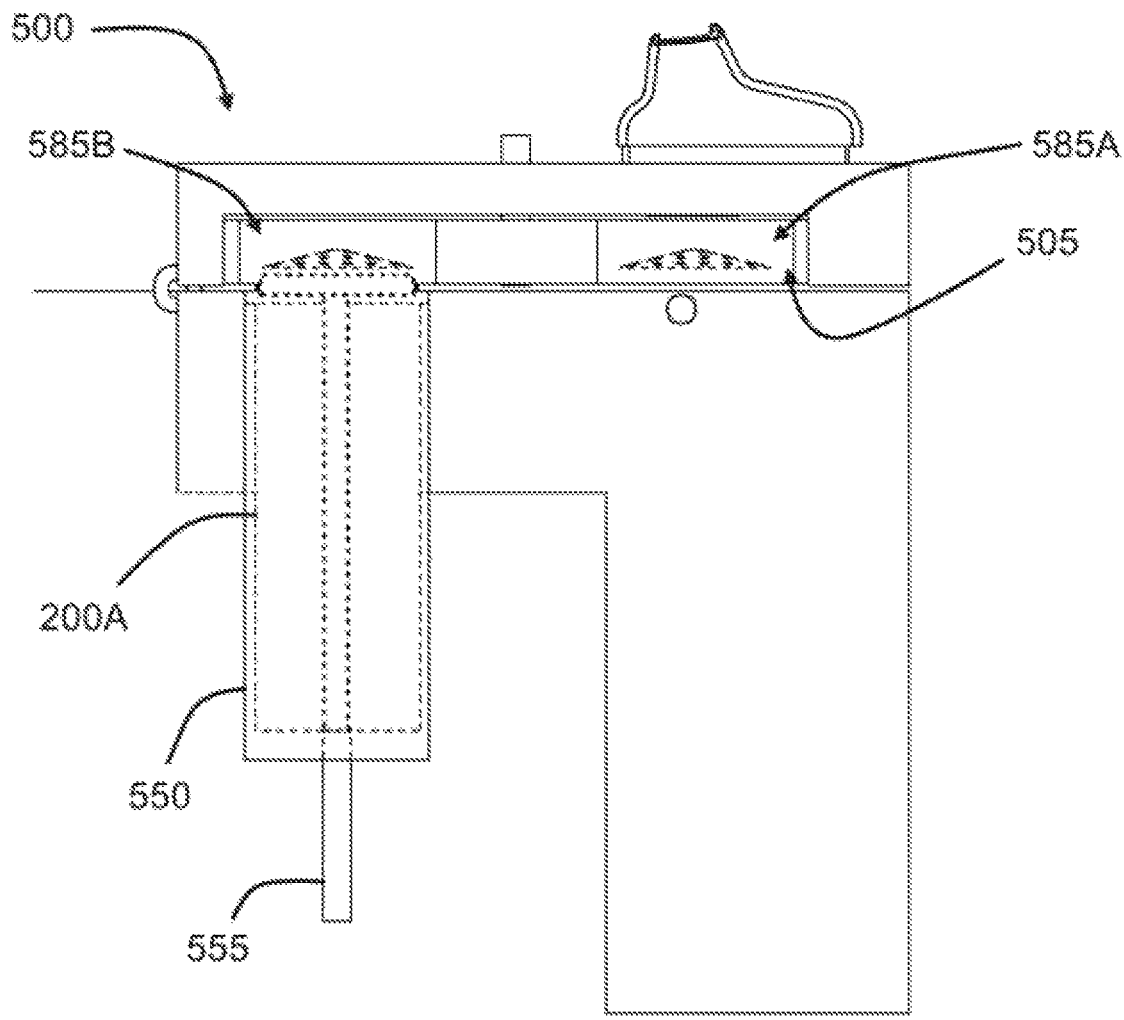
FIG. 5J is a cut-away side view of the example vaporization device shown in FIG. 5A with the plunger extending into the tablet region in accordance with an embodiment.

FIGS. 5H and 5I illustrate the transport mechanism 560 in the second orientation with the tablet 200 aligned with the heating chamber base 510. The lid 530 is shown about to be closed to position the tablet 200 in the heating chamber 505. As mentioned, closing the lid 530 may also fracture the phyto material tablet 200 within the heating chamber 505 to increase the exposed surface area for vaporization.

In some examples, one or more surfaces of the heating chamber may include additional tablet fracturing features. For instance, the top surface of the heating chamber may be rotatable a central axis to facilitate fracturing by adjusting the locations at which force is applied to the phyto material tablet 200 if one of the surfaces of the heating chamber is asymmetric. In some embodiments, a user may manually rotate the top surface. In other embodiments, the vaporization device may include a motor to rotate the top surface.

FIGS. 6A-6E illustrates another example vaporization device 600 in accordance with an embodiment. The vaporization device 600 includes another example of a transport mechanism 660 that can be used to load phyto material tablets 200A from a dispensing magazine 650 into a heating chamber 605. When the tablet 200A is positioned in the heating chamber 605, the tablet 200A can be vaporized by a user of device 600.

The transport mechanism 660 is an example of a transport mechanism having a circular path. The transport mechanism can be used to receive a phyto material tablet from a dispensing magazine housing a plurality of phyto material tablets and to transport the phyto material tablet into the heating chamber in a rotational motion about the dispensing magazine. The dispensing magazine may have a proximal end and a distal end and wherein the phyto material tablets can be dispensed from the proximal end. The transport mechanism can surround the dispensing magazine.

The dispensing magazine 650 may be inserted into the device 600 aligned with the heating chamber 605. However, the top 654 of dispensing magazine 650 may be displaced from, and face away from the heating chamber 605. In some cases (not shown), the transport mechanism 660 can include multiple tablet regions 685 that rotate around the dispensing magazine 650 in a circular path.

The transport mechanism 660 can receive a phyto material tablet 200A from the dispensing magazine 650. The transport mechanism 660 may then transport the phyto material tablet 200A into the heating chamber 605 in a rotational motion about the dispensing magazine 650.

FIGS. 6A-6E illustrate an example transport mechanism 660 with a circular cross-section in the form of a circular belt or cylinder. In other cases, the transport mechanism 660 may pivot proximate the transport mechanism bottom 652.

The belt/cylinder may have a first diameter. The transport mechanism 660 may be manufactured of materials that do not off gas at the predetermined vaporization temperature, such as steel or various high performance thermoplastics or a belt formed from ceramic segments, (e.g. similar to a watch band). A shield 662, also with a circular cross-section, may be disposed on an outside of the transport mechanism 660 having a second diameter that is larger than the first diameter (see e.g. FIG. 6E). For instance, the transport mechanism 660 and the shield 662 may be concentric.

The phyto material tablet can be loaded into the circular belt or cylinder. If the tablet is substantially planar, the tablet can be fractured between the transport mechanism 660 and the shield 662. Positioning a substantially planar tablet between the transport mechanism and the shield (each having circular cross-sections may facilitate breaking the tablet into multiple pieces. In some cases, the vaporization devices shown in FIGS. 6A-6D may include additional fracturing components, such as the shaped heating chambers described above with references to FIGS. 4 and 5.

Figure 6A:
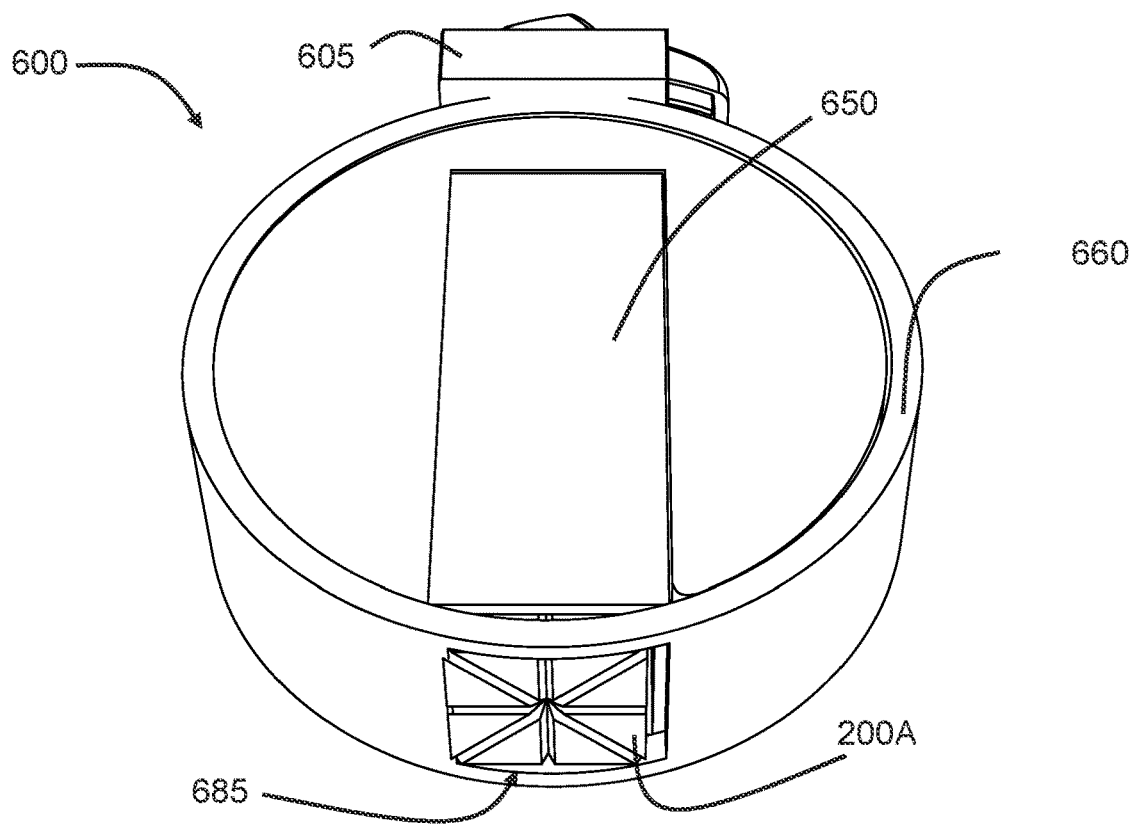
FIG. 6A is a bottom perspective view of an example vaporization device in accordance with an embodiment with an example transport mechanism in a first position.
Figure 6B:
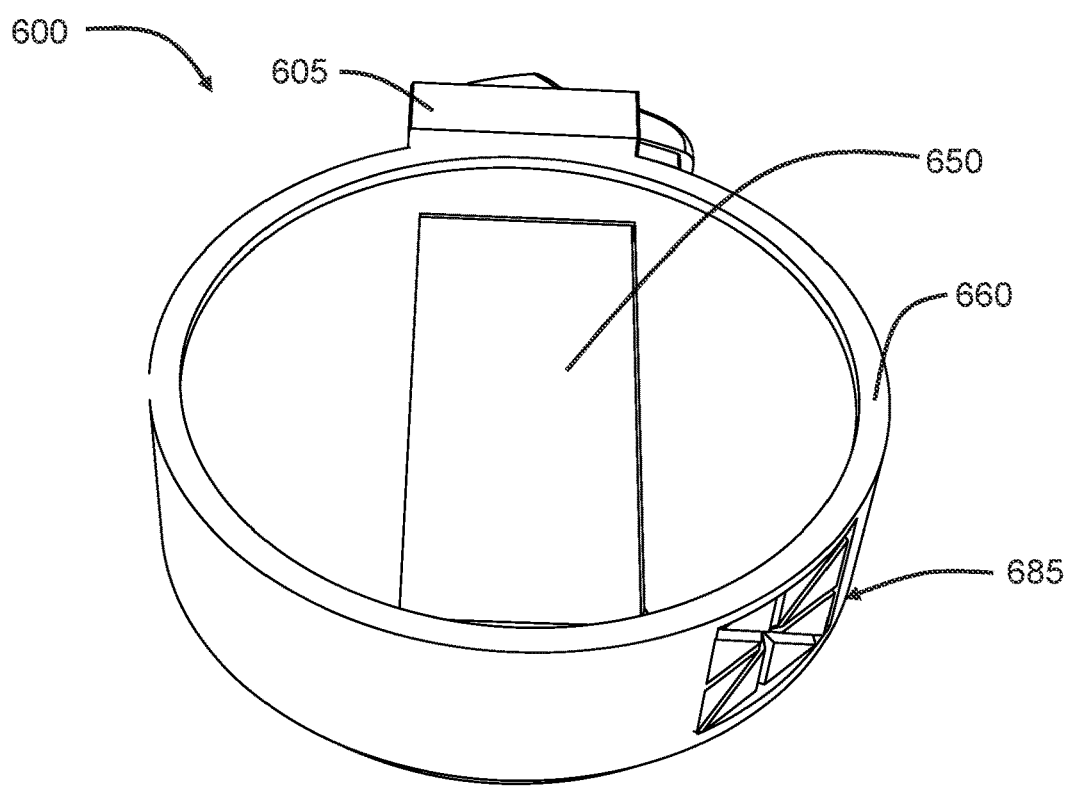
FIG. 6B is a bottom perspective view of the vaporization device of FIG. 6A with the transport mechanism in an intermediate position in accordance with an embodiment.
Figure 6C:
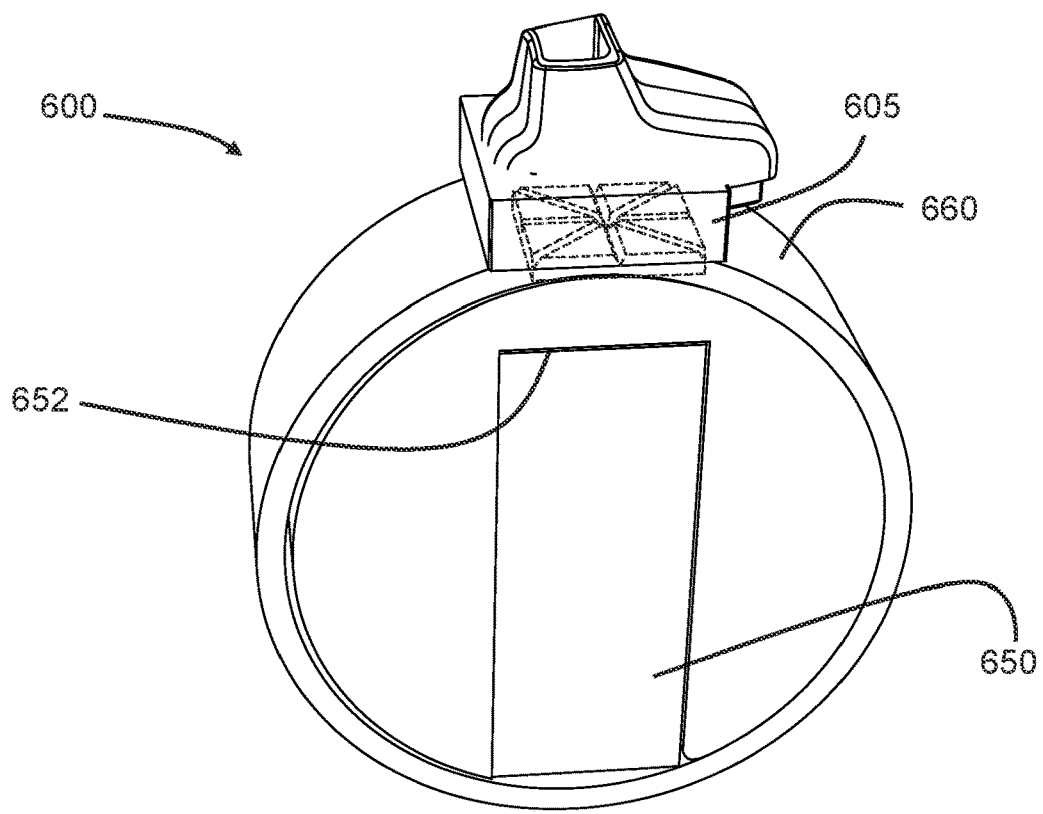
FIG. 6C is a top perspective view of the vaporization device of FIG. 6A with the transport mechanism in a tablet vaporization position in accordance with an embodiment.
Figure 6D:
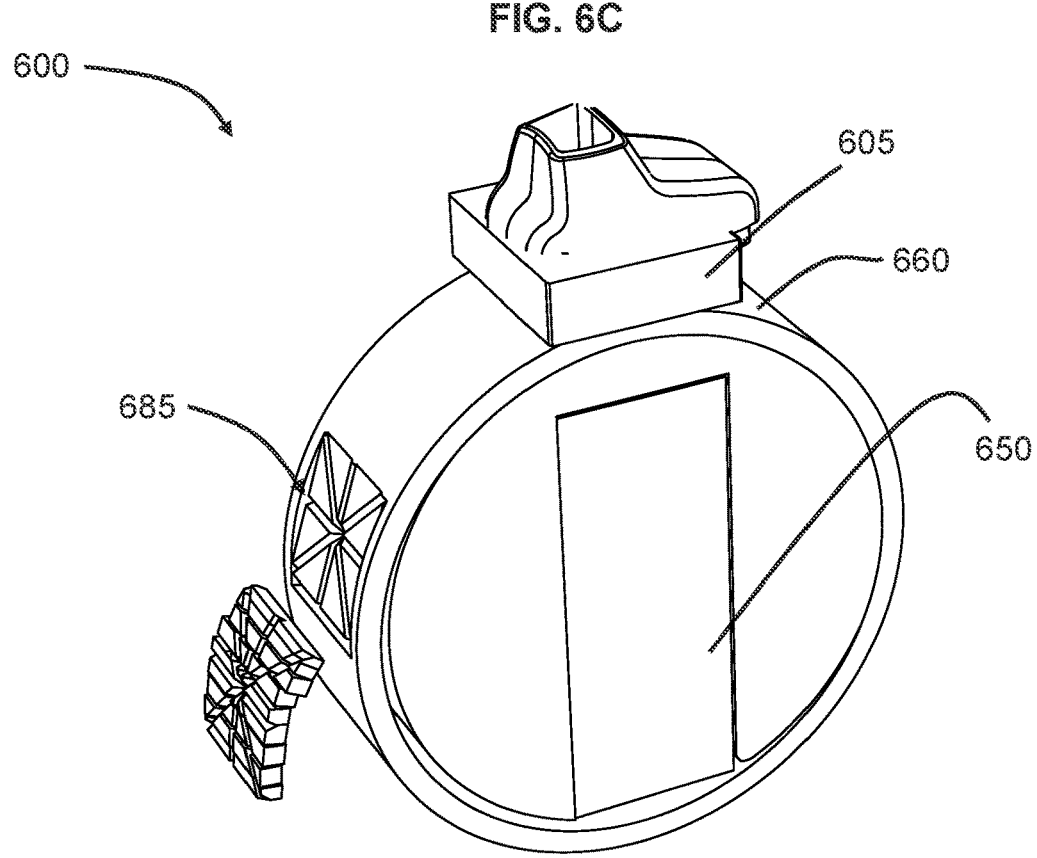
FIG. 6D is a top perspective view of the vaporization device of FIG. 6A with the transport mechanism in a tablet ejection position in accordance with an embodiment.
Figure 6E:
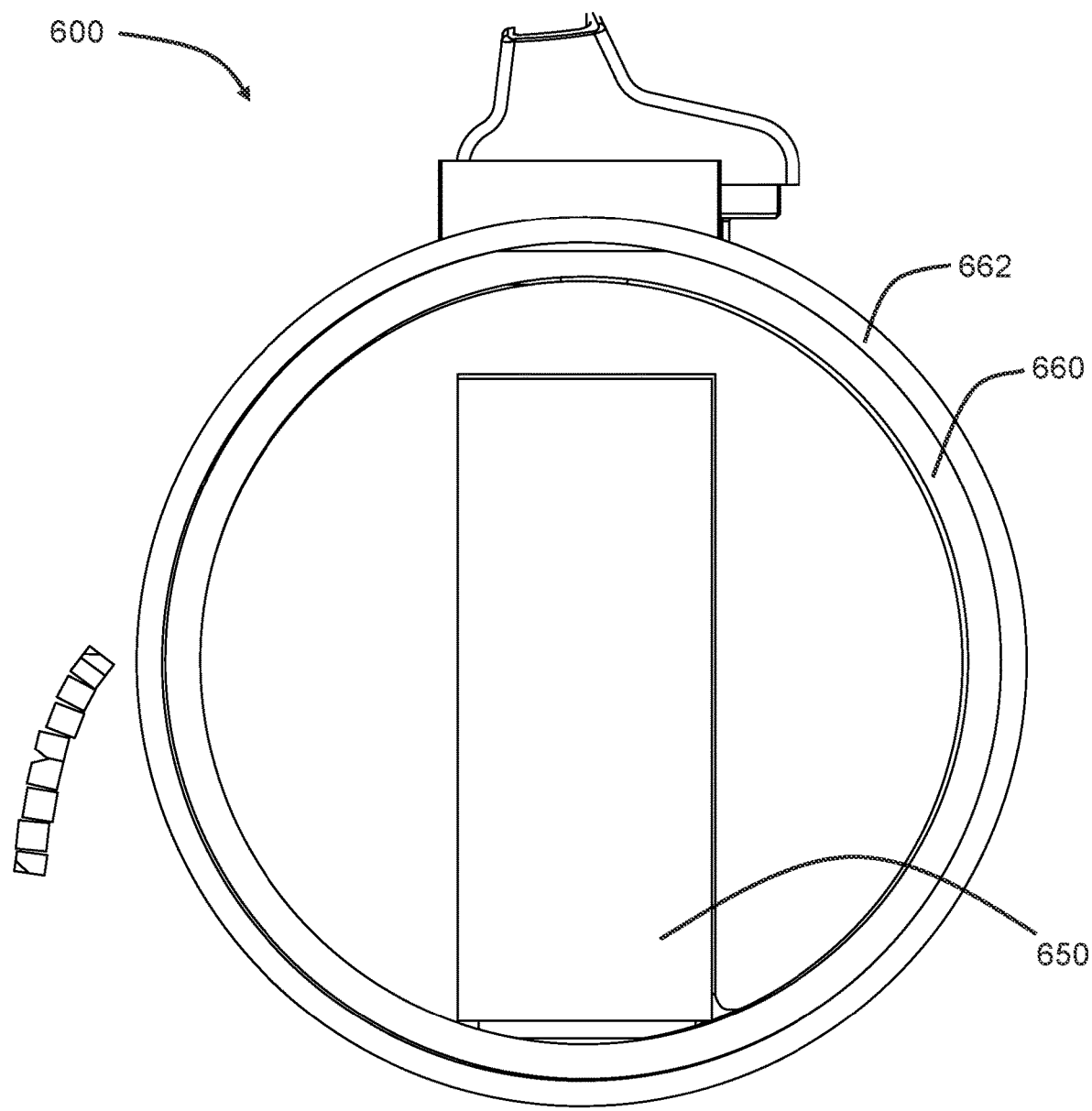
FIG. 6E is a cut-away front view of the vaporization device of FIG. 6D with the transport mechanism in the tablet ejection position.

Upon vaporization of the phyto material tablet, the transport mechanism can be rotated and the vaporized phyto material tablet can be ejected from the vaporization device (see e.g. FIGS. 6D and 6E).

Figure 8A:
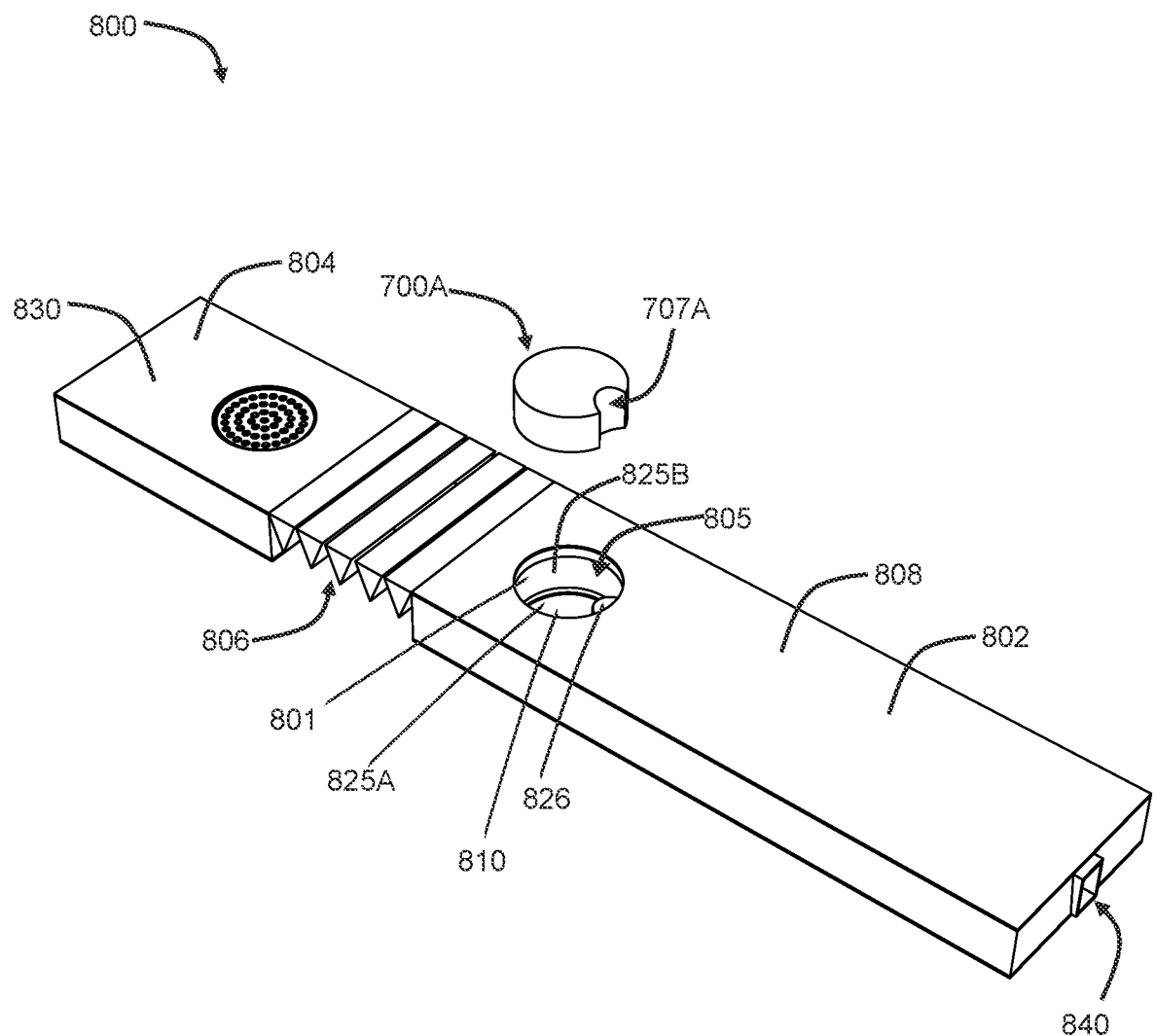
FIG. 8A is a bottom perspective view of an example vaporization device having a heating chamber retainer in an open position and the lid in an open position in accordance with an embodiment.

Referring now to FIGS. 8A-8G, shown therein is another example embodiment of a vaporization device 800. As shown in FIG. 8A, the vaporization device 800 can include a heating chamber 805. The heating chamber 805 can be shaped to receive a generally circular phyto material tablet, such as phyto material tablet 700A. In other cases, the heating chamber 805 may be shaped to receive other shapes of tablets.

The vaporization device 800 can include a first portion 802 that and a second portion 804. The second portion 804 can include the lid 830 of the heating chamber 805. The second portion 804 can be moveably mounted to the first portion 802, for example by a pivotable coupling such as hinge section 806. The second portion 804 may be moved between a first position (shown in FIG. 8A) in which the lid 830 of the heating chamber 805 is open, and a second position (shown in FIG. 8B) in which the lid 830 of the heating chamber 805 is closed.

The first position may allow a user to insert a phyto material tablet 700A into the heating chamber 805. The first position may also allow a user to extract or discard a used or spent phyto material tablet 700A. In the example shown in FIG. 8A, a phyto material tablet may be inserted into the heating chamber 805 from the underside of the vaporizer 800.

In the second position, the heating chamber 805 can be heated to vaporize a phyto material tablet 700A positioned therein. The vapor emitted from heating the phyto material tablet 700A can be drawn into the vapor inlet 827 by a user inhaling through inhalation aperture 840. Vapor emitted from the heating chamber 805 can pass through the vapor inlet 827 through fluid pathway 842 to the inhalation aperture 840.

The lid 830 of the vaporization device 800 may include an air inlet 841. The air inlet 841 may can be fluidly coupled to the heating chamber 805. When a user inhales from the inhalation aperture 840, air can be drawn into the air inlet 841 and through the heating chamber 805 to mix with the vapor emitted therein and travel to the inhalation aperture 840.

As shown in FIGS. 8A, 8D, 8E and 8G the heating chamber 805 can include a protrusion 826 that extends partially into the heating chamber 805. The side of the protrusion 826 facing into the heating chamber 805 can include the vapor inlet 827. The protrusion 826 may provide a larger vaporization inlet 827 for the heating chamber 805.

In some cases, the protrusion 826 may correspond to a recess 707A of the phyto material tablet 700A. In other cases, generally circular phyto material tablets may be used with the vaporization device 800. In some such cases, the protrusion 826 may serve to fracture a portion of the phyto material tablet inserted therein.

In some cases, a phyto material tablet such as tablet 700A may be formed with a variable density. For example, the portion of the tablet 700A proximate the recess 707A may be less densely packed than the other side of the tablet 700A opposite the recess 707A. Positioning a tablet 700A with a less densely packed portion proximate the vapor inlet 827 may facilitate the flow of vapor into the inlet 827. For example, the reduced density may allow small airflow channels to be present proximate the vapor inlet 827. In such cases, the protrusion 826 may enable registration of the less dense portion of a phyto material tablet proximate the vapor inlet 827.

The vapor inlet 827 may include a screen 828. The screen 828 may server to filter vapor entering the inlet 827, which may reduce the amount of phyto material inhaled by a user.

The heating chamber 805 of vaporization device 800 may include a plurality of heating elements. A first heating element 825A may be provided by the floor 810 of the heating chamber 805. Additionally, the inner sidewalls 801 of the heating chamber 805 may include a second heating element 825B. The second heating element 825B may substantially surround a phyto material tablet positioned in the heating chamber 805 (e.g. with the exception of the protrusion 826).

Heating a phyto material tablet on the sides and base may provide for more uniform vaporization of the phyto material. The plurality of heating elements 825 may also provide a more effective vaporization that is able to vaporize more of the phyto material positioned in the heating chamber 805.

The heating elements of heating chamber 805 can be arranged to conductively heat a tablet positioned in the heating chamber 805. Various types of conductive heating elements may be used, such as metallic and/or ceramic heating elements for example.

In some embodiments, the vaporization device 800B may include a tablet retainer 855. The tablet retainer 855 may be used insert a tablet into the heating chamber 805 and retain the tablet within the heating chamber 805. The tablet retainer 855 may operate as a sliding door to provide access to an underside of the heating chamber 805.

Figure 8B:
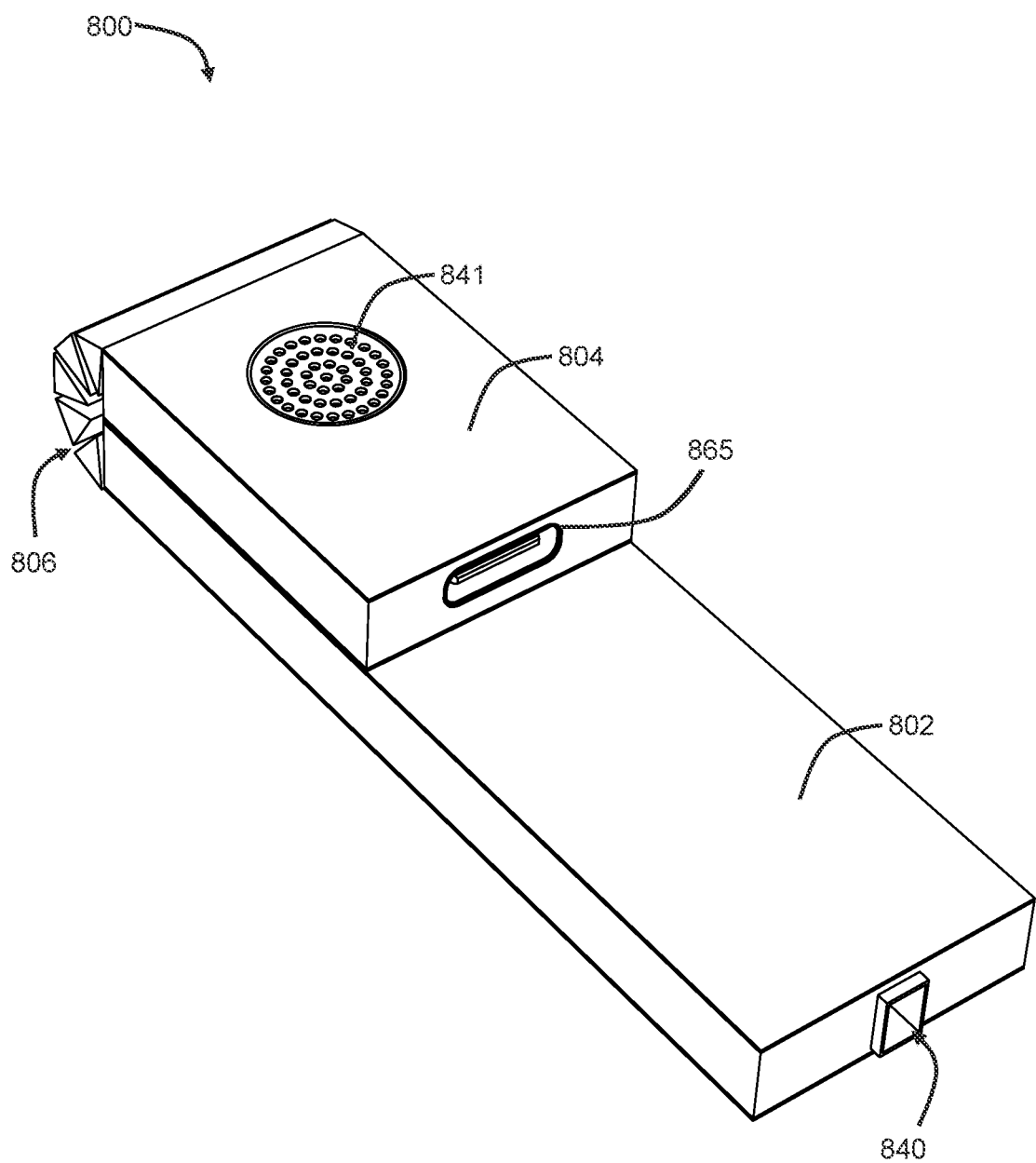
FIG. 8B is a top perspective view of the example vaporization device of FIG. 8A with the lid in a closed position in accordance with an embodiment.
Figure 8C:
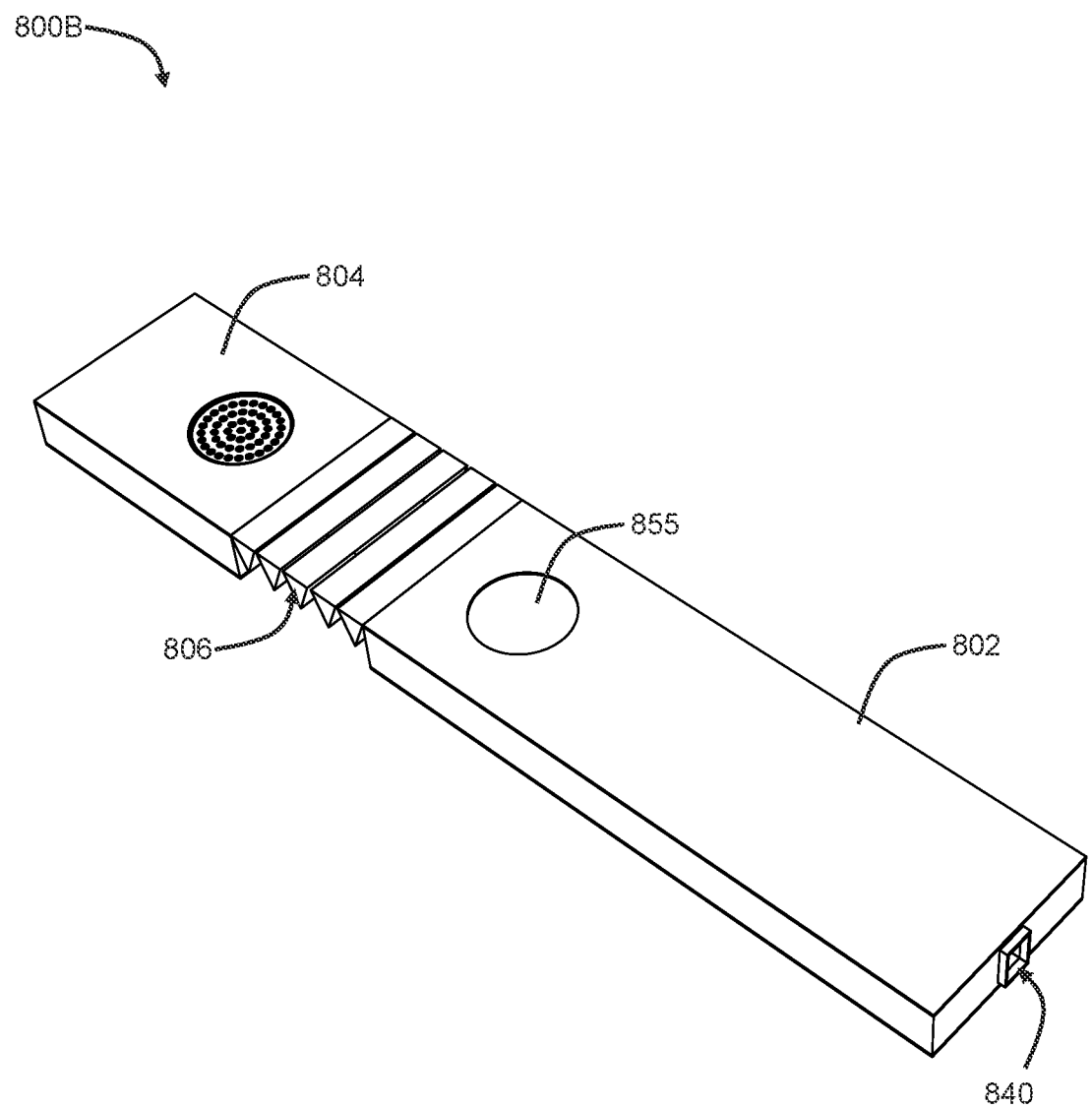
FIG. 8C is a bottom perspective view of the example vaporization device of FIG. 8A having a heating chamber retainer in a closed position and the lid in an open position in accordance with an embodiment.
Figure 8D:
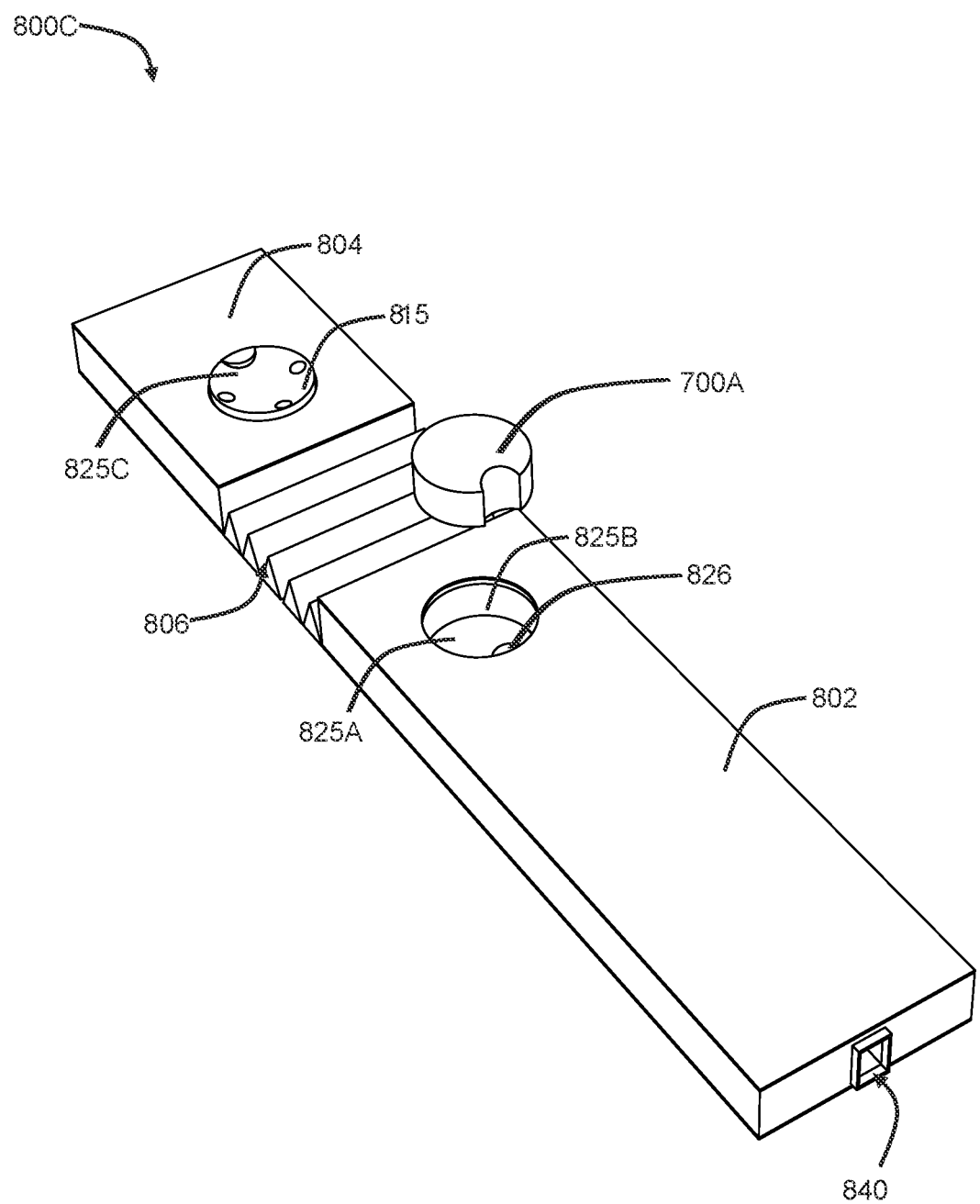
FIG. 8D is a top perspective view of the example vaporization device of FIG. 8A with the lid in an open position in accordance with an embodiment.
Figure 8E:
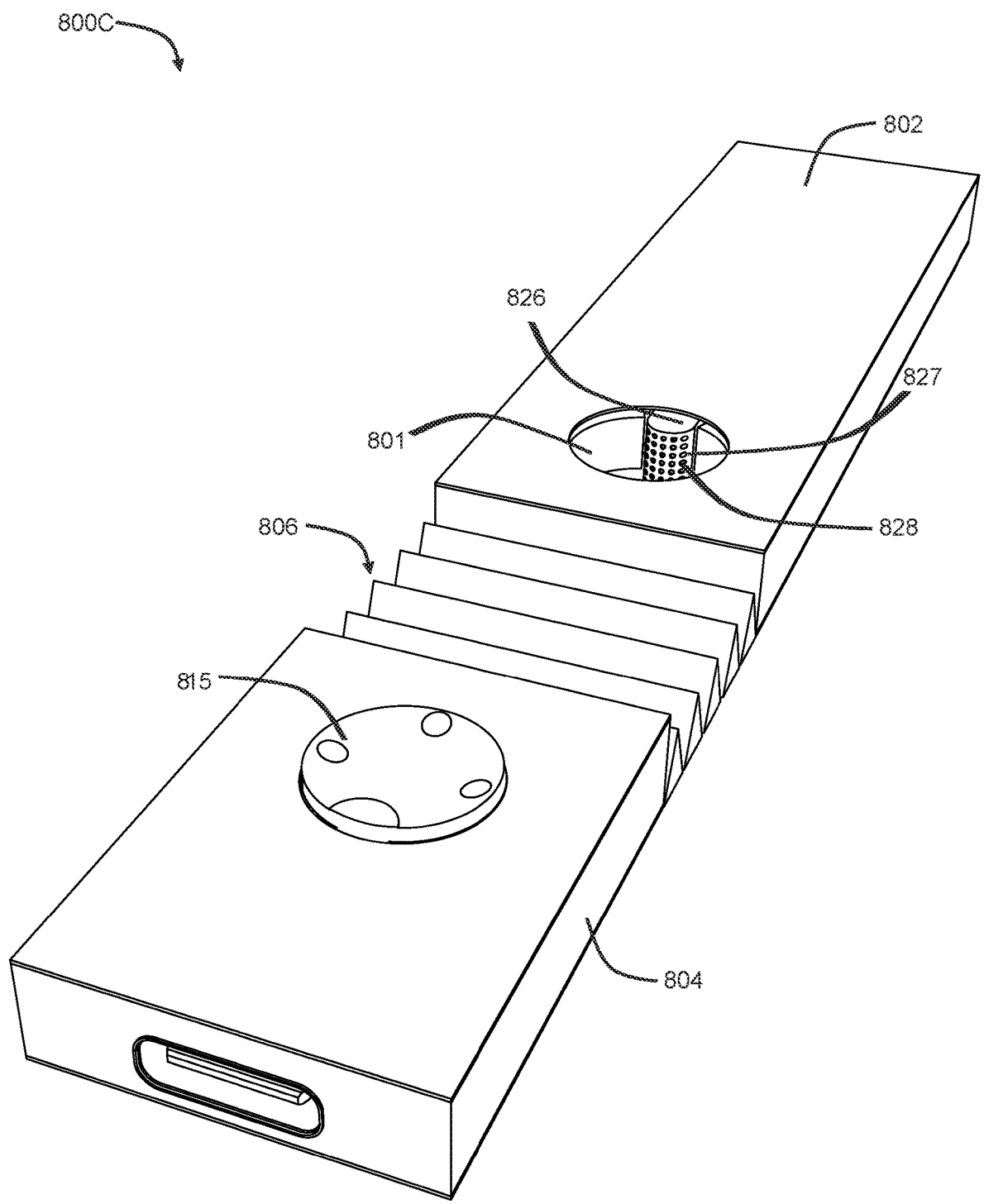
FIG. 8E is another top perspective view of the example vaporization device of FIG. 8A.

The tablet retainer 855 may be moveable between a retracted position (shown in FIG. 8A) and an extended position (shown in FIG. 8C). In the retracted position, the tablet retainer 855 may retract into the housing 808 of the first portion 802 to provide access to the heating chamber 805. This may facilitate removal of a spent tablet. This provides for access to the heating chamber from both sides, which making easier to remove the tablet. This may allow a user to/or extract/discard a spent or used tablet.

In the extended position (shown in FIG. 8C) the tablet retainer 855 may extend across and cover the underside opening of the heating chamber 805. When the retainer 855 is in the extended position, a user can insert a tablet into the heating chamber 805 from the open upper side (assuming the lid 830 is also in the open position). The tablet retainer 855 can thus hold the tablet within the heating chamber 805. By providing a tablet retainer 855 on the underside of the vaporization device, insertion and removal of the tablet 700A may occur away from the air inlet. This may reduce the debris that enters the air inlet region.

The vaporization device 800B may include a manual actuator usable to move the retainer 855 between the retracted and extended positions. For example, the actuator may include a tab (not shown) coupled to the retainer 855 that can be manually actuated by a user to adjust the position of the retainer. In some cases, the tablet retainer 855 may be biased to the extended position. Accordingly, the tablet retainer 855 may return to the extended position when a user releases the actuator.

In some cases, the vaporization device 800 may include an ejector (not shown). The ejector may be usable to eject a used tablet or phyto material from the heating chamber 805. By retracting the tablet retainer 855, a tablet positioned in the heating chamber 805 may be ejected without requiring a user to manually remove the tablet.

In some embodiments, the vaporization device 800C may include a third heating element 825C. The upper surface 815 of the heating chamber 805 provided by the lid 830 can include the third heating element 825C.

In some cases, the third heating element 825C may be usable to conductively heat a phyto material tablet positioned in the heating chamber 805. When the lid 830 is moved to the closed position, the top surface 815 may contact a tablet positioned in the heating chamber 805. In some cases, the top surface 815 may even compress and/or fracture a tablet positioned in the heating chamber 805. The third heating element 825C may then conductively heat the tablet portions in contact therewith.

Additionally or alternatively, the third heating element 825C may also provide convective heating for air drawn into the heating chamber 805. Air entering the air inlet 841 can pass through the third heating element 825C and be heated by the third heating element 825C. This heated air may further serve to vaporize the phyto material positioned in the heating chamber 805. Accordingly, the third heating element 825C may include air flow passages or apertures to allow air to pass from the air inlet 841 into the heating chamber 805 through the third heating element 825C.

In some cases, the vaporization device 800 may also include an additional ambient air inlet along the fluid pathway 842. The additional ambient air inlet may cool the vapor passing through the fluid pathway 842 to the inhalation aperture 840. This may be particularly useful in embodiments using a third heating element 825C to cool the air being drawn through the heating chamber 805 (to ultimately mix with the vapor and be inhaled) which will have been heated by the third heating element 825C.

Phyto material such as a tablet, loose phyto material, or extract positioned in the heating chamber 805 may be substantially enclosed therein (apart from apertures for an air inlet and a vapor inlet). By heating the heating chamber 805 from substantially all sides, the surface area of the phyto material exposed to conductive heating may be increased. Additionally, this may reduce the distance to a heating element for the phyto material that may be positioned centrally in the heating chamber 805 or in the middle of a tablet. For example, upwards of 90% or greater of the inner surface area of the heating chamber 805 may provide (or be in direct contact with) a heating element 825. This may increase the uniformity and completeness of the vaporization, which can provide benefits such as improved flavor and a denser vapor for inhalation.

By substantially surrounding phyto material or a tablet positioned in the heating chamber 805 with heating elements, the time required to heat the heating chamber 805 to a desired vaporization temperature may be reduced. This may provide an improved user experience, as the time required to vaporize phyto material positioned in the heating chamber can be reduced. Additionally, reducing the time required to vaporize phyto material positioned in the heating chamber 805 may reduce the energy required for a given vaporization session.

In some cases, as described herein above, the floor 810 of the heating chamber 805 may be textured or have a non-planar surface profile. This may provide airflow channels below a phyto material tablet positioned in the heating chamber 805 to facilitate the flow of air and vapor into the vapor inlet 826.

Figure 8F:
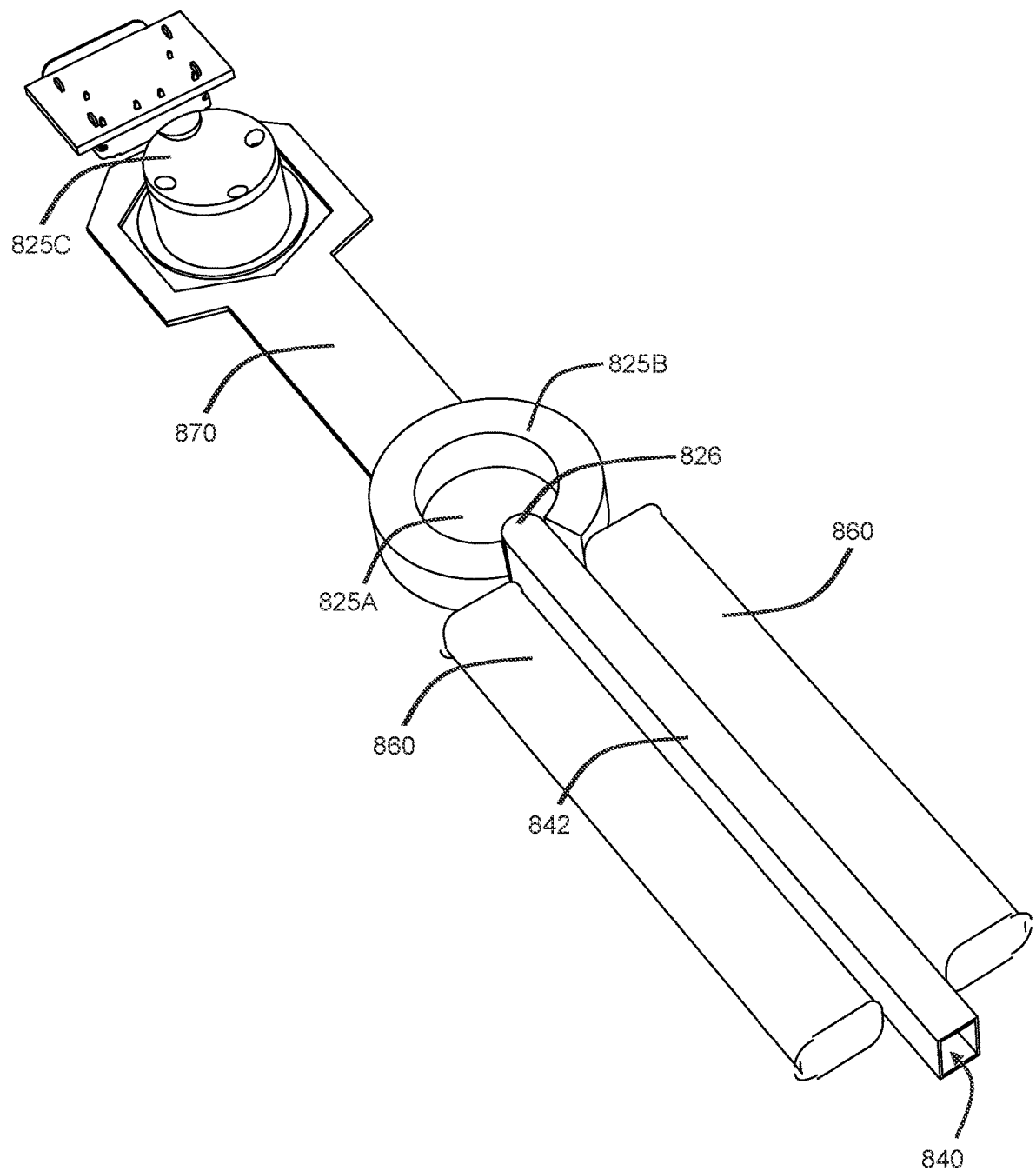
FIG. 8F is a schematic diagram of components of the example vaporization device of FIG. 8A.
Figure 8G:
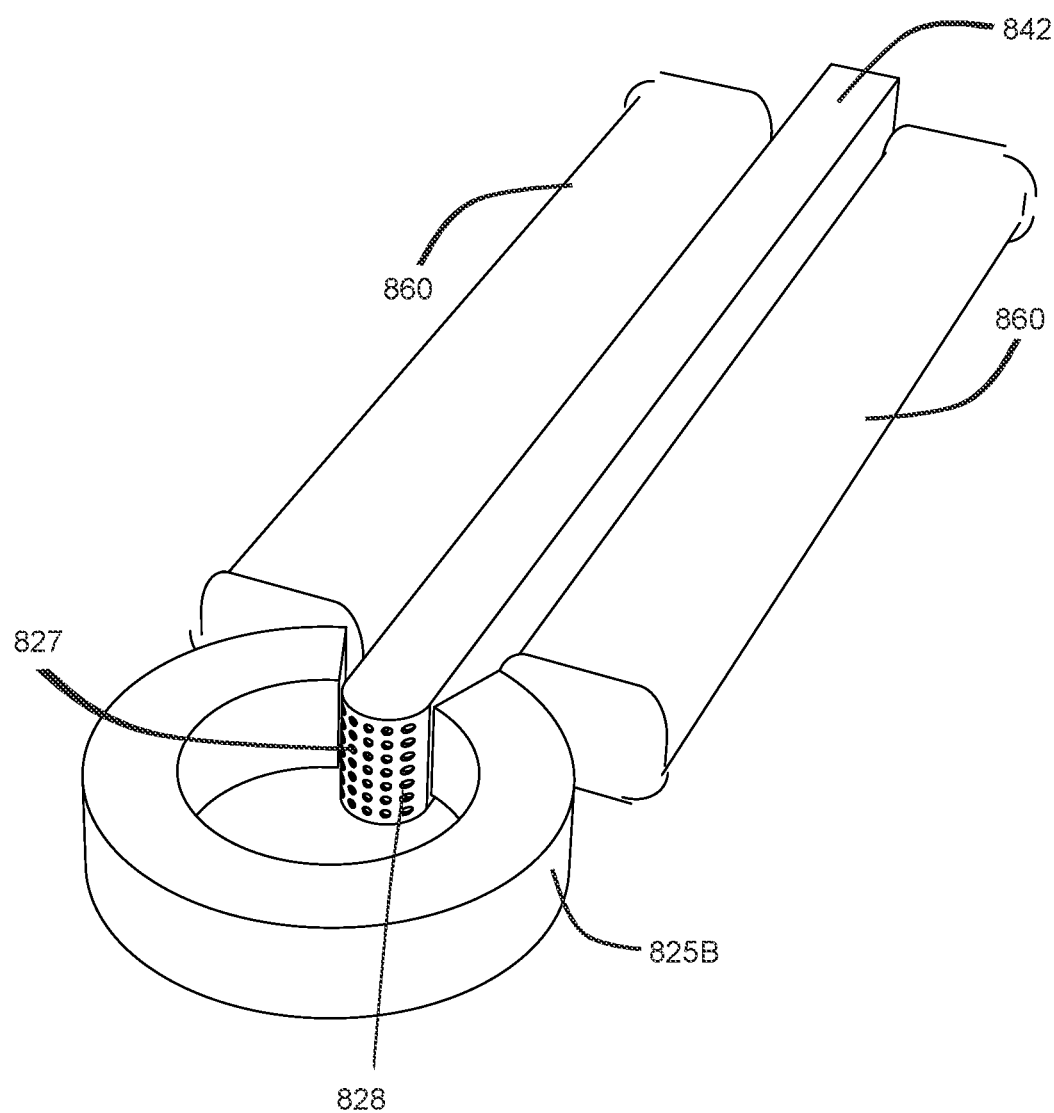
FIG. 8G is an isolation view of the heating chamber and energy storage components of the example vaporization device of FIG. 8A.

As shown in FIGS. 8F and 8G, the housing 808 of the first portion 802 may enclose an onboard energy source for the vaporization device 800. In the example of FIGS. 8F and 8G, the onboard energy source includes a pair of batteries 860.

The vaporization device 800 can also include a charging port 865 to allow the batteries 860 to be recharged. As shown in FIG. 8B, for example, the charging port 865 may be a USB charging port.

The vaporization device 800 may also include a printed circuit board (PCB) 870. The PCB 870 may include the electronic power and control components of the vaporization device 800. The PCB 870 may be flexible to allow the PCB 870 to bend as the lid 830 is transitioned to the closed position.

Referring now to FIGS. 9A-9G, shown therein is another example embodiment of a vaporization device 900. The vaporization device 900 may be generally similar to the vaporization devices 800, 800A and 800B described above with reference to FIGS. 8A-8G. However, in vaporization device 900 the pivotable coupling 906 between the first portion 902 and the second portion 904 has a substantially reduced profile as compared to hinge section 806.

Figure 9A:
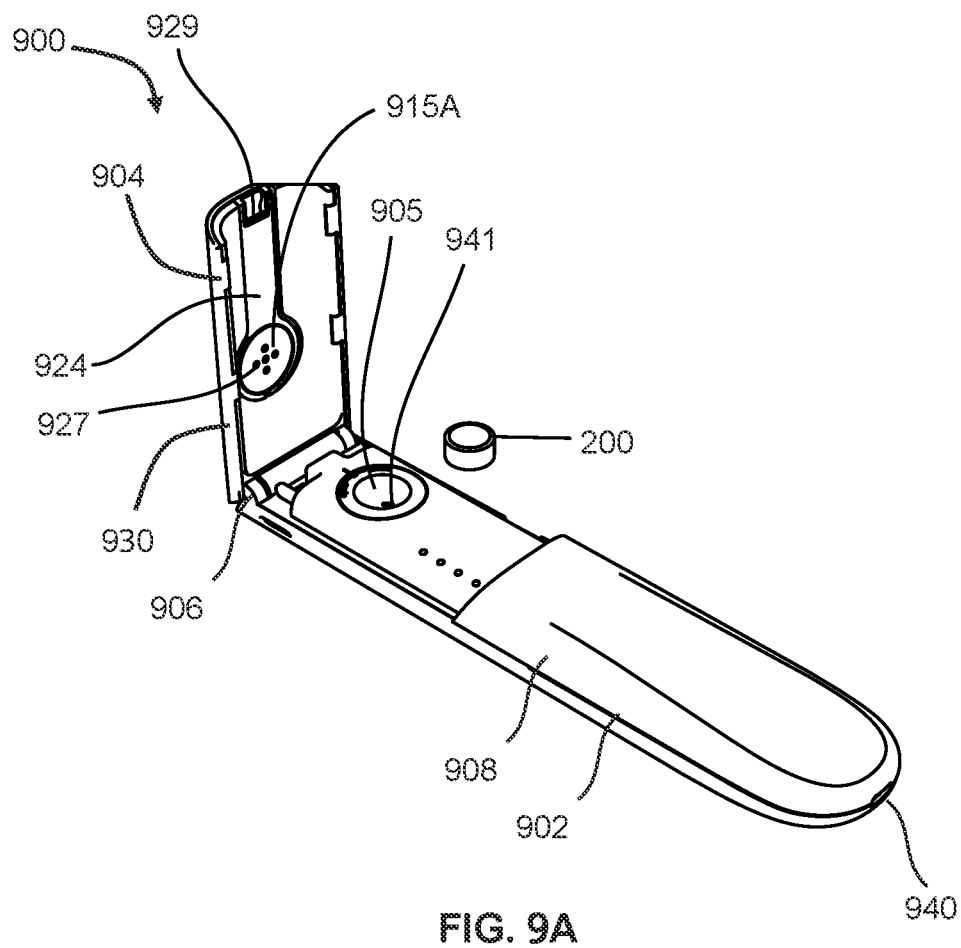
FIG. 9A is a top perspective view of an example vaporization device with the lid in an open position in accordance with an embodiment.
Figure 9B:
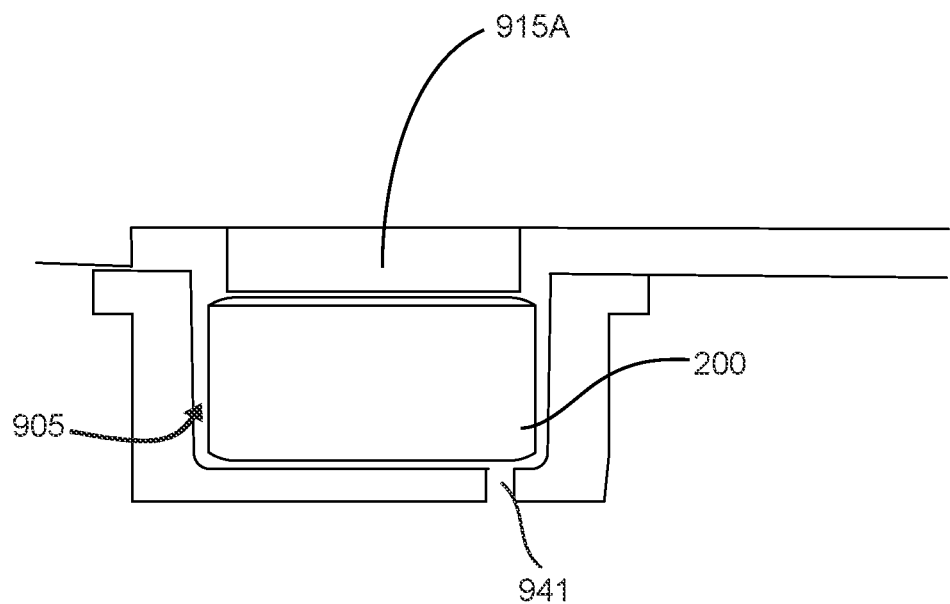
FIG. 9B is a partial sectional side view of the heating chamber of the example vaporization device of FIG. 9A with a phyto material tablet in the heating chamber in accordance with an embodiment.
Figure 9C:
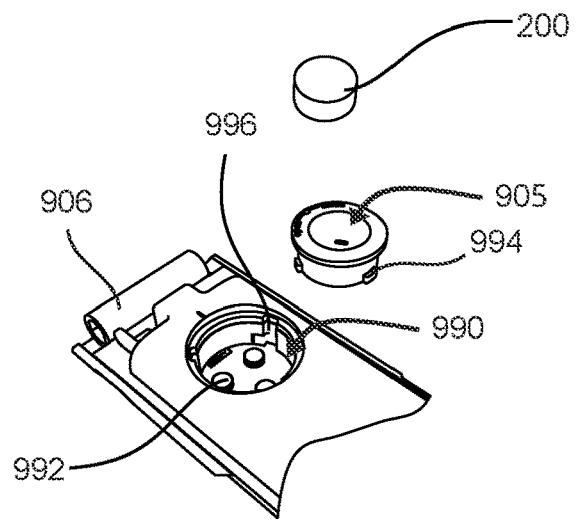
FIG. 9C is a partial exploded perspective view of the heating chamber of the example vaporization device of FIG. 9A in accordance with an embodiment.
Figure 9D:
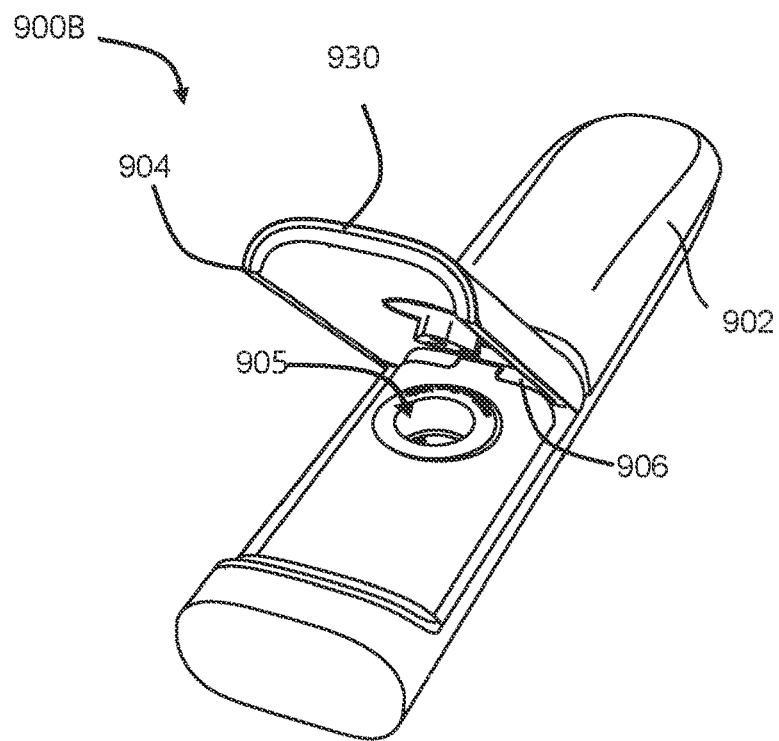
FIG. 9D is a top perspective view of a variant of the example vaporization device of FIG. 9A with the lid in an open position in accordance with an embodiment.
Figure 9E:
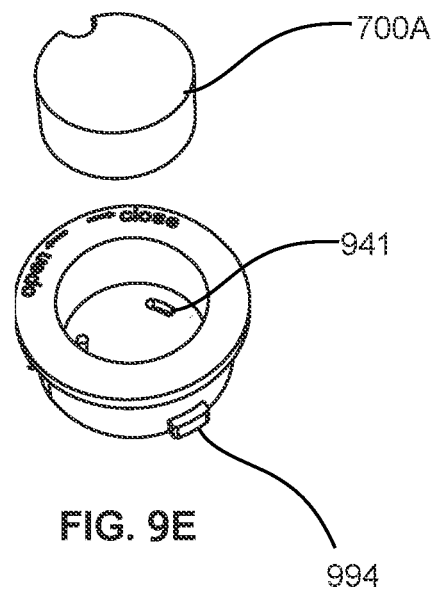
FIG. 9E is a top perspective view of an example phyto material tablet above an example heating chamber for the vaporization device of FIG. 9A in accordance with an embodiment.
Figure 9F:
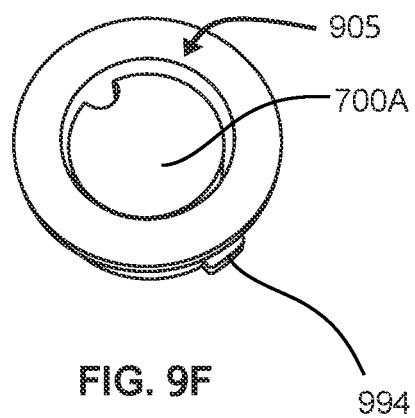
FIG. 9F is a top perspective view of an example phyto material tablet positioned within the heating chamber of FIG. 9E in accordance with an embodiment.

As shown in FIG. 9A, the first portion 902 can extend the entire length of vaporization device 900. The second portion 904 may then provide a lid 930 that can overlie the heating chamber 905 provided by the first portion 902.

In some cases, the second portion 904 may not include any active electrical and/or electronic components. For example, in embodiments using only two heating elements (provided by the floor and sides of heating chamber 905), the second portion 904 may merely provide the lid 930 for the heating chamber 905. This may reduce the possibility of failure due to connections having to pass through the hinge section 906. Additionally, this may facilitate manufacturing of the device 900 as a flexible PCB may not be required.

In other cases, the second portion 904 may include active elements, such as a third heating element and/or charging components as shown above with vaporization devices 800, 800A and 800B.

The inhalation aperture 940 is formed as an aperture in the surface of the housing 908. While in vaporization device 800 the inhalation aperture 840 protrudes from the surface of housing 808, the inhalation aperture 940 is formed flush with the surface of housing 908.

Additionally, the shape of the vaporization device 900 is softened as compared to the vaporization device 800. The edges and corners of the housing 908 are rounded, whereas in vaporization device 800 the edges and corners of 808 are more abrupt. Rounding the corners and edges of the housing 908 can make it more comfortable for a user to hold the vaporization device 900 when vaporizing phyto material. Additionally, providing an inhalation aperture 940 flush with a rounded end of the vaporization device 900 may provide a more comfortable mouth-feel for a user when inhaling from the inhalation aperture 940.

In vaporization devices 800, 800A, 800B and 900 the hinge section 806/906 is provided at the end of the first portion 902. However, in some embodiments such as vaporization device 900B, the hinge section 906 may be located more centrally along the first portion 902 (see e.g. FIG. 9D). Accordingly, the pivotable section 906 may be hidden or enclosed when the lid 930 is in the closed position. This may protect the hinge section 906 as well as provide a sleeker external profile to the vaporization device 900B.

As shown, an inner surface of the lid 930 can define an upper surface 915A of the heating chamber 905 when the lid 930 is moved to the closed position. The upper surface 915A can include a plurality of apertures that define a vapor inlet

927. Vapor emitted from a phyto material tablet that is vaporized within the heating chamber 905 can then pass into the vapor inlet 927.

The lid 930 can define an enclosed lid vapor pathway that extends from the vapor inlet 927 to a lid vapor outlet 929. When the lid 930 is in the closed position, the lid vapor outlet 929 can engage a fluid passage defined within the first section 902 that extends to inhalation aperture 940. As a result, a fluid flow pathway can be defined from the heating chamber 905 to inhalation aperture 940 that includes a section passing through the lid 930.

The pore size of the vapor inlet 927 may be selected to reduce or prevent particles of the phyto material from entering the lid vapor pathway. In some embodiments, the pore size may be between about 0.3 mm and 0.9 mm.

In some cases, as mentioned above, a filter or screen, such as a metal screen, may also be provided at the vapor inlet to reduce or prevent particles from entering the vapor flow path.

The lid 930 can also include a cooling assembly 924. The cooling assembly 924 may extend between the vapor inlet 927 and the lid vapor outlet 929. The cooling assembly 924 may encourage cooling of the vapor emitted from the heating chamber 905 prior to the vapor reaching the inhalation aperture 940. For example, an outer surface of the cooling assembly 924 may be formed using a thermally conductive material (e.g. metal) to provide heat transfer between the lid fluid flow passageway and the external environment.

In some cases, the cooling assembly 924 can define a winding or snaking vapor flow pathway. This may provide a longer pathway to encourage additional heat transfer. In some cases, this may also assist in filtering particles prior to reaching inhalation aperture 940.

The heating chamber 905 can define a chamber cavity within which a phyto material tablet can be positioned. In the example shown, the heating chamber 905 has a generally cylindrical chamber cavity. In other cases, other shapes may be used, such as a triangular chamber cavity (see e.g. FIGS. 10A-11A). The shape of the chamber cavity can be defined to correspond to a phyto material tablet being used in the vaporizer 900.

As described herein above, a heating element assembly may be integrated into the heating chamber 905. The heating element assembly may be used to heat one or more regions of the heating chamber 905, such as the base and/or sidewalls.

The heating chamber 905 can include one or more air inlets 941. The air inlets may allow ambient air to be drawn into the heating chamber 905 to encourage the flow of vapor out of the heating chamber 905 towards the inhalation aperture 940.

Figure 9G:
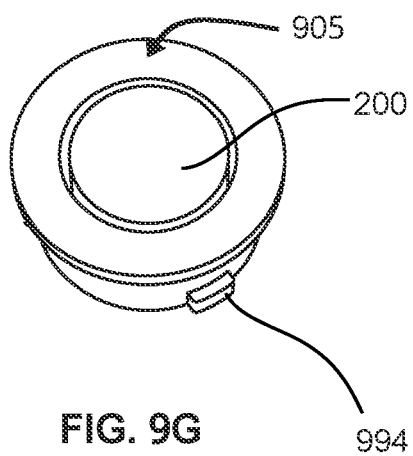
FIG. 9G is a top perspective view of another example phyto material tablet positioned within the heating chamber of FIG. 9E in accordance with an embodiment.

In some cases, as shown in FIG. 9G for example, the tablet 200 may have a diameter that is smaller than the inside diameter of the heating chamber 905. For example, the tablet 200 may have a diameter of about 10.4 and the inside diameter of the heating chamber 905 may be about 10.8 mm. This may provide a gap (e.g. 0.2 mm either side) between the tablet 200 and the sidewall 901 of the heating chamber 905. The gap may encourage airflow around the tablet 200.

In some embodiments, some or all of the sidewalls of the heating chamber 905 may include air inlets 942. This may allow air to flow into the chamber cavity of heating chamber 905. In some cases, the air inlets 942 may be arranged at spaced intervals around the heating chamber 905. This may encourage airflow around phyto material positioned within the heating chamber 905, which may facilitate inhalation and encourage more phyto material to be vaporized.

In some embodiments, the heating chamber 905 may be removable from the vaporization device 900. For example, the heating chamber 905 may be removably mounted to a heating chamber base 990. Various mounting assemblies may be used, such as snap mounting members, friction mountings, bayonet mountings etc. This may facilitate removal of the heating chamber 905 for maintenance or replacement. This may also allow hating chambers with different shapes of chamber cavity to be used with the same vaporization device 900.

In the example shown, the heating chamber 905 can include a plurality of mount engagement members 994. The base unit 990 can include a corresponding plurality of heating chamber engagement member 996. The heating chamber 905 can be mounted to the vaporization device by securing the mount engagement members 994 within the heating chamber engagement members 996.

In the example shown, the heating chamber 905 can be lowered into the base unit 990 with the mount engagement members 994 aligned with a vertical section of the heating chamber engagement members 996. The heating chamber 905 may then be rotated to secure the heating chamber 905 to the vaporization device by positioning the mount engagement member 994 in a lock portion of the heating chamber engagement members 996. The lock portion can engage the mount engagement members 994 and prevent vertical movement of the heating chamber 905. The heating chamber 905 may include directions that indicate to a user how to insert/remove heating chamber 905 (see e.g. FIG. 9E).

In the example shown, the base 990 can include electrical contacts 992. This may allow power to be transmitted to heating elements integrated within the heating chamber 905 when the heating chamber 905 is installed. In some cases, the contacts 992 may also provide for the flow of feedback signals (e.g. from a temperature sensor) from the heating chamber 905.

In some embodiments, the heating element assembly can be configured using a resistive heating element. The heating element may facilitate conductive heating of phyto material positioned within the heating chamber 905 by heating the inner sidewalls of the heating chamber 905. For example, a resistive ink may be sintered to a ceramic heating chamber. In other cases, a resistive wire may be embedded in the based and/or sidewalls of the heating chamber, or wrapped around the sidewalls of the heating chamber. In some cases, a thick film process may be used to deposit heater contacts, a heating wire, and insulators onto the outside surface of a metallic (e.g. stainless steel) heating chamber.

The heating element assembly may be activated by directing current through the resistive heating element. Heat from the heating element can radiate into the heating chamber 905 to heat phyto material positioned therein to a predetermined vaporization temperature. Vapor emitted from the heated phyto material can then pass into the vapor inlet 927 in response to a user inhaling through the inhalation aperture 940.

In some embodiments, an inductive heating element may be used. For example, the heating chamber 905 may be manufactured using metal. An inductive heating element may be used to inductively heat the heating chamber 905, and the heating chamber 905 can heat the tablet 200 in turn.

In some cases, the predetermined vaporization temperature may vary based on a user preference and/or the form of the phyto material. A user may adjust the predetermined vaporization temperature using input controls provided on the vaporization device 900. In some cases, a phyto material tablet may be vaporized at a predetermined vaporization temperature between about 350 degrees Fahrenheit and about 450 degrees Fahrenheit.

Figure 9H:
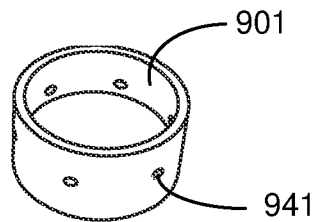
FIG. 9H is a top perspective view of an example heating chamber for the vaporization device of FIG. 9A in accordance with an embodiment.

FIG. 9H illustrates another example of a heating chamber 905B that may be used with the vaporizer 900. In heating chamber 905B, a plurality of air inlets 941 are positioned at intervals along the sidewall 901. As shown, the air inlets 941 are circumferentially spaced around the heating chamber 905B are regular intervals. In heating chamber 905B, the air inlets 941 are also positioned at about a midpoint of the sidewall 901 between the upper and lower sides of the heating chamber 905B. This may be desirable where the vaporizer air inlet is positioned laterally from the heating chamber 905B, as this may facilitate airflow into the heating chamber 905B.

Figure 9I:
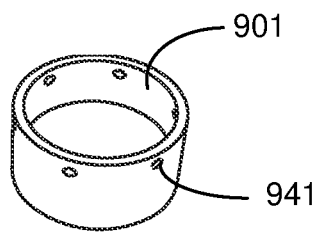
FIG. 9I is a top perspective view of another example heating chamber for the vaporization device of FIG. 9A in accordance with an embodiment.

FIG. 9I illustrates another example of a heating chamber 905C that may be used with the vaporizer 900. The heating chamber 905C is generally similar to the heating chamber 905B, except that the air inlets 941 are positioned proximate the upper end of the heating chamber 905C (e.g. away from the floor). This may be desirable where the vaporizer air inlet is positioned above (or laterally and above) the heating chamber 905C, as this may facilitate airflow into the heating chamber 905C. This may facilitate downward airflow through the heating chamber 905C, which may facilitate the outward flow of vapor when the chamber outlet is positioned in the floor or lower end of the heating chamber 905C.

Figure 9J:
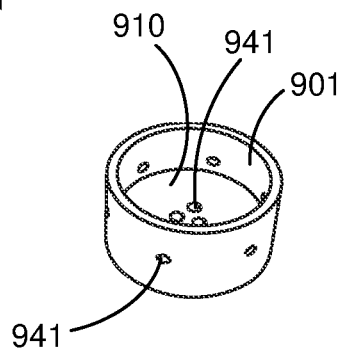
FIG. 9J is a top perspective view of another example heating chamber for the vaporization device of FIG. 9A in accordance with an embodiment.
Figure 9K:
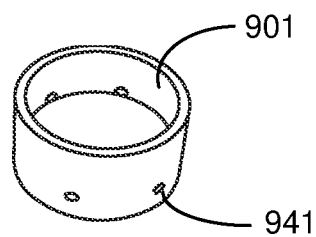
FIG. 9K is a top perspective view of another example heating chamber for the vaporization device of FIG. 9A in accordance with an embodiment.

FIG. 9K illustrates another example of a heating chamber 905E that may be used with the vaporizer 900. The heating chamber 905E is generally similar to the heating chambers 905B and 905C, except that the air inlets 941 are positioned proximate the lower end of the heating chamber 905C (e.g. near the floor). This may be desirable where the vaporizer air inlet is positioned below (or laterally and below) the heating chamber 905E, as this may facilitate airflow into the heating chamber 905E. This may facilitate upward airflow through the heating chamber 905E, which may facilitate the outward flow of vapor when the chamber outlet is positioned in the lid or upper end of the heating chamber 905E.

FIG. 9J illustrates another example of a heating chamber 905D that may be used with the vaporizer 900. The heating chamber 905D is generally similar to the heating chamber 905B, except that additional air inlets 941 are positioned in the floor 910 of the heating chamber 905D, in addition to the air inlets 941 in the sidewall 901. This may provide directed airflow at multiple sides of a tablet positioned in the heating chamber 905D. This may also encourage upward airflow through the heating chamber 905D, which may facilitate the outward flow of vapor when the chamber outlet is positioned in the lid or upper end of the heating chamber 905D.

Figure 9L:
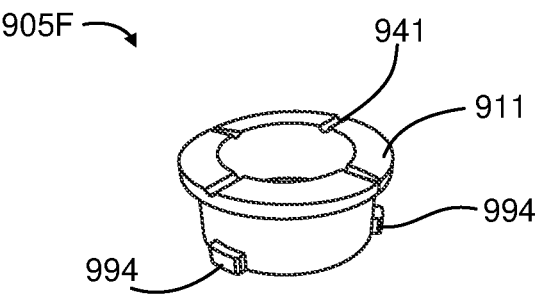
FIG. 9L is a side perspective view of another example heating chamber for the vaporization device of FIG. 9A in accordance with an embodiment.

FIG. 9L illustrates another example of a heating chamber 905F that may be used with the vaporizer 900. The heating chamber 905F is generally similar to the heating chamber 905, in that the heating chamber 905F includes a ridge or lip 911 at the upper end of the heating chamber 905F and includes mounting elements 994. In heating chamber 905F, air inlets 941 are provided in the lip 911, spaced circumferentially around the heating chamber 905F. This may encourage airflow along the top surface of a tablet positioned in the heating chamber 905F. This may also facilitate downward airflow through the heating chamber 905F, which may facilitate the outward flow of vapor when the chamber outlet is positioned in the floor or lower end of the heating chamber 905F.

In some cases, the vaporization device 900 may include a removable chamber positioned below the heating chamber 905. The removable chamber may be positioned to contain any phyto material that passes from the heating chamber 905 and into air inlets 941.

Figure 9M:
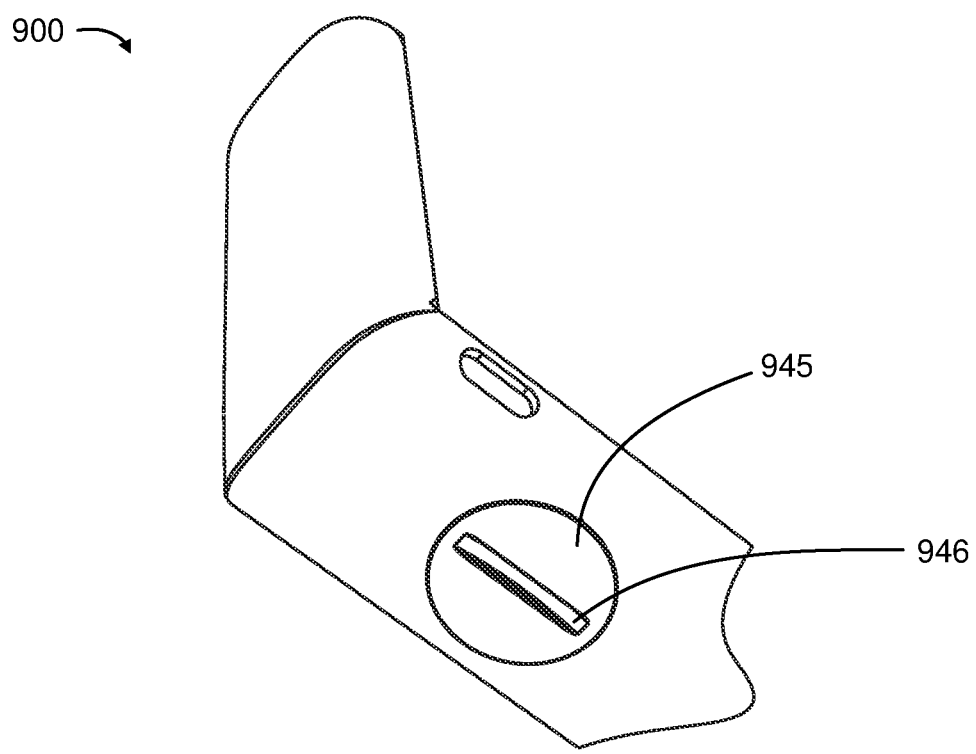
FIG. 9M is a bottom perspective view of the vaporization device of FIG. 9A showing an example of a removable chamber in accordance with an embodiment.
Figure 9N:
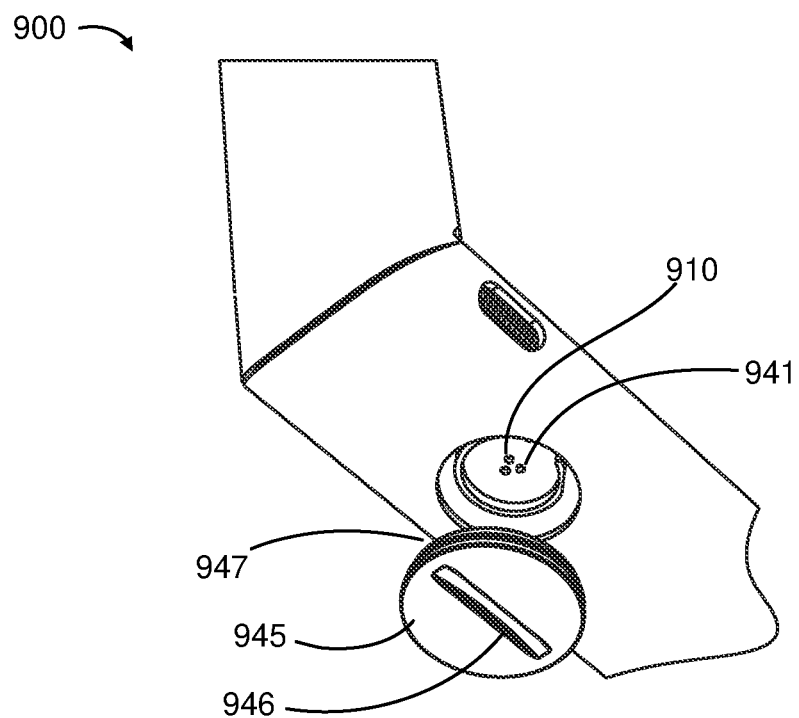
FIG. 9N is a bottom perspective view of the vaporization device of FIG. 9M with the removable chamber removed from the vaporization device in accordance with an embodiment.

As shown in FIGS. 9M-9N, the removable chamber 945 can be positioned to underlie the heating chamber 905. The removable chamber 945 may surround the air inlets 941. The removable chamber 945 may provide a collection area for debris or residue from the heating chamber 905 that may pass through the inlets 941, or otherwise fall below the heating chamber 905. The removable chamber 945 can be removed to dispose of the debris. This may also provide access to the underside of the heating chamber 905, to facilitate cleaning of heating chamber 905 and air inlets 941 while the heating chamber 905 is installed in vaporizer 900.

In the example shown, the removable chamber 945 includes threading 947 usable to mount the removable chamber 945 to the vaporizer 900. The removable chamber 945 can be screwed into, and unscrewed from, vaporizer 900 for installation or removal. As shown, the removable chamber 945 can include a slot 945 usable to attach and detach the removable chamber 945.

Figure 10A:
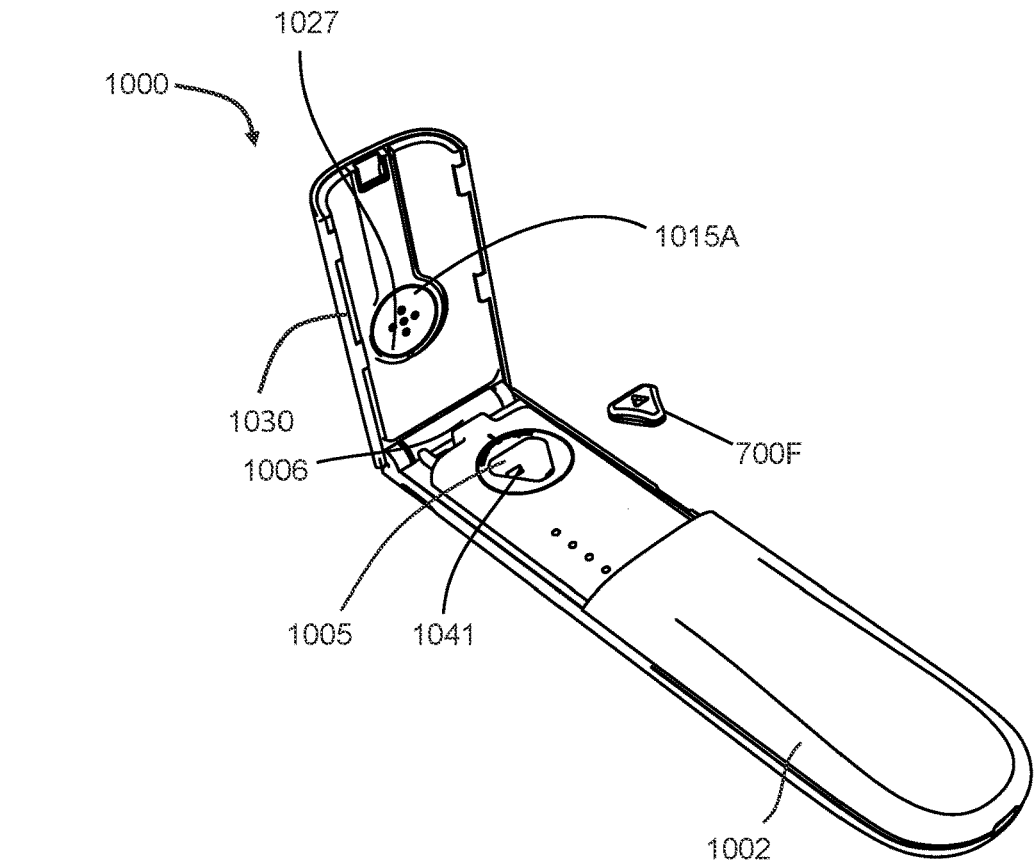
FIG. 10A is a top perspective view of an example vaporization device with the lid in an open position in accordance with an embodiment.
Figure 10B:
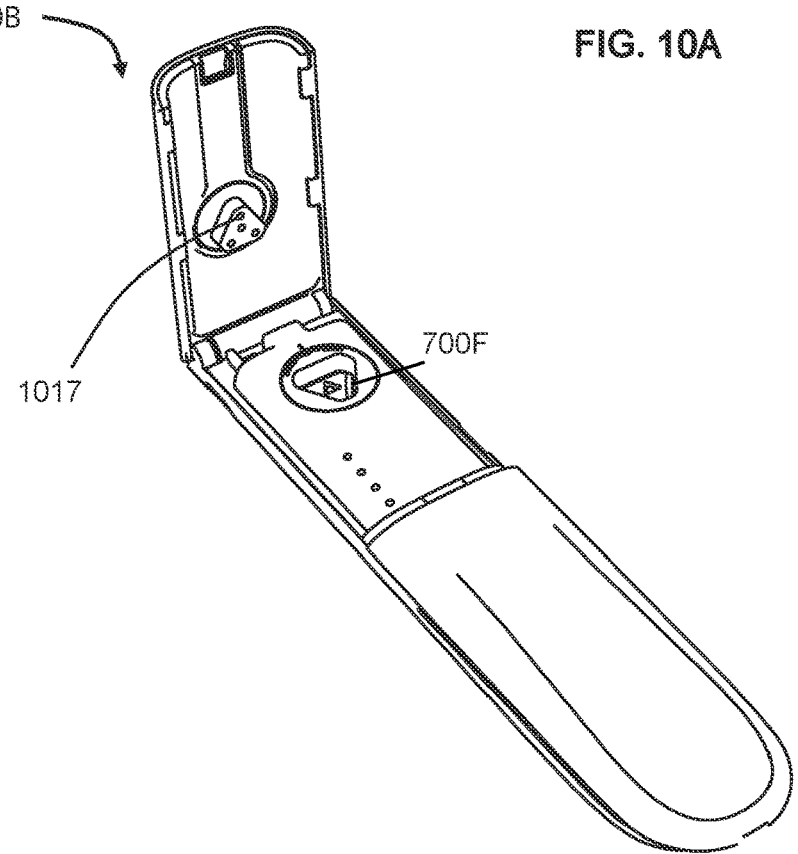
FIG. 10B is a top perspective view of a variant of the example vaporization device of FIG. 10A with the lid in an open position in accordance with an embodiment.

Referring now to FIGS. 10A-10F, shown therein is another example vaporization device 1000. FIG. 10B illustrates a vaporization device 1000B that is a variant of the vaporization device 1000. Reference numerals for vaporization device 1000 have been incremented by 100 relative to vaporization device 900.

Vaporization device 1000 is generally similar to vaporization device 900, except that the heating chamber 1005 is triangular rather than circular. As shown, the heating chamber 1005 is shaped to accommodate a substantially triangular phyto material tablet 700E/700F. The heating chamber 1005 can also include one or more air inlets 1041.

As with vaporization device 900, the lid 1030 of vaporization device 1000 defines an upper surface 1015A of the heating chamber 1005 when the lid 1030 is moved to a closed position. The upper surface 1015A includes a vapor inlet 927 into which vapor from phyto material within the heating chamber 1005 can pass.

The lid 1030 may be closed by rotating lid 1030 about the hinge 1006. Alternatively, the lid 1030 may be secured to the first section 1002 using engagement members, such as snap fittings. The lid 1030 may then be opened and closed by engaging/disengaging the engagement members and raising/lowering lid 1030.

As shown in FIG. 10B, the inner surface of the lid 1030 can include a projection member 1017. As will be appreciated, a projection member 1017 may be used with other configurations or shapes of heating chambers. The projection member 1017 can extend into the heating chamber 1005 when the lid 1030 is moved to a closed positioned.

The projection member 1017 can apply force on the upper surface of the tablet 700F positioned within the heating chamber 1005. The force may press the tablet 700F into the inner surfaces of the heating chamber 1005 to encourage heat transfer into tablet 700F. This may facilitate conductive heating from the floor and sidewalls of the heating chamber 1005 into the tablet 700F. The force applied by the projection member 1017 may also encourage fracturing of the tablet 700F. In some cases, the projection member 1017 can be configured to apply a force between about 0.1 Newton and 1 Newton.

Figure 10C:
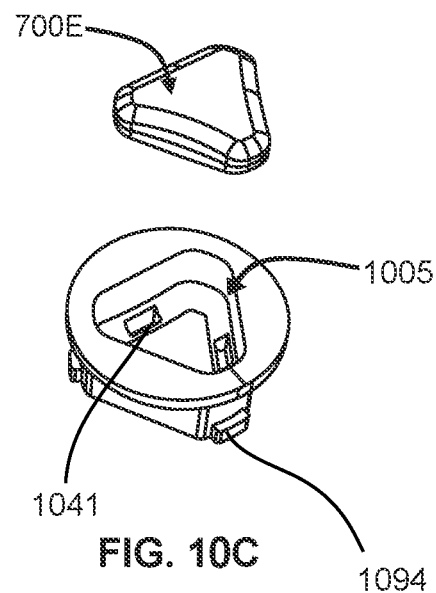
FIG. 10C is a top perspective view of a tablet above an example heating chamber for the vaporization device of FIG. 10A in accordance with an embodiment.
Figure 10D:
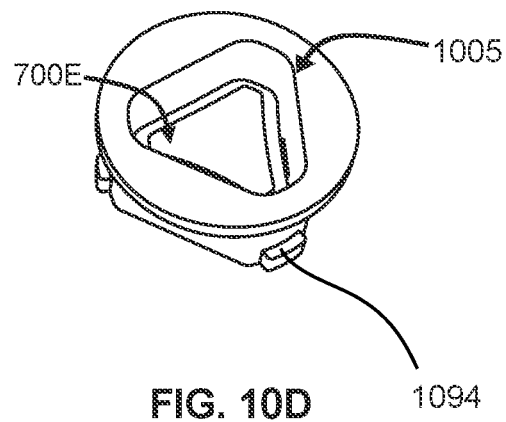
FIG. 10D is a top perspective view of an example tablet positioned within the heating chamber of FIG. 10C in accordance with an embodiment.

In some embodiments, as with heating chamber 905, the heating chamber 1005 may also be removable from the vaporization device 1000. As shown in FIGS. 10C and 10D, the heating chamber 1005 can include engagement members 1094 that can be used to secure the heating chamber 1005 to vaporization device 1000.

Figure 10E:
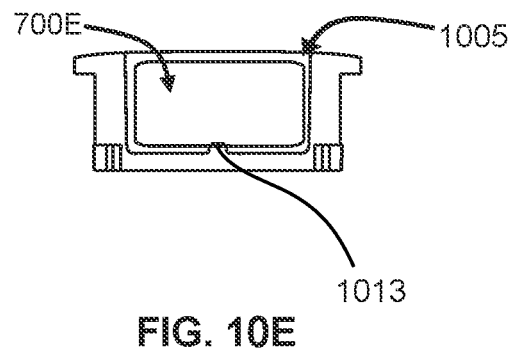
FIG. 10E is a partial sectional side view of the heating chamber of the example vaporization device of FIG. 10A with a phyto material tablet in the heating chamber in accordance with an embodiment.

In some embodiments, other surfaces of the heating chamber 1005 may include projection members. For example, as shown in FIG. 10E, the floor of the heating chamber 1005 can include an upwardly extending projection member 1013. In some cases, the projection member 1013 may extend into a tablet 700F positioned within the heating chamber 1005. This may allow for the interior of the tablet 700F to be heated directly through contact with projection member 1013.

In some cases, the projection member 1017 may compress the tablet 700F onto projection member 1013 encouraging the projection member 1013 to extend further into the tablet 700F. This may further facilitate heating the interior of the tablet 700F.

Figure 11A:
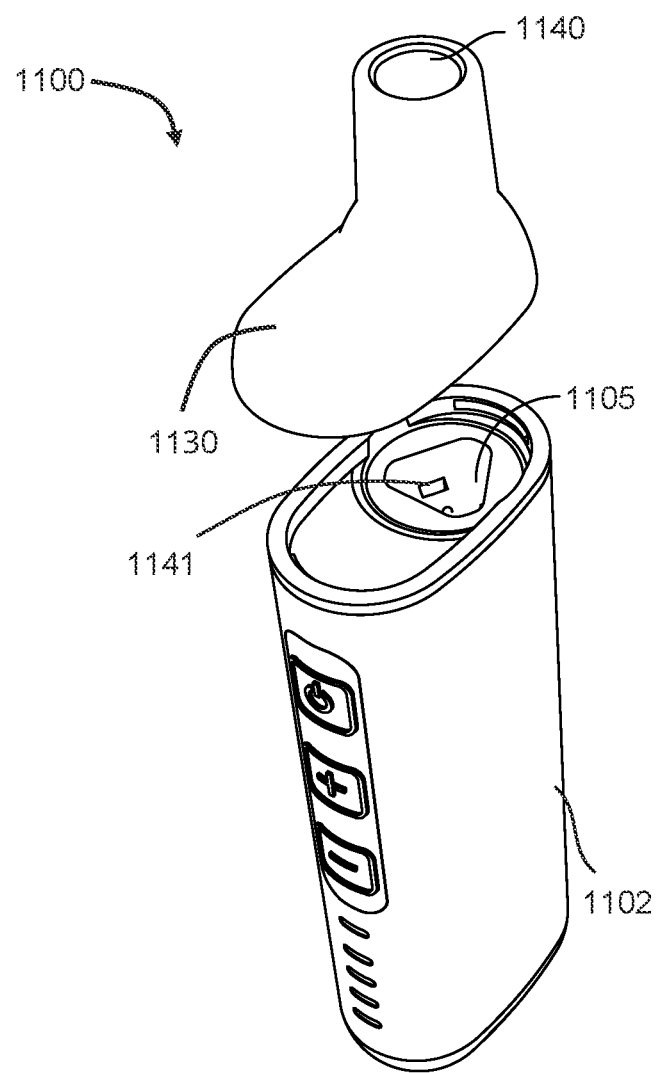
FIG. 11A is a top perspective view of an example vaporization device with the lid in an open position in accordance with an embodiment.
Figure 11B:
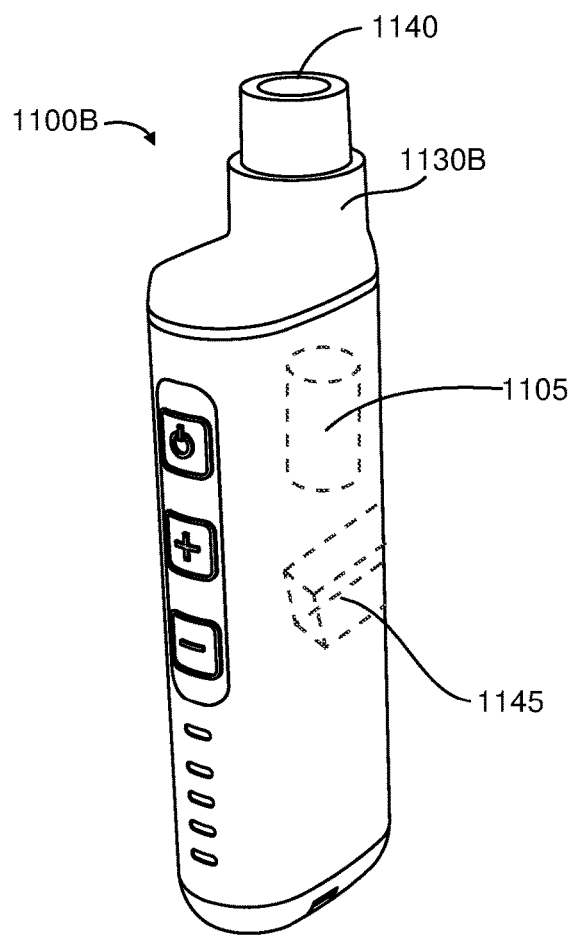
FIG. 11B is a side perspective view of a variant of the example vaporization device of FIG. 11A with the lid in a closed position in accordance with an embodiment.
Figure 11C:
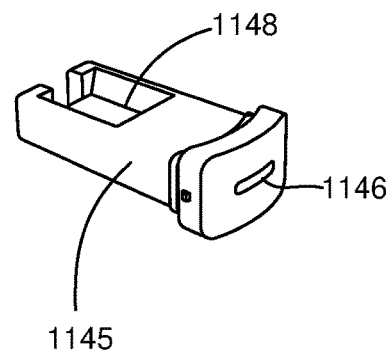
FIG. 11C is a front perspective view of an example of a removable chamber that may be used with the vaporization device of FIG. 11B in accordance with an embodiment.
Figure 11D:
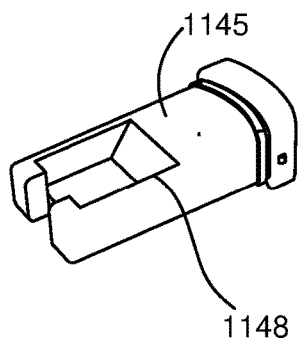
FIG. 11D is a rear perspective view of the example removable chamber of FIG. 11C.
Figure 11E:
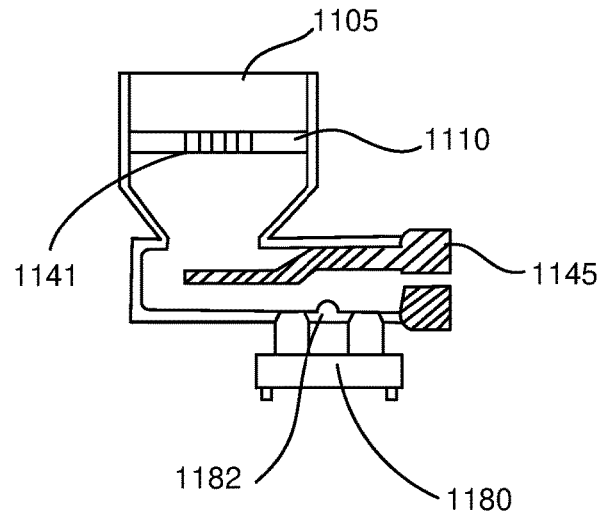
FIG. 11E is a partial section view of an example heating chamber and removable chamber that may be used with the vaporization device of FIG. 11B in accordance with an embodiment.

Referring now to FIG. 11A, shown therein is another example embodiment of a vaporization device 1100. Elements of vaporization device 1100 that are similar to vaporization device 1000 have been incremented by 100.

In the example shown, vaporization device 1100 includes a triangular heating chamber 1105, similar to vaporization device 1000. The vaporization device 1100 also includes a first section 1102 that defines a device base. A lid 1130 is detachably mountable to the first section 1102.

In vaporization device 1100, the lid 1130 includes a vaporization aperture 1140. The lid 1130 defines a removable mouthpiece that can be used to inhale vapor emitted from the heating chamber 1105. The lid 1130 encloses the entirety of the vapor flow path downstream from the heating chamber 1105. When removed, the lid 1130 provides access to the heating chamber 1105. This allows phyto material tablets to be loaded into, and unloaded from, the heating chamber 1105.

As shown, the lid 1140 can be frictionally mounted to the base 1102. The lid 1140 may engage the upper perimeter of the base 1102 to secure the lid in a closed position. The upper perimeter of the base 1102 may include a compressible section, e.g. an elastomeric rim along the perimeter, that can frictionally engage the lid 1140 when it is mounted to the base 1102. Additionally or alternatively, the lid 1140 and base 1102 may include further mounting members, such as mating engagement members or magnetic coupling members.

Referring now to FIGS. 11B-11E, shown therein is an example of a vaporization device 1100B that is a variant of vaporization device 1100. The vaporization device 1100B includes a modified mouthpiece 1130B that is mountable to the base 1102. The mouthpiece 1130B includes a lid of the heating chamber 1105 and an inhalation aperture 1140.

The vaporizer 1100B also includes a removable chamber 1145. The removable chamber 1145 is positioned below the heating chamber 1105. The chamber 1145 can provide a collection region 1148 for debris from the heating chamber 1105, similar to chamber 945. Debris from the heating chamber 1105 may fall through air inlets 1141 in the floor 1110 of the heating chamber. This debris may then be contained within the collection region 1148 of chamber 1145. The chamber 1145 can be removed so that the debris can be emptied from the collection region 1148. This may assist in cleaning the airflow path to the heating chamber 1105.

In vaporizer 1100B, the chamber 1145 is removed from a lateral side of the vaporizer 1100B rather than the bottom. The chamber 1145 may be secured in the vaporizer 1100B through frictional engagement with the base 1102. The chamber 1145 can include a slot 1146 usable to grasp chamber 1145 and slide it out from the vaporizer 1100B.

The size of the air inlets 1141 may vary depending on the type of phyto material intended to be used with vaporizer 1100B. Where finer ground phyto material is intended to be used, a smaller inlet size may be used to reduce the amount of debris passing to collection region 1148. Nonetheless, by providing a removable collection region 1148, larger air inlets 1141 may be used (which may facilitate airflow into heating chamber 1105) while allowing the airflow path to be cleaned.

In some embodiments, the vaporizer 1100B may also include an air flow sensor 1180. The air flow sensor 1180 may be coupled into the airflow path of the vaporizer 1100B, upstream from heating chamber 1105. The air flow sensor 1180 may be used to detect and/or measure airflow through the vaporizer 1100B.

Figure 14A:
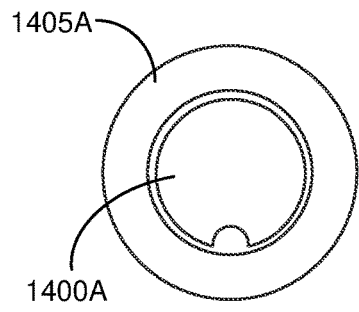
FIG. 14A is a top view of an example heating chamber with an example phyto material tablet in the heating chamber in accordance with an embodiment.

Referring now to FIG. 14A, shown therein is an example of a heating chamber 1405A having a tablet 1400A mounted therein. The heating chamber 1405A is generally similar to heating chamber 905 in that it has a generally cylindrical chamber cavity. The tablet 1400A is generally similar to tablet 700A, being a cylindrical tablet having a single recess extending the length of the side of the tablet.

As shown in FIG. 14A, when tablet 1400A is positioned within the heating chamber 1405A, the recess in the tablet 1400A may provide an airflow path along the side of the tablet 1400A. This may increase the surface area of the tablet 1400A exposed to heated air. This may also facilitate air circulation within the heating chamber 1405A. In addition, the recess may facilitate removal of the tablet 1400A from the heating chamber 1405A after vaporization, e.g. using a tool such as a pick.

As shown in FIG. 14A, a gap may also be provided between the inner sidewalls of the heating chamber 1405A and the tablet 1400A. This may facilitate airflow around the entirety of the tablet 1400A. For instance, in some examples, a gap of about 0.2 mm may be provided surrounding the tablet 1400A when the tablet 1400A is centered within heating chamber 1405A.

In some cases, the tablet 1400A may not seat directly in the center of the heating chamber 1405A. The gap may then be provided asymmetrical around the tablet 1400A.

Figure 14B:
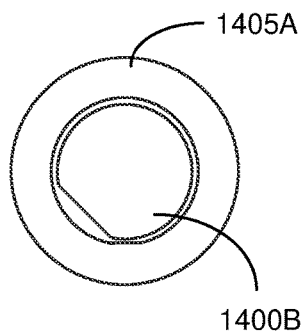
FIG. 14B is a top view of the heating chamber of FIG. 14A with another example phyto material tablet in the heating chamber in accordance with an embodiment.

Referring now to FIG. 14B, shown therein is heating chamber 1405A with another tablet 1400B mounted therein. The tablet 1400B is a modified form of tablet 1400A where instead of a recess, the cylindrical tablet 1400B has one flat side. When positioned in the cylindrical heating chamber 1405A, the effect of the flat side of tablet 1400B is similar to the recess provided by tablet 1400A.

Figure 14C:
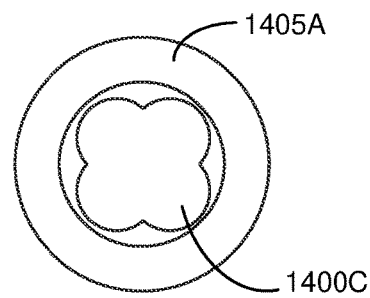
FIG. 14C is a top view of the heating chamber of FIG. 14A with another example phyto material tablet in the heating chamber in accordance with an embodiment.

Referring now to FIG. 14C, shown therein is heating chamber 1405A with another tablet 1400C mounted therein. Tablet 1400C is generally similar to tablet 700K described herein above. As shown, positioning tablet 1400C in a cylindrical heating chamber 1405A provided airflow passageways on multiple sides of the tablet 1400C. This may further encourage airflow within the heating chamber 1405A.

Figure 14D:
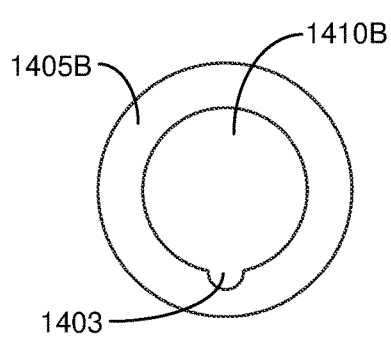
FIG. 14D is a top view of another example heating chamber in accordance with an embodiment.
Figure 14E:
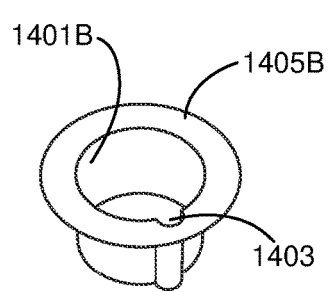
FIG. 14E is a top perspective view of the heating chamber of FIG. 14D.

Referring now to FIGS. 14D and 14E, shown therein is an example of a heating chamber 1405B. The heating chamber 1405B is generally similar to heating chamber 1405A, except that a chamber recess 1403 has been provided in the sidewall 1401B of the heating chamber 1405B. The chamber recess 1403 may provide an airflow passage through the heating chamber 1405B. The chamber recess 1403 may also assist in removing a tablet from the heating chamber 1405B, for instance by allowing a tool to access the side or bottom of a tablet positioned therein.

Figure 14F:
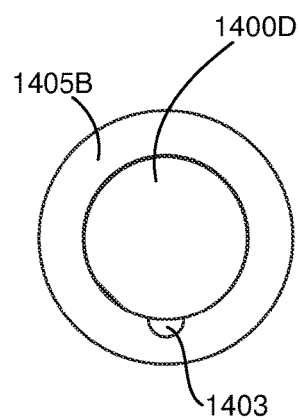
FIG. 14F is a top view of the heating chamber of FIG. 14D with an example phyto material tablet in the heating chamber in accordance with an embodiment.

FIG. 14F shows an example of a cylindrical tablet 1400D positioned within the heating chamber 1405B. As shown in FIG. 14F, the recess 1403 provides an airflow passage along one side of the tablet 1400D even though tablet 1400D extends substantially all the way to the sidewalls 1401B of heating chamber 1405B. This may encourage airflow within the heating chamber 1405B, even when the heating chamber 1405B is densely packed with phyto material or a large phyto material tablet.

Figure 14G:
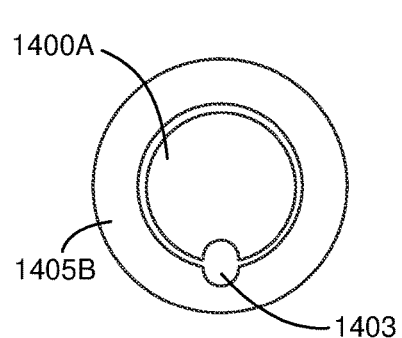
FIG. 14G is a top view of the heating chamber of FIG. 14D with the phyto material tablet of FIG. 14A in the heating chamber in a first position in accordance with an embodiment.

FIG. 14G shows an example of the tablet 1400A positioned within the heating chamber 1405B. In FIG. 14G, the recess in tablet 1400A is aligned with the chamber recess 1403. This may provide a larger airflow passage within the heating chamber 1405B. In some cases, this may also serve as an orientation marker to encourage a user to align the recesses.

Figure 14H:
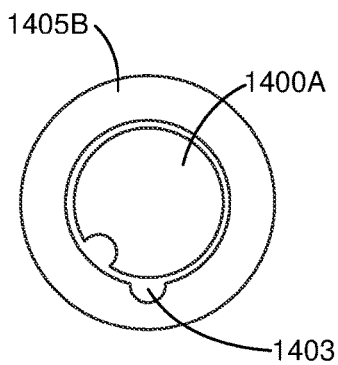
FIG. 14H is a top view of the heating chamber of FIG. 14D with the phyto material tablet of FIG. 14A in the heating chamber in a second position in accordance with an embodiment.

FIG. 14H shows the tablet 1400A positioned in the heating chamber 1405B, but at a slightly rotated positioned as compared to FIG. 14G. The tablet 1400A may provide an additional airflow passage within heating chamber 1405B.

Figure 14I:
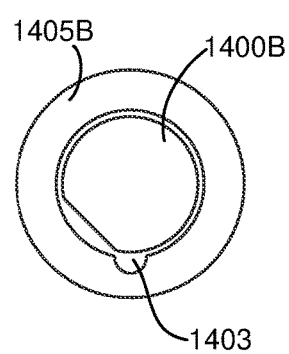
FIG. 14I is a top view of the heating chamber of FIG. 14D with the phyto material tablet of FIG. 14B in the heating chamber in accordance with an embodiment.

FIG. 14I shows the tablet 1400B positioned within heating chamber 1405B. As with FIG. 14H, the flat side of tablet 1400B is rotated to a non-aligned positioned with the recess 1403. The flat side of tablet 1400B can thus provide an additional airflow passage within heating chamber 1405B.

Figure 14J:
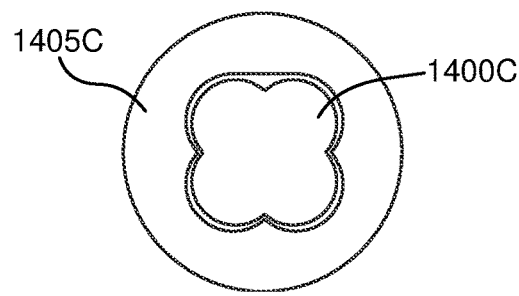
FIG. 14J is a top view of another example heating chamber with an example phyto material tablet in the heating chamber in accordance with an embodiment.
Figure 14K:
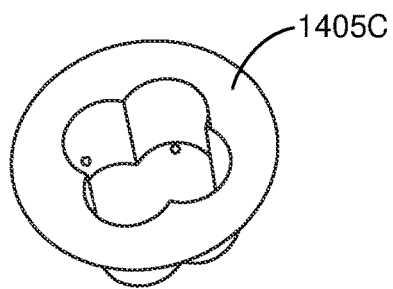
FIG. 14K is a top perspective view of the heating chamber of FIG. 14J.
Figure 14L:
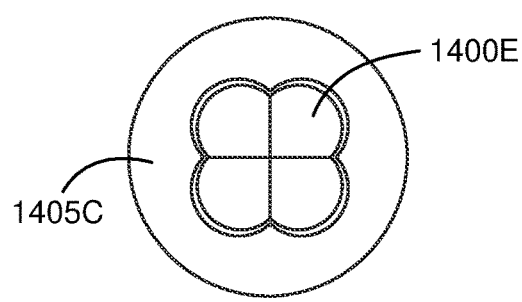
FIG. 14L is a top view of the heating chamber of FIG. 14J with another example phyto material tablet in the heating chamber in accordance with an embodiment.

FIGS. 14J-14L illustrate another example of a heating chamber 1405C. The heating chamber 1405C is shaped as a quatrefoil. As shown in FIGS. 14J and 14L, tablets 1400C and 1400E with a corresponding shape can be positioned within the heating chamber 1405C. In some cases, the tablets may include recesses or break regions in the top or bottom surfaces (see e.g. tablet 1400E in FIG. 14L). This may facilitate airflow across the surfaces of the tablet when the tablet occupies the majority of the heating chamber 1405C.

Figure 14M:
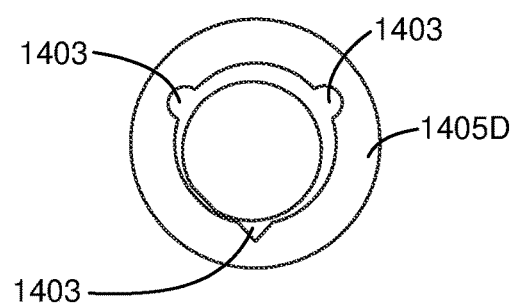
FIG. 14M is a top view of another example heating chamber in accordance with an embodiment.
Figure 14N:
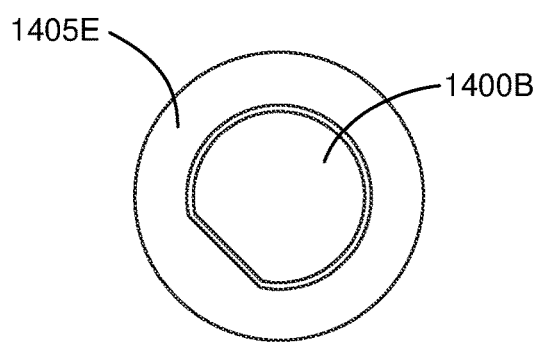
FIG. 14N is a top view of another example heating chamber with the phyto material tablet of FIG. 14B in the heating chamber in accordance with an embodiment.

FIG. 14M shows another example of a heating chamber 1405D. The heating chamber 1405D is a variant of heating chamber 1405B in which a plurality of recesses 1403 are spaced around the heating chamber 1405B. This may facilitate additional airflow as well as provide access to tablets in the heating chamber 1405D. As shown in FIG. 14M, in some cases the recesses 1403 may have shapes other than semi-circular recesses, such as triangular or rectangular recesses.

FIG. 14M shows another example of a heating chamber 1405E. The heating chamber 1405E is a generally cylindrical heating chamber that includes a flat side wall. The flat side wall of the heating chamber 1405E may provide a registration feature that ensures that a tablet 1400B is positioned within the heating chamber 1405E in a particular orientation. This may ensure that a user positions a tablet 1400B within the heating chamber 1405E in an orientation that is preferred for vaporization, for instance where the tablet 1400B includes a density gradient and/or variance in components across different layers or regions.

Figure 14O:
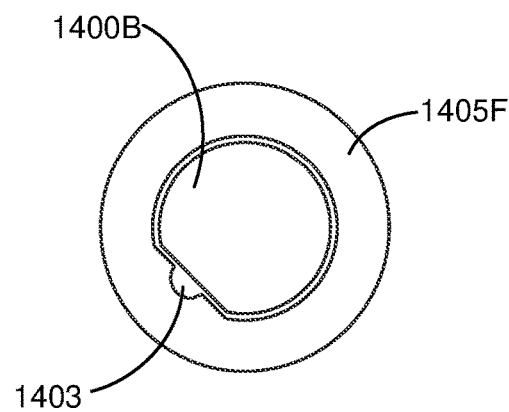
FIG. 14O is a top view of another example heating chamber with the phyto material tablet of FIG. 14B in the heating chamber in accordance with an embodiment.
Figure 15A:
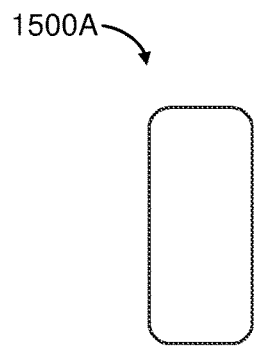
FIG. 15A is a top view of an example phyto material tablet in accordance with an embodiment.
Figure 15B:
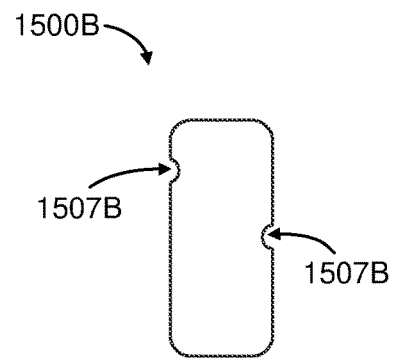
FIG. 15B is a top view of another example phyto material tablet in accordance with an embodiment.
Figure 15C:
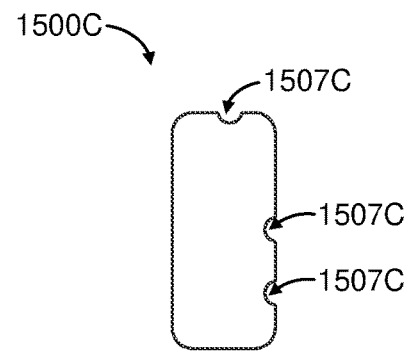
FIG. 15C is a top view of another example phyto material tablet in accordance with an embodiment.
Figure 15D:
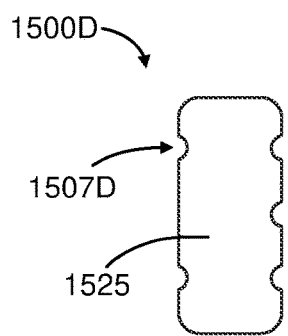
FIG. 15D is a top view of another example phyto material tablet in accordance with an embodiment.
Figure 15E:
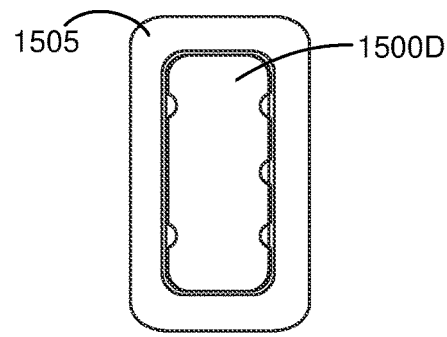
FIG. 15E is a top view of an example heating chamber with the phyto material tablet of FIG. 15D in the heating chamber in accordance with an embodiment.
Figure 15F:
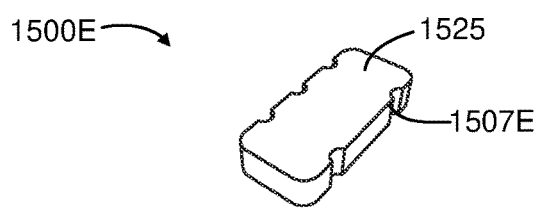
Figure 15G:
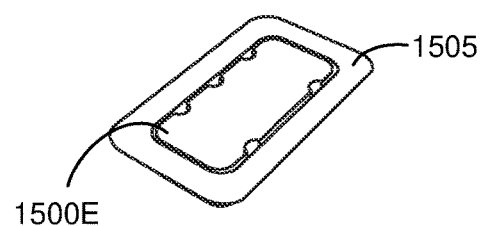

FIG. 14O shows another example of a heating chamber 1405F. The heating chamber 1405F is a variant of heating chamber 1405E in which a chamber recess 1403 is provided in the sidewall of the heating chamber 1405F. In this example, the recess 1403 is aligned with the flat side of the heating chamber 1405F. In combination with the flat side of the chamber 1405F providing a registration feature, this may ensure that air can flow along a specified side of a tablet 1400B positioned within the heating chamber 1405F.

Referring now to FIGS. 15A-15K, shown therein are various examples of tablets 1500A-1500F that have generally rectangular shapes. This may facilitate use with vaporizers having generally rectangular heating chambers, such as heating chambers 1505 and 1505B. The tablets 1500 may be provided in various sizes, such as about 17 mm-20 mm in length, about 8 mm-9 mm in width, and about 9 mm-11 m in depth for example.

In some cases, the tablets 1500 may be formed with one or more recess 1507 (see e.g. recesses 1507B, 1507C, 1507D, 1507E and 1507F). The recesses 1507 may facilitate access to the tablets 1500 when positioned in a heating chamber 1505. The recesses 1507 may also encourage airflow around the tablet 1500.

The heating chambers 1505 may also include chamber recess 1503 in some cases (see e.g. heating chamber 1505B). The chamber recesses 1503 may also facilitate airflow around the tablets 1500 and removal of the tablets 1500 from the heating chamber 1505B.

In some cases, the recesses 1507 may also provide orientation markers for the tablets 1500. For example, by arranging the recesses 1507 asymmetrically around the tablets 1500, the recesses can provide a visual indication to a user of the top surface or bottom surface of the tablet. In some cases, the heating chambers 1505 may be provided with corresponding alignment indicators. The alignment indicators may be alignable with orientation markers on the tablets 1500, which may facilitate proper alignment of the tablets 1500 in the heating chambers 1505.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A vaporization device comprising:
    an inhalation aperture;
    a heating chamber having a chamber base, at least one chamber sidewall, and a chamber lid, wherein the chamber base, the at least one chamber sidewall and the chamber lid together define a phyto material receiving cavity, the phyto material receiving cavity shaped to receive a phyto material tablet;
    at least one air inlet fluidly coupled to the heating chamber;
    at least one chamber vapor outlet provided in the chamber lid, the at least one chamber vapor outlet fluidly coupled to the heating chamber and the inhalation aperture;
    a vapor flow path that extends from the at least one air inlet through the heating chamber to the at least one chamber vapor outlet and then to the inhalation aperture;

a heating element assembly positioned proximate the heating chamber, the heating element operable to heat phyto material within the phyto material receiving cavity, wherein the at least one heating element is heatable to a predetermined vaporization temperature sufficient to heat the phyto material tablet when the phyto material tablet is positioned in the heating chamber and cause emission of vapor from the phyto material tablet, whereby the emitted vapor is fluidly coupled to the inhalation aperture via the vapor flow path;

wherein the vaporization device comprises a first body portion and a second body portion;

the first body portion includes the chamber base and the at least one chamber sidewall;

the second body portion includes the chamber lid;

the second body portion is adjustably mounted to the first body portion between an open position and a closed position, in the open position the chamber lid is open and the heating chamber cavity is accessible, and in the closed position the heating chamber cavity is enclosed by the chamber lid;

the second body portion encloses a lid section of the vapor flow path that is fluidly coupled to the heating chamber cavity when the second body portion is in the closed position;

the vaporization device comprises at least one projecting member included on at least one inner surface of the phyto material receiving cavity, each projecting member extends into the phyto material receiving cavity to thereby compress at least a portion of the phyto material tablet when the phyto material tablet is received in the phyto material receiving cavity and the chamber lid is secured to the chamber base enclosing the phyto material receiving cavity;

the first body portion comprises a downstream section of the vapor flow path that extends between a first portion vapor inlet and the inhalation aperture; and when the second body portion is in the closed position, the lid section of the vapor flow path extends between the at least one chamber vapor outlet and a lid outlet, the lid outlet being fluidly engageable with the first portion vapor inlet.

2. The vaporization device of claim 1, wherein the chamber lid is hingedly mounted to the chamber base, the chamber lid being moveable between the open position in which the heating chamber cavity is accessible and the closed position in which the heating chamber cavity is enclosed.

3. The vaporization device of claim 2, wherein the chamber base and the at least one chamber sidewall define a base portion of the phyto material receiving cavity, the base portion having an open upper end; and the at least one projecting member comprises a lid projecting member on an inner surface of the chamber lid that extends into the base portion when the lid is in the closed position.

4. The vaporization device of claim 3, wherein the lid projecting member extends across substantially all of the open upper end when the lid is in the closed position.

5. The vaporization device of claim 1, wherein the at least one air inlet comprises an ambient air inlet on the chamber lid and when the second body portion is in the closed position, a second lid section of the vapor flow path extends between the ambient air inlet and the heating chamber cavity.

6. The vaporization device of claim 1, further comprising a cooling assembly coupled to the lid section of the vapor flow path.

7. The vaporization device of claim 1, further comprising:

a dispensing magazine; and a tablet transport unit, the tablet transport unit operable to transport a phyto material tablet from the dispensing magazine into the heating chamber cavity.

8. The vaporization device of claim 7, wherein the dispensing magazine houses a plurality of phyto material tablets.

9. The vaporization device of claim 8, wherein the dispensing magazine is enclosed within a housing of the vaporization device.

10. The vaporization device of claim 1, wherein the heating element assembly comprises a plurality of heating elements, the plurality of heating elements including a first heating element positioned at the chamber base and a second heating element positioned at the at least one chamber sidewall.

11. The vaporization device of claim 10, wherein the plurality of heating elements comprises a third heating element positioned at the lid of the heating chamber.

12. The vaporization device of claim 1, wherein the at least one projecting member comprises at least one fracturing protrusion, wherein when the chamber lid is moved from the open position to the closed position, the fracturing protrusion applies a directed pressure sufficient to fracture the phyto material tablet positioned in the heating chamber.

13. The vaporization device of claim 1, further comprising a plunger that is moveable between an extended position and a retracted position, in the extended position the plunger projects into the heating chamber cavity, and in the retracted position the plunger is receded from the chamber cavity.

14. The vaporization device of claim 13, wherein the plunger is operable to translate a phyto material tablet from a dispensing magazine into the heating chamber cavity as the plunger moves from the retracted position to the extended position.

* * * * *